(12) United States Patent
Shem-Tov

(10) Patent No.: US 12,714,763 B2
(45) **Date of Patent: *Aug. 25, 2026**

(54) AUTOMATED VIAL PREPARATION MODULE

(71) Applicant: EQUASHIELD MEDICAL LTD, Migdal Tefen (IL)

(72) Inventor: Eric Shem-Tov, Ramat Hasharon (IL)

(73) Assignee: EQUASHIELD MEDICAL LTD, Migdal Tefen (IL)

( * ) Notice: Subject to any disclaimer, the term of this patent is extended or adjusted under 35 U.S.C. 154(b) by 0 days.

This patent is subject to a terminal disclaimer.

(21) Appl. No.: 19/174,365

(22) Filed: Apr. 9, 2025

(65) Prior Publication Data

US 2025/0339340 A1 Nov. 6, 2025

Related U.S. Application Data

(63) Continuation of application No. PCT/IL2025/050198, filed on Feb. 27, 2025.

(Continued)

(51) Int. Cl.

*B08B 1/30* (2024.01)
*A61J 1/14* (2023.01)

(Continued)

(52) U.S. Cl.

CPC ............... *A61L 2/18* (2013.01); *A61J 1/1406* (2013.01); *A61J 1/1443* (2013.01); *A61J 1/16* (2013.01); *A61L 2/10* (2013.01); *A61L 2/24* (2013.01); *A61L 2/26* (2013.01); *B08B 1/145* (2024.01); *B08B 1/30* (2024.01); *B08B 13/00* (2013.01);

(Continued)

(58) Field of Classification Search

CPC ..... A61L 2/18; A61L 2/10; A61L 2/24; A61L 2/26; A61L 2202/11; A61L 2202/14; A61L 2202/15; A61L 2202/17; A61L 2202/23; B08B 1/30; B08B 1/145; B08B 13/00; A61J 1/1406; A61J 1/1443; A61J 1/16;

(Continued)

(56) References Cited

U.S. PATENT DOCUMENTS

| | | | |
|---|---|---|---|
| 5,112,297 | A | 5/1992 | Stalcup et al. |
| 10,688,021 | B2 | 6/2020 | Tribble et al. |

(Continued)

FOREIGN PATENT DOCUMENTS

| | | | |
|---|---|---|---|
| CN | 206730176 | U | 12/2017 |
| CN | 114634145 | A | 6/2022 |

(Continued)

*Primary Examiner* — Tinsae B Ayalew
(74) *Attorney, Agent, or Firm* — Workman Nydegger

(57) ABSTRACT

An automated vial preparation module is provided that may include a vial mount for receiving a vial, a manipulator for disinfecting at least a portion of the vial, and control circuitry. The module may apply a disinfecting solution to a vial septum and wipe the septum with a swab. The module may include transferring means for moving vials. An imaging apparatus may monitor the vial preparation process. The module may interface with an automated pharmaceutical compounding system. Methods for automated vial preparation may include steps such as transferring a vial to a mount, removing a vial cap, disinfecting at least the vial septum, and mounting an adaptor onto the vial septum.

30 Claims, 25 Drawing Sheets

Related U.S. Application Data

(60) Provisional application No. 63/559,402, filed on Feb. 29, 2024.

(51) Int. Cl.

| | |
|---|---|
| ***A61J 1/16*** | (2023.01) |
| ***A61L 2/10*** | (2006.01) |
| ***A61L 2/18*** | (2006.01) |
| ***A61L 2/24*** | (2006.01) |
| ***A61L 2/26*** | (2006.01) |
| ***B08B 1/14*** | (2024.01) |
| ***B08B 13/00*** | (2006.01) |
| ***B25J 11/00*** | (2006.01) |
| ***G06T 7/00*** | (2017.01) |
| *A61L 103/00* | (2026.01) |

(52) U.S. Cl.

CPC ......... *B25J 11/0085* (2013.01); *G06T 7/0006* (2013.01); *A61J 2200/70* (2013.01); *A61L 2103/23* (2026.01); *A61L 2202/11* (2013.01); *A61L 2202/14* (2013.01); *A61L 2202/15* (2013.01); *A61L 2202/17* (2013.01); *G06T 2207/30108* (2013.01)

(58) Field of Classification Search

CPC . A61J 2200/70; B25J 11/0085; G06T 7/0006; G06T 2207/30108

USPC ........................................................ 134/56 R

See application file for complete search history.

(56) References Cited

U.S. PATENT DOCUMENTS

| | | | | |
|---|---|---|---|---|
| 2002/0132353 | A1 | 9/2002 | Tamura et al. | |
| 2003/0103839 | A1 | 6/2003 | Osborne et al. | |
| 2005/0224137 | A1 | 10/2005 | Tribble et al. | |
| 2006/0259195 | A1 | 11/2006 | Eliuk et al. | |
| 2008/0199353 | A1 | 8/2008 | Mlodzinski et al. | |
| 2014/0190277 | A1 | 7/2014 | Itoh | |
| 2015/0335531 | A1 | 11/2015 | Yuyama et al. | |
| 2016/0331857 | A1 | 11/2016 | Kawamura et al. | |
| 2017/0368516 | A1 | 12/2017 | Nichols | |
| 2018/0282008 | A1 | 10/2018 | Diaz Guerrero | |
| 2018/0297193 | A1 | 10/2018 | Garfield et al. | |
| 2019/0053873 | A1 | 2/2019 | Noell et al. | |
| 2019/0307643 | A1* | 10/2019 | Tribble | B65C 3/26 |
| 2022/0167953 | A1 | 6/2022 | Parvizi et al. | |
| 2022/0241984 | A1 | 8/2022 | Glasbrenner | |

FOREIGN PATENT DOCUMENTS

| | | | |
|---|---|---|---|
| CN | 119280447 | A | 1/2025 |
| CN | 223569704 | U | 11/2025 |
| DE | 1541271 | A1 | 9/1969 |
| EP | 2465483 | B1 | 6/2016 |
| JP | 2008212201 | A | 9/2008 |
| JP | 2019033790 | A | 3/2019 |
| KR | 20110106671 | A | 9/2011 |
| WO | 2004050038 | A1 | 6/2004 |
| WO | 2004098369 | A1 | 11/2004 |
| WO | 2023091719 | A1 | 5/2023 |

* cited by examiner

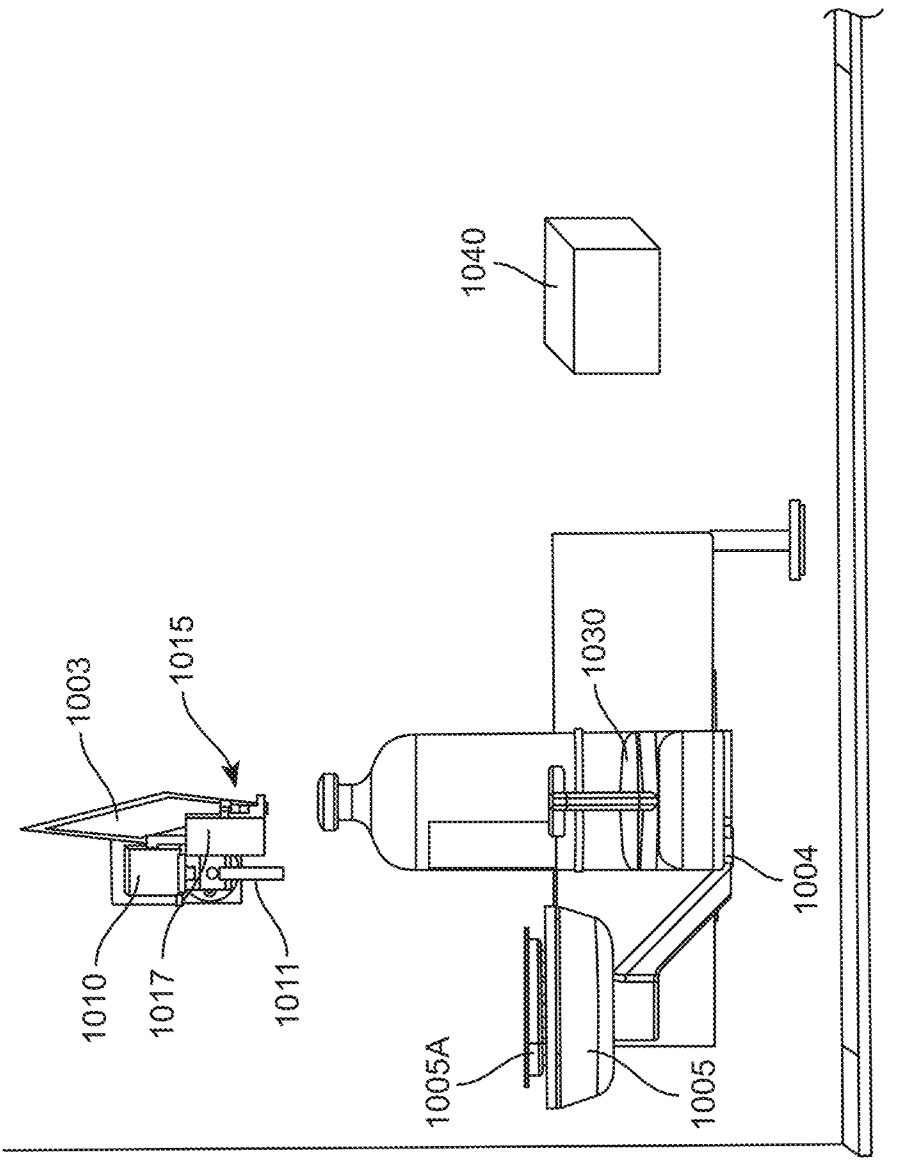
FIG. 10A
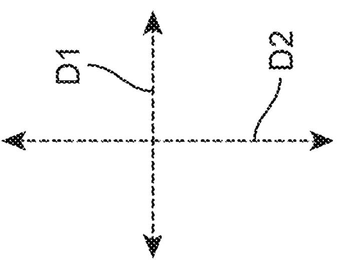

1332
1335
1334
1336
1337
1320
1333
1340
1324
CA
1312
1314
1340
1333
1336
1337
1334
1300
1332
1335
1330

AUTOMATED VIAL PREPARATION MODULE

TECHNOLOGICAL FIELD

The present application relates to an automated module for storage and/or preparation of vials, performed for example prior to pharmaceutical compounding processes.

BACKGROUND

U.S. Pat. No. 10,688,021B2 to Tribble et al. discloses "An automated medication preparation system for preparing a prescribed dosage of medication in a drug delivery device includes a plurality of stations for receiving, handling and processing the drug delivery device so that the prescribed dosage of medication is delivered to the drug delivery device and a transporting device that receives and holds more than one drug delivery device and moves the drug delivery devices in a controlled manner from one station to another station. The system is configured so that two or more separate drug delivery devices can be acted upon at the same time."

EP2465483B1 to Reinhardt et al. discloses " . . . an automated Pharmacy Admixture System (APAS) may include a manipulator (322) system to transport medical containers such as bags, vials, or syringes in a compounding chamber regulated to a pressure below atmospheric pressure. In a preferred implementation, the manipulator system is configured to grasp and convey syringes (1106), IV bags (1102), and vials (1104) of varying shapes and sizes from a storage system in an adjacent chamber regulated at a pressure above atmospheric pressure. Various embodiments may include a controller adapted to actuate the manipulator system to bring a fill port of an IV bag (1102), vial (1104), or syringe (1106) into register with a filling port at a fluid transfer station in the chamber. A preferred implementation includes a sanitization system that can substantially sanitize a bung on a fill port of a vial (1104) or IV bag in preparation for transport to the fluid transfer station."

SUMMARY

Generally, a vial needs to be prepared prior to being used for drug compounding, and the preparation can include one or more steps out of removing a cap of the vial, cleaning (disinfecting) at least the septum of the vial, and mounting a vial adaptor on the vial. Automating these steps ensures sterility of the vial during the process as well as that of the prepared vial, at least because no human intervention as well as no exposure to contamination is involved. Moreover, monitoring and controlling the preparation process by imaging and related processes ensure the adherence to the standards of quality and safety of compounded sterile drug preparations, such as USP797 and similar standards. Some or all of the preparation process described herein can be performed in a controlled (sterile and clean) environment adhering with the regulation "ISO 14644-1-Cleanrooms and associated controlled environments."

The automation, monitoring, and/or controlling the process of preparation of vials ensures that from prior to uncapping of the vial and until a vial adaptor is mounted to the vial (piercing the septum of the vial for the first time), the vial is not exposed to any contaminants. The described modules are usable for effectively disinfecting the vial and ensuring vial closure integrity (since the vial is disinfected between the cap removal and the placing of the adaptor thereon), thereby potentially extending a beyond-use-date of the vial. For instance, a beyond-use-date of a vial represents a date beyond which the vial and/or its contents cannot be used for drug compounding. The systems and methods described herein for preparation of the vials, prior to use of vials during compounding, may extend the beyond-use-date of the vials.

It is to be understood herein that the systems for preparation of vials have been interchangeably referred to herein as automated vial storage and preparation modules and automated vial preparation modules. The vials, prior to and/or after preparation can be stored within the module or externally to the module. Accordingly, a module being referred to as vial storage and preparation module is not to be understood as necessarily including a vial storage region. In fact in some examples, a module can have a vial storage region and can still be referred to as a vial preparation module.

For the purposes of the present description, drug compounding or pharmaceutical compounding can be understood as a process including, for example, transfer of drug (or other liquid) to and/or from the vial, and accordingly a system in which the drug compounding or pharmaceutical compounding is performed can be referred to herein as a pharmaceutical compounding system.

According to an aspect of some embodiments there is provided an automated vial storage and preparation module, comprising:

- vial storage which includes designated vial locations;
- vial transferring means configured for gripping and moving a vial;
- a vial cap removal tool;
- a swab manipulator for disinfecting at least a portion of the vial using a swab; and
- control circuitry configured for:
- maneuvering the vial transferring means to transfer a selected vial from its corresponding vial location in the storage to a vial mount on which the vial is received and held; and
- maneuvering the cap removal tool and the swab manipulator to engage a vial located at the vial mount to operate on the vial held thereon.

In some embodiments, the module comprises a housing in which the inner volume is filtered for maintaining clean air, at least at a portion thereof in which the vial mount is located.

In some embodiments, the vial transferring means comprise a robot arm having a gripper at a distal end thereof.

In some embodiments, the module further comprises a reservoir of disinfecting solution, and a swab stock; wherein the swab manipulator is configured to engage a swab from the swab stock; dip the swab in the reservoir; and move the swab into contact with a septum of the vial held on the vial mount.

In some embodiments, the gripper is configured for being used as the vial cap removal tool.

In some embodiments, the gripper is configured for being used as the swab manipulator.

In some embodiments, the vial storage is constructed as a plurality of drawers, and wherein the designated vial locations are formed as a matrix of slots in each of the drawers.

In some embodiments, one or more of the drawers are actively cooled.

In some embodiments, the module further comprises an imager for capturing images of the vial; wherein the control circuitry is configured to process the captured images for one or more of:

obtaining vial data;

verifying that a correct vial was loaded onto the module or that a correct vial was selected for preparation;

verifying that a disinfecting solution had been spread on at least a portion of the vial by the swab manipulator.

In some embodiments, the control circuitry is configured to instruct the transferring means to sort vials into the designated vial locations in the storage based on the captured images.

In some embodiments, the control circuitry is configured, upon receipt of an order for preparing a vial, to select a vial from storage according to an expiration date of the vial.

In some embodiments, the housing comprises at least one opening, which is normally closed, for loading of vials onto the module.

In some embodiments, the control circuitry is configured to time the transfer of loaded vials, by the transferring means, into the storage.

In some embodiments, there is provided a hood comprising:

an automated vial storage and preparation module for example as described herein, the module being at least partially contained within the hood;

an automated pharmaceutical compounding system; and transferring means for delivering a vial prepared by the module into further handling by the compounding system.

In some embodiments, the module comprises an exit platform from which the transferring means are configured to pick up the prepared vial for transferring the vial to the compounding system.

In some embodiments, the transferring means are configured to return a partially filled vial, after the vial had been used by the compounding system, into the designated location of the storage of the module.

In some embodiments, the control circuitry is configured to track or receive input from the compounding system regarding the amount of vial content used or remaining in the vial following compounding, and determine whether a partially filled vial should be returned to storage in the module.

In some embodiments, at least a portion of the module is located outside the hood such that loading of vials onto the module is external to the hood.

According to an aspect of some embodiments there is provided a vial storage and preparation module, comprising:

a housing defining a controlled inner volume, the housing comprising an opening with a spring-actuated cover normally closing the opening; and a tray comprising a horizonal surface and a vertical wall extending from the surface;

wherein the tray is slidable between at least:

a first position in which at least a portion of the surface is located externally to the housing, whereby the spring-actuated cover is pushed away from the opening while the vertical wall of the tray seals the opening of the housing, for maintaining the controlled inner volume; and a second position in which the spring-actuated cover seals the opening of the housing for maintaining the controlled inner volume; and the tray including said surface and vertical wall are fully located inside the inner volume.

In some embodiments, the controlled inner volume is a volume in which clean air conditions are maintained.

In some embodiments, in the first position of the tray, the at least a portion of the surface which is located externally to the housing is shaped and configured to receive a plurality of vials which are randomly placed thereon.

In some embodiments, the spring-actuated cover and the vertical wall of the tray are shaped and sized to fit the opening such that the opening is hermetically sealed in both the first and second positions of the tray.

In some embodiments, sliding of the tray between the first and second positions is motor actuated.

In some embodiments, the module further comprises a vial storage constructed as a plurality of drawers, each drawer having designated vial locations; and transferring means configured for picking a vial from the surface of the tray, when the tray is in the second position, and placing the vial at one of said designated vial locations in one of said drawers of the vial storage.

According to an aspect of some embodiments there is provided a vial disinfecting assembly, comprising:

a swab stock;

a swab manipulator;

a reservoir of disinfecting solution; and control circuitry configured to operate the swab manipulator to: pick up a swab from the swab stock; dip the swab in the reservoir; and transfer the swab into contact with the septum of a vial intended for disinfection.

In some embodiments, the swab manipulator is configured to move the swab across the septum.

In some embodiments, the assembly comprises a vial mount on which the vial is held when the swab manipulator brings a swab into contact with the vial.

In some embodiments, at least an upper surface of the vial mount is rotatable so as to turn the vial with respect to a swab held by the swab manipulator.

In some embodiments, the assembly further comprises an imager configured to capture images of the reservoir; wherein the control circuitry is configured to process the captured images for determining a remaining amount of disinfecting solution in the reservoir.

In some embodiments, the reservoir is constructed as a tank having a transparent wall allowing to visualize a remaining volume of the disinfecting solution.

In some embodiments, the assembly further comprises an imager configured to capture images of a vial being disinfected; wherein the control circuitry is configured to process the captured images for determining whether the disinfecting solution has been sufficiently spread on the vial septum.

In some embodiments, the imager comprises a thermal imager.

In some embodiments, the swab manipulator comprises a resilience mechanism by which a swab held by the swab manipulator is pressed against the vial septum.

In some embodiments, the control circuitry operates the swab manipulator to bring the swab into contact with the vial septum and to move the swab across the septum taking into account a height and diameter of the vial septum.

In some embodiments, the height and diameter of the vial septum are assessed from images of the vial captured by the imager.

According to an aspect of some embodiments there is provided a vial storage and preparation module, comprising:

a housing defining at least first and second adjacent portions, the first portion comprising a vial loading surface and vial storage means, and the second portion comprising automated means for transferring a vial, decapping a vial and disinfecting a vial;

wherein one or both of the following apply:

the second portion comprises air filtering means for maintaining clean air conditions, and an air flow source;

the module is configured to be used with a hood such that at least the second portion is located inside the hood and is exposed to air flow and clean air conditions of the hood.

In some embodiments, the vial storage means constitute a plurality of movable drawers which are accessible by the vial transferring means.

In some embodiments, one or more of the drawers are actively cooled.

In some embodiments, the first portion also comprises air filtering means.

According to aspect of some embodiments there is provided a method for automated storing and preparation of a drug vial, comprising:

receiving, at a vial storage and preparation module, a filled drug vial;

using automated transferring means, transferring the vial into a designated storage location in the module;

selecting the vial for preparation;

using the automated transferring means, transferring the vial to a vial mount of the module;

using a vial cap removal tool, engaging the vial at the vial mount and removing a cap of the vial; using a swab manipulator, engaging the vial at the vial mount and wiping at least a portion of the decapped vial to disinfect the vial.

In some embodiments, the automated transferring means, the vial cap removal tool and the swab manipulator are controlled by a control circuitry of the module.

In some embodiments, the method further comprises imaging the vial using one or more imagers of the module, and processing the captured images at the control circuitry for determining vial parameters.

In some embodiments, the method comprises operating the automated transferring means, the vial cap removal tool and the swab manipulator according to the vial parameters determined from the captured images.

In some embodiments, the method comprises transferring the decapped and disinfected vial out from the module and into an automated compounding system.

In some embodiments, the method further comprises automatically returning a partially used vial from the automated compounding system back into the module, and storing the partially used vial.

Below is a list of embodiments of the presently disclosed subject matter. It is to be understood herein that a vial preparation module according to an embodiment of the following list or according to any aspect of the aspects listed above, can include one or more features of a vial preparation module according to other embodiments of the following list or a vial preparation module according to other aspects of the aspects listed above.

1. An automated vial preparation module that, when in use, prepares vials for being used in pharmaceutical compounding, said preparation of vials comprising at least cleaning a septum of a vial, said vial preparation module comprising:

a vial mount having a mount top surface for placing thereon a vial to be prepared in an upright orientation;

a manipulator including a swab gripper operable to grip at least a first swab; and control circuitry configured for:

maneuvering at least one of the vial mount and the manipulator with respect to the other to position the swab gripper at least partially vertically above the vial mount; and bringing the first swab gripped by the swab gripper into direct contact with a septum of the vial placed upright on the mount top surface.

2. The automated vial preparation module according to Embodiment 1, further comprising a disinfecting solution reservoir holding unit operable to hold a disinfecting solution reservoir, wherein the control circuitry is operable for controlling the applying of disinfecting solution stored in the disinfecting solution reservoir onto the septum of the vial.

3. The automated vial preparation module according to Embodiment 2, further comprising a dropper mechanism operable to selectively drip the disinfecting solution from the disinfecting solution reservoir held at the disinfecting solution reservoir holder, and the control circuitry is operable for controlling the applying of disinfecting solution on the septum by maneuvering the dropper mechanism to drip a controlled volume of the disinfecting solution from the disinfecting solution reservoir onto the septum prior to said bringing the first swab into direct contact with the septum.

4. The automated vial preparation module according to Embodiment 2, wherein the control circuitry is operable for controlling the applying of disinfecting solution onto the septum of the vial by maneuvering the manipulator for at least partially soaking the first swab with the disinfecting solution stored in the disinfecting solution reservoir prior to said bringing the first swab into direct contact with the septum.

5. The automated vial preparation module according to Embodiment 4, wherein the control circuitry is operable for at least partially soaking the first swab with the disinfecting solution by at least partially dipping the first swab in the disinfecting solution stored in the disinfecting solution reservoir.

6. The automated vial preparation module according to any one of Embodiments 2 to 5, further comprising an imaging apparatus for imaging a field of view including at least the septum of the vial, wherein the control circuitry is operable to monitor the application of the disinfecting solution on the septum based on said imaging.

7. The automated vial preparation module according to any one of Embodiments 1 to 6, wherein the control circuitry is operable for maneuvering at least one of the vial mount and the manipulator with respect to the other to wipe the septum of the vial with the first swab.

8. The automated vial preparation module according to Embodiment 7, wherein the control circuitry is operable for maneuvering the vial mount to rotate the vial with respect to the first swab about a vial longitudinal axis for wiping the septum with the first swab.

9. The automated vial preparation module according to Embodiment 8, wherein the control circuitry is operable for maneuvering the vial mount to rotate the vial in one or more sets of repeated to and fro pivoting movements with respect to corresponding one or more neutral positions by a first predetermined angle, each neutral position corresponding to a set of repeated to and fro pivoting movement.

10. The automated vial preparation module according to Embodiment 9, said first predetermined angle being between 5 degrees and 60 degrees from the first neutral position.

11. The automated vial preparation module according to Embodiment 9 or 10, wherein the control circuitry is operable for maneuvering the vial mount to repeatedly and intermittently change the neutral position from a first neutral position of the one or more neutral positions to a second neutral position of the one or more neutral positions by turning the vial about the vial longitudinal axis by a second predetermined angle.

12. The automated vial preparation module according to Embodiment 11, said second predetermined angle being between 10 degrees and 120 degrees from the first neutral position.

13. The automated vial preparation module according to any one of Embodiments 9 to 12, wherein the control circuitry is operable for maneuvering the vial mount to rotate the vial in repeating to and fro pivoting movements for at least 3 seconds in each of the one or more sets.

14. The automated vial preparation module according to any one of Embodiments 8 to 13, wherein the first swab has a swab surface that contacts the septum, said control circuitry being operable for bringing a center of the swab surface into contact with the septum at a location offset from a center of the septum.

15. The automated vial preparation module according to any one of Embodiments 7 to 14, further comprising an imaging apparatus for imaging a field of view including at least the septum of the vial, wherein the control circuitry is operable to monitor the accuracy of wiping of the septum with the first swab, based on said imaging.

16. The automated vial preparation module according to Embodiment 15, wherein said monitoring the accuracy of wiping with the first swab comprises monitoring at least one of:

- the first predetermined angle for at least one of the one or more sets;
- the second predetermined angle for at least one of said repeated changes of the neutral position;
- duration of the pivoting in at least one of the one or more sets;
- number of repetitions of the pivoting in at least one of the one or more sets;
- total duration of the rotation; and
- contact between the septum and the first swab.

17. The automated vial preparation module according to Embodiment 16, wherein the control circuitry is operable to control said wiping the septum with the first swab based on said monitoring the accuracy of the wiping the septum with the first swab.

18. The automated vial preparation module according to any one of Embodiments 1 to 17, wherein said control circuitry is operable for maneuvering the swab gripper to grip a second swab, and for maneuvering at least one of the vial mount and the manipulator with respect to the other to position the swab gripper at least partially vertically above the vial mount, and to bring the second swab gripped by the swab gripper into direct contact with the septum of the vial and to wipe the septum with the second swab for pushing off residue from the septum.

19. The automated vial preparation module according to Embodiment 18, wherein said control circuitry is operable for moving said at least one of the vial mount and the second swab linearly with respect to the other in a lateral direction.

20. The automated vial preparation module according to Embodiment 18 or 19, wherein said control circuitry is operable for repeatedly moving said at least one of the vial mount and the second swab in linear to and fro movements with respect to the other, in a lateral direction.

21. The automated vial preparation module according to any one of Embodiments 18 to 20, wherein said control circuitry is operable for repeatedly moving said vial mount in linear to and fro movements with respect to the second swab, in a lateral direction.

22. The automated vial preparation module according to any one of Embodiments 18 to 21, further comprising an imaging apparatus for imaging a field of view including at least the septum of the vial, wherein the control circuitry is operable to monitor the accuracy of wiping the septum with the second swab, based on said imaging.

23. The automated vial preparation module according to Embodiment 22, wherein said monitoring the accuracy of wiping with the second swab comprises monitoring at least one of:

- duration of wiping;
- number of repetitions of wiping;
- presence of disinfecting solution on the septum; and
- contact between septum and the second swab.

24. The automated vial preparation module according to any one of Embodiments 1 to 23, further comprising an ultraviolet (UV) radiation source, wherein said control circuitry is operable for maneuvering at least one of the vial mount and the UV radiation source with respect to the other to expose the septum to the UV radiation.

25. The automated vial preparation module according to Embodiment 24, wherein the control circuitry is operable for monitoring and controlling at least one of wavelength and intensity of the UV radiation.

26. The automated vial preparation module according to any one of Embodiments 1 to 25, further comprising vial transferring means operable at least for picking up a vial from a vial storage region and placing the vial on the vial mount.

27. The automated vial preparation module according to Embodiment 26, wherein the vial transferring means is operable to de-cap the vial.

28. The automated vial preparation module according to Embodiment 26 or 27, wherein the vial transferring means is operable to remove a vial adaptor from a blister and mount the vial adaptor on the vial.

29. The automated vial preparation module according to Embodiment 28, further comprising an imaging apparatus for imaging a field of view including at least the vial, wherein the control circuitry is operable to monitor said mounting the vial adaptor on the vial based on said imaging.

30. The automated vial preparation module according to Embodiment 29, wherein said monitoring of mounting the vial adaptor on the vial comprises monitoring at least one of:

- alignment of the vial adaptor with respect to the vial;
- angle of the vial adaptor during mounting;
- a final position of the vial adaptor on the vial; and
- a geometry of the vial.

31. The automated vial preparation module according to Embodiment 29 or 30, wherein said monitoring the mounting of the vial adaptor on the vial comprises at least one of checking an expiry date of the vial adaptor and assessing genuineness of the vial adaptor.

32. The automated vial preparation module according to Embodiment 31, wherein the control circuitry is operable to generate an automated alert if the vial adaptor is disqualified for use.

33. The automated vial preparation module according to any one of Embodiments 28 to 32, wherein the vial inclusive of the vial adaptor is configured to maintain its integrity under a container closure integrity test (CCIT).

34. The automated vial preparation module according to any one of Embodiments 1 to 33, wherein the control circuitry is operable for labelling the vial with a time stamp indicative of a beyond use date of the vial.

35. The automated vial preparation module according to any one of Embodiments 1 to 34, further comprising a swab cartridge holder for holding a swab cartridge, said control circuitry being operable for maneuvering at least one of the swab cartridge holder and the swab gripper with respect to each other for using the swab gripper to pick up a swab from a swab cartridge held at the swab cartridge holder.

36. The automated vial preparation module according to Embodiment 35, wherein the swab cartridge holder comprises a cartridge mount onto which a swab cartridge is mountable.

37. The automated vial preparation module according to Embodiment 36, wherein the swab cartridge holder comprises a swab cartridge motor for rotating the cartridge mount.

38. The automated vial preparation module according to any one of Embodiments 1 to 37, further comprising a housing defining an inner controlled environment, said manipulator and said vial mount being positioned within the housing.

39. The automated vial preparation module according to Embodiment 38, further comprising means for delivering and directing airflow inside the housing onto the septum of the vial.

40. The automated vial preparation module according to Embodiment 39, wherein the control circuitry is operable for controlling the means for delivering the airflow at a predetermined velocity range.

41. The automated vial preparation module according to Embodiment 40, wherein the control circuitry is operable for monitoring the airflow.

42. The automated vial preparation module according to any one of Embodiments 38 to 41, further comprising one or more vial storage regions located inside the housing, for storage of one or both of pre-prepared vials and prepared vials.

43. The automated vial preparation module according to any one of Embodiments 1 to 42, wherein the direct contact between the first swab and the vial septum comprises friction-based contact for microbial reduction.

44. The automated vial preparation module according to any one of Embodiments 1 to 43, wherein the swab gripper comprises at least two swab gripping elements, wherein the control circuitry is operable for changing a distance between the at least two swab gripping elements.

45. The automated vial preparation module according to Embodiment 44, wherein the swab gripping elements extend from the manipulator in the direction of the vial mount.

46. The automated vial preparation module according to Embodiment 44 or 45, wherein the swab gripping elements are formed as rods or clamps.

47. The automated vial preparation module according to any one of Embodiments 1 to 46, further comprising an imaging apparatus for imaging a field of view including at least the vial, wherein the control circuitry is operable to identify the vial based on said imaging.

Method

48. An automated method for preparation of vials for reducing a risk of contamination, the method carried out by an automated vial preparation module comprising a vial mount and a manipulator including a swab gripper, said method comprising steps of:

- receiving, at a mount top surface of the vial mount, a vial to be prepared in an upright orientation;
- gripping, by the swab gripper of the manipulator, at least a first swab; and
- maneuvering at least one of the vial mount and the manipulator with respect to the other to position the swab gripper at least partially vertically above the vial mount, and
- bringing the first swab gripped by the swab gripper into direct contact with a septum of the vial placed upright on the mount top surface for cleaning the vial septum.

49. The automated method according to Embodiment 48, further comprising applying a disinfecting solution onto the septum of the vial.

50. The automated method according to Embodiment 49, wherein applying the disinfecting solution on the septum comprises dripping a controlled volume of the disinfecting solution from a disinfecting solution reservoir onto the septum prior to said bringing the first swab into direct contact with the septum.

51. The automated method according to Embodiment 50, wherein applying the disinfecting solution onto the septum comprises at least partially soaking the first swab with a disinfecting solution stored in a disinfecting solution reservoir prior to said bringing the first swab into direct contact with the septum.

52. The automated method according to Embodiment 51, wherein said at least partially soaking the first swab with the disinfecting solution comprises dipping the first swab in the disinfecting solution stored in the disinfecting solution reservoir.

53. The automated method according to any one of Embodiments 49 to 52, further comprising imaging a field of view including at least the septum of the vial and monitoring the application of disinfecting solution on the septum based on said imaging.

54. The automated method according to Embodiment 53, further comprising repeating the applying of disinfecting solution on the septum in response to determining, based on said monitoring, that a volume of the disinfecting solution present on the septum is insufficient.

55. The automated method according to any one of Embodiments 48 to 54, further comprising maneuvering at least one of the vial mount and the manipulator with respect to the other to wipe the septum with the first swab.

56. The automated method according to Embodiment 55, wherein said wiping the septum with the first swab comprises rotating the vial with respect to the first swab about a vial longitudinal axis.

57. The automated method according to Embodiment 56, wherein said rotating the vial comprises rotating the vial in one or more sets of repeated to and fro pivoting movements with respect to corresponding one or more neutral positions by a first predetermined angle, each neutral position corresponding to a set of repeated to and fro pivoting movement.

58. The automated method according to Embodiment 57, said first predetermined angle being between 5 degrees and 60 degrees from the first neutral position.

59. The automated method according to Embodiment 57 or 58, wherein said rotating the vial comprises repeatedly and intermittently changing the neutral position from a first neutral position of the one or more neutral positions to a second neutral position of the one or more neutral positions by turning the vial about the vial longitudinal axis by a second predetermined angle.

60. The automated method according to Embodiment 59, said second predetermined angle being between 10 degrees and 120 degrees from the first neutral position.

61. The automated method according to any one of Embodiments 57 to 60, wherein said rotating the vial comprises in each of the one or more sets repeating to and fro pivoting movements for at least 3 seconds.

62. The automated method according to any one of Embodiments 56 to 61, wherein the first swab has a swab surface that contacts the septum, said bringing the septum and the first swab into contact with each other comprises bringing a center of the swab surface into contact with the septum at a location offset from a center of the septum.

63. The automated method according to any one of Embodiments 55 to 62, further comprising, during the step of said wiping the septum with the first swab, imaging a field of view including at least the septum of the vial, and monitoring the accuracy of wiping based on said imaging.

64. The automated method according to Embodiment 63, wherein said monitoring the accuracy of wiping with the first swab comprises monitoring at least one of:

the first predetermined angle for at least one of the one or more sets;

the second predetermined angle for at least one of said repeated changes of the neutral position;

a duration of pivoting in at least one of the one or more sets;

a number of repetitions of pivoting in at least one of the one or more sets;

a total duration of pivoting; and contact between septum and the first swab.

65. The automated method according to Embodiment 64, further comprising controlling said wiping the septum with the first swab based on said monitoring.

66. The automated method according to any one of Embodiments 48 to 65, further comprising:

gripping, using the swab gripper of the manipulator, at least a second swab; and maneuvering at least one of the vial mount and the manipulator with respect to the other to position the swab gripper at least partially vertically above the vial mount, bringing the second swab gripped by the swab gripper into direct contact with the septum of the vial, and wiping the septum with the second swab for pushing off residue from the septum.

67. The automated method according to Embodiment 66, wherein wiping the septum with the second swab comprises moving said at least one of the vial and the second swab linearly with respect to the other in a lateral direction.

68. The automated method according to Embodiment 66 or 67, wherein said wiping the septum with the second swab comprises repeatedly moving said at least one of the vial and the second swab in linear to and fro movements with respect to the other, in a lateral direction.

69. The automated method according to Embodiment any one of Embodiments 66 to 68, wherein wiping the septum with the second swab comprises repeatedly moving said vial in linear to and fro movements with respect to the second swab, in a lateral direction.

70. The automated method according to any one of Embodiments 66 to 69, when dependent at least indirectly on Embodiment 2, wherein wiping the septum with the second swab comprises drying off the disinfecting solution from the septum.

71. The automated method according to any one of Embodiments 66 to 70, further comprising, after or at least partially during wiping the septum with the second swab, imaging a field of view including at least the septum of the vial and monitoring the accuracy of wiping with the second swab based on said imaging.

72. The automated method according to Embodiment 71, wherein said monitoring the accuracy of wiping with the second swab comprises monitoring at least one of:

a duration of wiping;

a number of repetitions of wiping;

presence of disinfecting solution on the septum; and contact between the septum and the second swab.

73. The automated method according to Embodiment 71 or 72, when dependent at least directly on Embodiment 70, wherein monitoring the accuracy of wiping with the second swab comprises verifying that the septum is dry and that all the disinfecting solution was either wiped off or evaporated.

74. The automated method according to any one of Embodiments 48 to 73, further comprising exposing the septum to ultraviolet (UV) radiation.

75. The automated method according to Embodiment 74, when dependent at least directly on Embodiment 26, wherein the method comprises said exposing the septum to ultraviolet (UV) radiation upon verifying that the septum is dry 76. The automated method according to Embodiment 74 or 75, further comprising monitoring and controlling at least one of wavelength and intensity of the UV radiation.

77. The automated method according to any one of Embodiments 48 to 76, further comprising mounting a vial adaptor on the vial.

78. The automated method according to Embodiment 77, when dependent at least directly on Embodiment 74, wherein the method comprises mounting the vial adaptor on the vial after said exposing the septum to ultraviolet (UV) radiation.

79. The automated method according to Embodiment 77 or 78, further comprising, during mounting the vial adaptor on the vial, imaging a field of view including at least the vial and monitoring said mounting the vial adaptor on the vial based on said imaging.

80. The automated method according to Embodiment 79, wherein said monitoring of said mounting of the vial adaptor comprises monitoring one or more of: alignment of the vial adaptor with respect to the vial, an angle of the vial adaptor during mounting, a final position of the vial adaptor on the vial, and a geometry of the vial.

81. The automated method according to Embodiment 79 or 80, wherein said monitoring of said mounting of the vial adaptor comprises at least one of checking an expiry date of the vial adaptor and assessing genuineness of the vial adaptor.

82. The automated method according to Embodiment 81, further comprising generating an automated alert if the vial adaptor is disqualified for use.

83. The automated method according to any one of Embodiments 77 to 82, wherein the vial inclusive of the vial adaptor is configured to maintain its integrity under a container closure integrity test (CCIT).

84. The automated method according to any one of Embodiments 48 to 83, further comprising labelling the vial with a time stamp indicative of a beyond use date of the vial.

85. The automated method according to any one of Embodiments 49 to 84, further comprising de-capping the vial prior to the step of said applying the disinfecting solution onto the septum of the vial.

86. The automated method according to any one of Embodiments 48 to 85, further comprising imaging a field of view including at least the vial and based on said imaging, identifying the vial.

87. The automated method according to any one of Embodiments 48 to 86, further comprising picking up a vial from a vial storage region and placing the vial on the vial mount.

88. The automated method according to any one of Embodiments 48 to 87, wherein the direct contact between the vial septum and the first swab comprises friction-based contact for microbial reduction.

89. The automated method according to any one of Embodiments 48 to 88, wherein the automated vial preparation module comprises a housing defining an inner controlled environment, said manipulator and said vial mount being positioned within the housing, wherein the method further comprises delivering and directing airflow inside the housing onto the septum of the vial.

90. The automated method according to Embodiment 89, further comprising delivering the airflow at a predetermined velocity range.

91. The automated method according to Embodiment 89 or 90, further comprising monitoring the airflow.

92. An automated vial preparation module that, when in use, prepares vials for being used in pharmaceutical compounding, said preparation of vials comprising at least cleaning a septum of a vial, said vial preparation module comprising:

a vial mount for receiving a vial to be prepared;

a disinfecting solution reservoir holder for holding a disinfecting solution reservoir;

a dropper mechanism operable to selectively drip the disinfecting solution from the disinfecting solution reservoir held at the disinfecting solution reservoir holder; and control circuitry for maneuvering the dropper mechanism for dripping a controlled volume of the disinfecting solution from the disinfecting solution reservoir held at the disinfecting solution reservoir holder onto a septum of the vial to apply the disinfecting solution on the septum.

93. The automated vial preparation module according to Embodiment 92, wherein the disinfecting solution reservoir holder comprises a reservoir gripper for, at least during said dripping, stabilizing at least an opening of the disinfecting solution reservoir via which the disinfecting solution drips from the disinfecting solution reservoir.

94. The automated vial preparation module according to Embodiment 92 or 93, wherein the dropper mechanism comprises a dropper actuator that at least selectively engages the disinfecting solution reservoir, wherein the control circuitry is operable for maneuvering the dropper actuator for dripping the controlled volume of the disinfecting solution from the disinfecting solution reservoir.

95. The automated vial preparation module according to Embodiment 94, wherein the control circuitry is operable for moving the dropper actuator with respect to the disinfecting solution reservoir for dripping the controlled volume of the disinfecting solution from the disinfecting solution reservoir.

96. The automated vial preparation module according to Embodiment 94 or 95, wherein the control circuitry is operable for maneuvering the dropper actuator to apply a controlled force on the disinfecting solution reservoir for dripping the controlled volume of the disinfecting solution from the disinfecting solution reservoir.

97. The automated vial preparation module according to any one of Embodiments 94 to 96, wherein the control circuitry is operable for maneuvering the dropper actuator to squeeze at least a part of the disinfecting solution reservoir for dripping the controlled volume of the disinfecting solution from the disinfecting solution reservoir.

98. The automated vial preparation module according to any one of Embodiments 94 to 97, wherein the control circuitry is operable for sliding the dropper actuator along at least a part of the disinfecting solution reservoir for dripping the controlled volume of the disinfecting solution from the disinfecting solution reservoir.

99. The automated vial preparation module according to any one of Embodiments 92 to 98, wherein the disinfecting solution reservoir holder removably holds the disinfecting solution reservoir.

100. The automated vial preparation module according to any one of Embodiments 92 to 99, further comprising an ultraviolet (UV) radiation source attached at least indirectly to the disinfecting solution reservoir holder, wherein the control circuitry is operable for maneuvering at least one of the vial mount and the UV radiation source for exposing the septum to the UV radiation.

101. The automated vial preparation module according to any one of Embodiments 92 to 100, further comprising a swab gripper operable to grip at least a first swab and attached at least indirectly to the disinfecting solution reservoir holder, wherein the control circuitry is operable for maneuvering at least one of the vial mount and the swab gripper for: bringing the septum and the first swab held at the swab gripper into contact with each other; and wiping the septum with the first swab, thereby frictionally engaging the first swab and the septum for reducing a risk of contaminants on the septum.

102. The automated vial preparation module according to any one of Embodiments 92 to 101, wherein the control circuitry is operable for dripping the controlled volume of the disinfecting solution at least enough to accumulate on the septum.

103. The automated vial preparation module according to Embodiment 102, wherein the control circuitry is operable for accumulating the disinfecting solution on the septum at least enough to flood the septum, such that the disinfecting solution enters a gap between the septum and a cover of the vial covering partially the septum.

104. The automated vial preparation module according to any one of Embodiments 92 to 103, wherein the control circuitry is operable for dripping at least two drops of the disinfecting solution on the septum.

105. The automated vial preparation module according to any one of Embodiments 92 to 104, further comprising an imaging apparatus for imaging a field of view including at least the vial mount and the disinfecting solution reservoir holder, wherein the control circuitry is operable for maneuvering the dropper mechanism for dripping the controlled volume of the disinfecting solution based on the images acquired by said imaging apparatus.

106. The automated vial preparation module according to Embodiment 105, wherein the control circuitry is operable for monitoring the dripped volume of the disinfecting solution based on the images acquired by said imaging apparatus.

107. The automated vial preparation module according to Embodiment 106, wherein the control circuitry is operable for maneuvering the dropper mechanism for dripping the controlled volume of the disinfecting solution based on said monitoring the dripped volume.

108. The automated vial preparation module according to any one of Embodiments 105 to 107, wherein the control circuitry is operable for monitoring a volume of the disinfecting solution remaining in the disinfecting solution reservoir based on the images acquired by said imaging apparatus.

109. An automated method for preparation of vials for reducing a risk of contamination, the method carried out by an automated vial preparation module comprising a vial mount and a disinfecting solution reservoir holder for holding a disinfecting solution reservoir, said method comprising:

receiving, at the vial mount, a vial to be prepared; and dripping, from the disinfecting solution reservoir held at the disinfecting solution reservoir holder, a controlled volume of a disinfecting solution onto a septum of the vial to apply the disinfecting solution on the septum.

110. The automated method according to Embodiment 109, wherein said dripping the controlled volume of the disinfecting solution comprises maneuvering a dropper actuator with respect to the disinfecting solution reservoir for dripping the controlled volume of the disinfecting solution from the disinfecting solution reservoir.

111. The automated method according to Embodiment 109 or 110, wherein said dripping the controlled volume of the disinfecting solution comprises dripping a high enough volume which accumulates on the septum.

112. The automated method according to Embodiment 111, wherein said dripping the controlled volume of the disinfecting solution comprises accumulating the disinfecting solution at least enough to flood the septum, such that the disinfecting solution enters a gap between the septum and a cover of the vial covering partially the septum.

113. The automated method according to any one of Embodiments 109 to 112, wherein said dripping the controlled volume of the disinfecting solution comprises dripping at least two drops of the disinfecting solution on the septum.

114. The automated method according to any one of Embodiments 109 to 113, wherein the automated vial preparation module comprises an imaging apparatus, wherein the automated method comprises:

imaging a field of view including at least the vial mount and the disinfecting solution reservoir holder; and dripping the controlled volume of the disinfecting solution based on the images acquired by said imaging apparatus.

115. The automated method according to Embodiment 114, further comprising monitoring the dripped volume of the disinfecting solution based on the images acquired by said imaging apparatus.

116. The automated method according to Embodiment 115, further comprising dripping the controlled volume of the disinfecting solution based on said monitoring the dripped volume.

117. The automated vial preparation module according to any one of Embodiments 114 to 116, further comprising monitoring a volume of the disinfecting solution remaining in the disinfecting solution reservoir based on the images acquired by said imaging apparatus.

118. The automated method according to any one of Embodiments 109 to 117, wherein the automated vial preparation module comprises an ultraviolet (UV) radiation source, wherein the automated method comprises exposing the septum to the UV radiation.

119. The automated method according to any one of Embodiments 109 to 118, wherein the automated vial preparation module comprises a swab gripper operable to grip at least a first swab, wherein the automated method comprises:

gripping the first swab at the swab gripper;

bringing the septum and the first swab into contact with each other; and wiping the septum with the first swab, thereby frictionally engaging the first swab and the septum for reducing a risk of contaminants on the septum.

120. An automated vial preparation module that, when in use, prepares vials for being used in pharmaceutical compounding, said preparation of vials comprising at least cleaning a septum of a vial, said vial preparation module comprising:

a vial mount for receiving a vial to be prepared;

a disinfecting solution reservoir holder for holding a disinfecting solution reservoir;

a manipulator including a swab gripper operable to grip a first swab; and control circuitry for:

maneuvering the manipulator for: gripping the first swab, and at least partially soaking the first swab with the disinfecting solution stored in the disinfecting solution reservoir held at the disinfecting solution reservoir holder; and maneuvering at least one of the vial mount and the manipulator for bringing the soaked first swab into contact with a septum of the vial to apply the disinfecting solution on the septum.

121. The automated vial preparation module according to Embodiment 120, wherein the first swab comprises an absorbent material.

122. The automated vial preparation module according to 120 or 121, wherein the control circuitry is operable for at least partially soaking the first swab with the disinfecting solution by at least partially dipping the first swab in the disinfecting solution stored in the disinfecting solution reservoir.

123. The automated vial preparation module according to any one of Embodiments 120 to 122, wherein the control circuitry is operable for maneuvering at least one of the vial mount and the manipulator for wiping the septum with the soaked first swab.

124. The automated vial preparation module according to any one of Embodiments 120 to 123, wherein the control circuitry is operable for maneuvering at least one of the vial mount and the manipulator for pressing the soaked first swab on the septum.

125. The automated vial preparation module according to any one of Embodiments 120 to 124, wherein the control circuitry is operable for applying at least enough volume of the disinfecting solution to accumulate on the septum.

126. The automated vial preparation module according to Embodiment 125, wherein the control circuitry is operable for accumulating the disinfecting solution on the septum at least enough to flood the septum, such that the disinfecting solution enters a gap between the septum and a cover of the vial covering partially the septum.

127. The automated vial preparation module according to any one of Embodiments 120 to 126, further comprising an imaging apparatus for imaging a field of view including at least the vial mount and the manipulator, wherein the control circuitry is operable for maneuvering said at least one of the vial mount and the manipulator based on the images acquired by said imaging apparatus.

128. The automated vial preparation module according to Embodiment 127, wherein the control circuitry is operable for monitoring a volume of the disinfecting solution on the septum based on the images acquired by said imaging apparatus.

129. The automated vial preparation module according to Embodiment 128, wherein the control circuitry is operable for determining whether the disinfecting solution has been sufficiently spread on the septum based on the images acquired by said imaging apparatus.

130. The automated vial preparation module according to Embodiment 128 or 129, wherein the control circuitry is operable for maneuvering said at least one of the vial mount and the manipulator based on said monitoring and/or said determining.

131. The automated vial preparation module according to any one of Embodiments 127 to 130, wherein the control circuitry is operable for monitoring a volume of the disinfecting solution remaining in the disinfecting solution reservoir based on the images acquired by said imaging apparatus.

132. The automated vial preparation module according to any one of Embodiments 120 to 131, further comprising an ultraviolet (UV) radiation source attached at least indirectly to the disinfecting solution reservoir holder, wherein the control circuitry is operable for maneuvering at least one of the vial mount and the UV radiation source for exposing the septum to the UV radiation.

133. An automated method for preparation of vials for reducing a risk of contamination by an automated vial preparation module comprising a vial mount, a disinfecting solution reservoir holder for holding a disinfecting solution reservoir, and a manipulator including a swab gripper, said method comprising steps of:

receiving, at the vial mount, a vial to be prepared;

maneuvering the manipulator for: gripping the first swab, and at least partially soaking the first swab with the disinfecting solution stored in the disinfecting solution reservoir held at the disinfecting solution reservoir holder; and maneuvering at least one of the vial mount and the manipulator for bringing the soaked first swab into contact with a septum of the vial to apply the disinfecting solution on the septum.

134. The automated method according to Embodiment 133, wherein the first swab comprises an absorbent material.

135. The automated method according to Embodiment 133 or 134, wherein said at least partially soaking the first swab with the disinfecting solution comprises at least partially dipping the first swab in the disinfecting solution stored in the disinfecting solution reservoir.

136. The automated method according to any one of Embodiments 133 to 135, further comprising maneuvering at least one of the vial mount and the manipulator for wiping the septum with the soaked first swab.

137. The automated method according to any one of Embodiments 133 to 136, further comprising maneuvering at least one of the vial mount and the manipulator for pressing the soaked first swab on the septum.

138. The automated method according to any one of Embodiments 133 to 137, further comprising applying at least enough volume of the disinfecting solution to accumulate on the septum.

139. The automated method according to Embodiment 138, further comprising accumulating the disinfecting solution on the septum at least enough to flood the septum, such that the disinfecting solution enters a gap between the septum and a cover of the vial covering partially the septum.

140. The automated method according to any one of Embodiments 133 to 139, wherein the automated vial preparation module comprises an imaging apparatus, wherein the automated method comprises:

imaging a field of view including at least the vial mount and the manipulator; and maneuvering said at least one of the vial mount and the manipulator based on the images acquired by said imaging apparatus.

141. The automated method according to Embodiment 140, further comprising monitoring a volume of the disinfecting solution on the septum based on the images acquired by said imaging apparatus.

142. The automated method according to Embodiment 141, further comprising determining whether the disinfecting solution has been sufficiently spread on the septum based on the images acquired by said imaging apparatus.

143. The automated method according to Embodiment 141 or 142, further comprising maneuvering said at least one of the vial mount and the manipulator based on said monitoring and/or said determining.

144. The automated method according to any one of Embodiments 140 to 143, further comprising monitoring a volume of the disinfecting solution remaining in the disinfecting solution reservoir based on the images acquired by said imaging apparatus.

145. The automated method according to any one of Embodiments 133 to 144, wherein the automated vial preparation module comprises an ultraviolet (UV) radiation source, wherein the automated method comprises maneuvering at least one of the vial mount and the UV radiation source for exposing the septum to the UV radiation.

146. An automated vial preparation module that, when in use, prepares vials for being used in pharmaceutical compounding, said preparation of vials comprising at least cleaning a septum of a vial, said vial preparation module comprising:

a vial mount for receiving a vial to be prepared;

a vial cap removal tool for removing a vial cap of the vial;

a manipulator including a swab gripper operable to grip at least a first swab; and control circuitry for maneuvering: the vial cap removal tool and removing the vial cap from the vial received at the vial mount, and at least one of the vial mount and the manipulator for bringing the first swab gripped by the swab gripper into direct contact with a septum of the decapped vial and wiping at least a portion of the septum with the first swab to disinfect the septum of the decapped vial received at the vial mount.

147. The automated vial preparation module according to Embodiment 146, further comprising an imaging apparatus for imaging a field of view including at least the vial mount, the vial cap removal tool, and the manipulator, wherein the control circuitry is operable for maneuvering at least one of the vial mount, the vial cap removal tool, and the manipulator based on the images acquired by said imaging apparatus.

148. The automated vial preparation module according to Embodiment 147, wherein the control circuitry is operable for identifying the vial based on the images acquired by said imaging apparatus, and based on said identification, monitoring and controlling the maneuvering of at least one of the vial mount, the vial cap removal tool, and the manipulator.

149. The automated vial preparation module according to Embodiment 148, wherein the control circuitry is operable for determining one or more vial parameters based on said identifying the vial, and based on said determining, monitoring and controlling the maneuvering of at least one of the vial mount, the vial cap removal tool, and the manipulator.

150. The automated vial preparation module according to Embodiment 149, wherein the one or more vial parameters include a height of the vial.

151. An automated method for preparation of vials for reducing a risk of contamination by an automated vial preparation module that, when in use, prepares vials for being used in pharmaceutical compounding, said preparation of vials comprising at least cleaning a septum of a vial, said automated vial preparation module comprising a vial mount, a vial cap removal tool, and a manipulator including a swab gripper, said method comprising steps of:

receiving, at the vial mount, a vial to be prepared;

maneuvering the vial cap removal tool and removing the vial cap from the vial received at the vial mount; and maneuvering at least one of the vial mount and the manipulator for: gripping, by the swab gripper, at least a first swab, and bringing the first swab into direct contact with a septum of the decapped vial and wiping at least a portion of the septum with the first swab to disinfect the septum of the decapped vial received at the vial mount.

152. The automated method according to Embodiment 151, wherein the automated vial preparation module comprises an imaging apparatus, wherein the automated method comprises:

imaging a field of view including at least the vial mount, the vial cap removal tool, and the manipulator; and maneuvering at least one of the vial mount, the vial cap removal tool, and the manipulator based on the images acquired by said imaging apparatus.

153. The automated method according to Embodiment 152, further comprising identifying the vial based on the images acquired by said imaging apparatus, and based on said identification, monitoring and controlling the maneuvering of at least one of the vial mount, the vial cap removal tool, and the manipulator.

154. The automated method according to Embodiment 153, further comprising determining one or more vial parameters based on said identifying the vial, and based on said determining, monitoring and controlling the maneuvering of at least one of the vial mount, the vial cap removal tool, and the manipulator.

155. The automated method according to Embodiment 154, wherein the one or more vial parameters include a height of the vial.

156. An automated vial preparation module that, when in use, prepares vials for being used in pharmaceutical compounding, said preparation of vials comprising at least cleaning a septum of a vial, said vial preparation module comprising:

a vial mount for receiving a vial to be prepared, said vial mount being moveable along a first linear axis;

a manipulator moveable along a second linear axis transverse the first linear axis, the manipulator including a swab gripper operable to grip at least a first swab; and control circuitry for moving at least one of the vial mount along the first linear axis and the manipulator along the second linear axis for bringing a septum of a vial received at the vial mount into contact interface with a first swab gripped by the swab gripper of the manipulator.

157. The automated vial preparation module according to Embodiment 156, wherein the first linear axis extends along a width of the automated vial preparation module, and the second linear axis extends along a height of the automated vial preparation module.

158. The automated vial preparation module according to Embodiment 156 or 157, further comprising a mounting base moveable along the first linear axis, said vial mount being mounted at least indirectly at the mounting base and being moveable along the first linear axis together therewith, wherein the control circuitry is operable for moving the mounting base to a mounting base first position along the first axis, in which the vial mount is at least partially vertically aligned with the swab gripper.

159. The automated vial preparation module according to Embodiment 158, wherein the control circuitry is operable for moving the manipulator between a manipulator raised position along the second axis and a manipulator first lowered position along the second axis, corresponding to the mounting base first position along the first axis.

160. The automated vial preparation module according to Embodiment 158 or 159, further comprising a swab cartridge holder for holding a swab cartridge, mounted at least indirectly at the mounting base, wherein the control circuitry is operable for moving the mounting base to a mounting base second position along the first axis, in which the swab cartridge holder is at least partially vertically aligned with the swab gripper.

161. The automated vial preparation module according to Embodiment 160, when dependent at least indirectly on Embodiment 4, wherein the control circuitry is operable for moving the manipulator between the manipulator raised position and a manipulator second lowered position along the second axis, corresponding to the mounting base second position along the first axis.

162. The automated vial preparation module according to Embodiment 160 or 161, further comprising a disinfecting solution reservoir holder for holding a disinfecting solution reservoir, wherein the control circuitry is operable for moving the mounting base to a mounting base third position along the first axis, in which the vial mount is at least partially vertically aligned with the disinfecting solution reservoir holder.

163. The automated vial preparation module according to Embodiment 162, wherein the disinfecting solution reservoir holder is attached at least indirectly to the manipulator.

164. The automated vial preparation module according to Embodiment 162, when dependent at least indirectly on Embodiment 161, wherein the control circuitry is operable for moving the manipulator between the manipulator raised position and a manipulator third lowered position along the second axis, corresponding to the mounting base third position along the first axis.

165. The automated vial preparation module according to any one of Embodiments 162 to 164, further comprising an ultraviolet (UV) radiation source, wherein the control circuitry is operable for moving the mounting base to a mounting base fourth position along the first axis, in which the vial mount is at least partially vertically aligned with the UV radiation source.

166. The automated vial preparation module according to Embodiment 165, wherein the UV radiation source is attached at least indirectly to the manipulator.

167. The automated vial preparation module according to any one of Embodiments 156 to 166, further comprising an imaging apparatus for imaging a field of view including at least the manipulator and the vial mount, wherein the control circuitry is operable for monitoring and controlling the movement of said at least one of the vial mount and the manipulator based on the images acquired by said imaging apparatus.

168. The automated vial preparation module according to Embodiment 167, wherein the control circuitry is operable for identifying the vial based on the images acquired by said imaging apparatus, and based on said identification, monitoring and controlling the movement of said at least one of the vial mount and the manipulator.

169. The automated vial preparation module according to Embodiment 167 or 168, wherein the control circuitry is operable for monitoring the position of at least one of the vial mount and the manipulator based on the images acquired by said imaging apparatus.

170. An automated method for preparation of vials for reducing a risk of contamination by an automated vial preparation module that, when in use, prepares vials for being used in pharmaceutical compounding, said preparation of vials comprising at least cleaning a septum of a vial, said automated vial preparation module comprising a vial mount moveable along a first linear axis, and a manipulator including a swab gripper and moveable along a second linear axis transverse the first linear axis, said method comprising steps of:

receiving, at the vial mount, a vial to be prepared;

gripping, by the swab gripper of the manipulator, at least a first swab; and moving at least one of the vial mount along the first linear axis and the manipulator along the second linear axis for bringing a septum of the vial received at the vial mount into contact interface with the first swab gripped by the swab gripper.

171. The automated method according to Embodiment 170, wherein the first linear axis extends along a width of the automated vial preparation module, and the second linear axis extends along a height of the automated vial preparation module.

172. The automated method according to Embodiment 170 or 171, wherein the automated vial preparation module comprises a mounting base moveable along the first linear axis, said vial mount being mounted at least indirectly at the mounting base and being moveable along the first linear axis together therewith, wherein said moving at least one of the vial mount and the manipulator comprises moving the mounting base to a mounting base first position along the first axis, in which the vial mount is at least partially vertically aligned with the swab gripper.

173. The automated method according to Embodiment 172, wherein said moving at least one of the vial mount and the manipulator comprises moving the manipulator between a manipulator raised position along the second axis and a manipulator first lowered position along the second axis, corresponding to the mounting base first position along the first axis.

174. The automated method according to Embodiment 172 or 173, wherein the automated vial preparation module comprises a swab cartridge holder for holding a swab cartridge, mounted at least indirectly at the mounting base, wherein the method further comprises moving the mounting base to a mounting base second position along the first axis, in which the swab cartridge holder is at least partially vertically aligned with the swab gripper.

175. The automated method according to Embodiment 174, when dependent at least indirectly on Embodiment 173, further comprising moving the manipulator between the manipulator raised position and a manipulator second lowered position along the second axis, corresponding to the mounting base second position along the first axis.

176. The automated method according to Embodiment 174 or 175, wherein the automated vial preparation module comprises a disinfecting solution reservoir holder for holding a disinfecting solution reservoir, wherein the method further comprises moving the mounting base to a mounting base third position along the first axis, in which the vial mount is at least partially vertically aligned with the disinfecting solution reservoir holder.

177. The automated method according to Embodiment 176, wherein the disinfecting solution reservoir holder is attached at least indirectly to the manipulator.

178. The automated method according to Embodiment 177, when dependent at least indirectly on Embodiment 6, further comprising moving the manipulator between the manipulator raised position and a manipulator third lowered position along the second axis, corresponding to the mounting base third position along the first axis.

179. The automated method according to any one of Embodiments 176 to 178, wherein the automated vial preparation module comprises an ultraviolet (UV) radiation source, wherein the method further comprises moving the mounting base to a mounting base fourth position along the first axis, in which the vial mount is at least partially vertically aligned with the UV radiation source.

180. The automated method according to Embodiment 179, wherein the UV radiation source is attached at least indirectly to the manipulator.

181. The automated method according to any one of Embodiments 170 to 180, wherein the automated vial preparation module comprises an imaging apparatus, wherein the method comprises: imaging by the imaging apparatus a field of view including at least the manipulator and the vial mount; and monitoring and controlling the movement of said at least one of the vial mount and the manipulator based on the images acquired by said imaging apparatus.

182. The automated method according to Embodiment 181, further comprising identifying the vial based on the images acquired by said imaging apparatus, and based on said identification, monitoring and controlling the movement of said at least one of the vial mount and the manipulator.

183. The automated method according to Embodiment 181 or 182, further comprising monitoring the position of at least one of the vial mount and the manipulator based on the images acquired by said imaging apparatus.

184. An automated vial preparation module that, when in use, prepares vials for being used in pharmaceutical compounding, said preparation of vials comprising at least cleaning a septum of a vial, said vial preparation module comprising:

a vial preparation zone in which the automated vial preparation module performs the preparation of the vial;

at least one imaging apparatus for imaging a field of view including the vial preparation zone; and control circuitry for:

receiving the images acquired by the at least one imaging apparatus;

processing the acquired images; and monitoring, based on said processing, at least the cleaning of the septum of the vial.

185. The automated vial preparation module according to Embodiment 184, wherein said cleaning of the septum of the vial includes applying a disinfecting solution on a septum of the vial.

186 The automated vial preparation module according to Embodiment 185, wherein the control circuitry is operable to monitor one or more disinfecting solution related indications based on the images.

187. The automated vial preparation module according to Embodiment 186, wherein the one or more disinfecting solution related indications comprises at least one of:

volume of the disinfecting solution on the septum of the vial, whether the septum is wet or dry, and whether the volume of the disinfecting solution on the septum is sufficient or not.

188. The automated vial preparation module according to Embodiment 186 or 187, wherein the automated vial preparation module performs the cleaning of the septum of the vial based on a real-time feedback according to said monitoring of the one or more disinfecting solution related indications.

189. The automated vial preparation module according to any one of Embodiments 184 to 188, wherein said cleaning of the septum of the vial includes wiping the septum of the vial by at least one swab.

190. The automated vial preparation module according to Embodiment 189, wherein the control circuitry is operable to monitor one or more swab related indications based on the images.

191. The automated vial preparation module according to Embodiment 190, wherein the one or more swab related indications comprises at least one of:

pattern of the movement of the swab on the septum,
duration of the wiping,
accuracy of the wiping,
contact between the swab and the septum,
pressure applied by the swab on the septum,
position of the swab,
relative position of the swab and the septum during the wiping,
whether the swab is wet or dry,
orientation of the swab with respect to the septum, and
time of initiation of the wiping.

192. The automated vial preparation module according to Embodiment 190 or 191, wherein the automated vial preparation module performs the cleaning of the septum of the vial based on a real-time feedback according to said monitoring of the one or more swab related indications.

193. The automated vial preparation module according to any one of Embodiments 184 to 192, wherein said preparation of the vial includes mounting a vial adaptor on the vial.

194. The automated vial preparation module according to Embodiment 193, wherein the control circuitry is operable to monitor one or more vial adaptor related indications based on the images.

195. The automated vial preparation module according to Embodiment 194, wherein the one or more vial adaptor related indications comprises at least one of:

alignment of the vial adaptor with respect to the vial,
angle of the vial adaptor with respect to the vial,
final position of the vial adaptor on the vial,
expiry date of the vial adaptor, and
determining whether the vial adaptor is genuine or not.

196. The automated vial preparation module according to Embodiment 194 or 195, wherein the automated vial preparation module performs the preparation of the vial based on a real-time feedback according to said monitoring of the one or more vial adaptor related indications.

197. The automated vial preparation module according to any one of Embodiments 184 to 196, wherein said preparation of the vial includes placing the vial on a vial mount.

198. The automated vial preparation module according to Embodiment 197, wherein the control circuitry is operable to monitor one or more vial related indications based on the images.

199. The automated vial preparation module according to Embodiment 198, wherein the one or more vial related indications comprises at least one of:

alignment of the vial with respect to the vial mount,
orientation of the vial on the vial mount,
position of the septum of the vial,
position of the vial with respect to the vial mount,
position of the vial on the vial mount,
identification of a label of the vial,
height of the vial,
geometry of the vial,
content of the vial,
movement of the vial and/or the vial mount, and
disinfection of the septum of the vial.

200. The automated vial preparation module according to Embodiment 198 or 199, wherein the automated vial preparation module performs the preparation of the vial based on a real-time feedback according to said monitoring of the one or more vial related indications.

201. The automated vial preparation module according to any one of Embodiments 184 to 200, wherein said cleaning the septum of the vial includes exposing the septum to an ultraviolet (UV) radiation.

202. The automated vial preparation module according to Embodiment 201, wherein the control circuitry is operable to monitor one or more UV related indications.

203. The automated vial preparation module according to Embodiment 202, wherein the one or more UV related indications comprises at least one of:

wavelength of the UV radiation,
intensity of the UV radiation,
duration of the exposure,
angle of the exposure, and
distance between the septum and source of the UV radiation.

204. The automated vial preparation module according to Embodiment 202 or 203, wherein the automated vial preparation module performs the preparation of the vial based on a real-time feedback according to said monitoring of the one or more UV related indications.

205. The automated vial preparation module according to any one of Embodiments 184 to 204, wherein said preparation of the vial includes delivering and directing an airflow on the vial.

206. The automated vial preparation module according to Embodiment 205, wherein the control circuitry is operable to monitor one or more airflow related indications.

207. The automated vial preparation module according to Embodiment 206, wherein the one or more airflow related indications comprises at least one of:

laminarity of the airflow,
first air contact of the airflow at the vial and/or vial adaptor,
velocity of the airflow,
direction of the airflow,
presence of the airflow, and
airflow path.

208. The automated vial preparation module according to Embodiment 206 or 207, wherein the automated vial preparation module performs the preparation of the vial based on a real-time feedback according to said monitoring of the one or more airflow related indications.

209. An automated method for preparation of vials for reducing a risk of contamination by an automated vial preparation module that, when in use, prepares vials for being used in pharmaceutical compounding, said preparation of vials comprising at least cleaning a septum of a vial, said method comprising steps of:

operating the automated vial preparation module for preparing the vial;

imaging, by an imaging apparatus, a field of view including a vial preparation zone in which the cleaning of the septum of the vial is performed; and monitoring based on the images at least the cleaning of the septum of the vial.

210. The automated method according to Embodiment 209, wherein said cleaning of the septum of the vial includes applying a disinfecting solution on a septum of the vial.

211. The automated method according to Embodiment 210, further comprises monitoring one or more disinfecting solution related indications based on the images.

212. The automated method according to Embodiment 211, wherein the one or more disinfecting solution related indications comprises at least one of:

volume of the disinfecting solution on the septum of the vial, whether the septum is wet or dry, and whether the volume of the disinfecting solution on the septum is sufficient or not.

213. The automated method according to Embodiment 211 or 212, wherein said operating the automated vial preparation module for preparing the vial comprises operating the automated vial preparation module based on a real-time feedback according to said monitoring of the one or more disinfecting solution related indications.

214. The automated method according to any one of Embodiments 209 to 213, wherein said cleaning of the septum of the vial includes wiping the septum of the vial by at least one swab.

215. The automated method according to Embodiment 214, further comprises monitoring one or more swab related indications based on the images.

216. The automated method according to Embodiment 215, wherein the one or more swab related indications comprises at least one of:

pattern of the movement of the swab on the septum, duration of the wiping, accuracy of the wiping, contact between the swab and the septum, pressure applied by the swab on the septum, position of the swab, relative position of the swab and the septum during the wiping, whether the swab is wet or dry, orientation of the swab with respect to the septum, and time of initiation of the wiping.

217. The automated method according to Embodiment 215 or 216, wherein said operating the automated vial preparation module for preparing the vial comprises operating the automated vial preparation module based on a real-time feedback according to said monitoring of the one or more swab related indications.

218. The automated method according to any one of Embodiments 209 to 217, wherein said preparation of the vial includes mounting a vial adaptor on the vial.

219. The automated method according to Embodiment 218, further comprises monitoring one or more vial adaptor related indications based on the images.

220. The automated method according to Embodiment 219, wherein the one or more vial adaptor related indications comprises at least one of:

alignment of the vial adaptor with respect to the vial, angle of the vial adaptor with respect to the vial, final position of the vial adaptor on the vial, expiry date of the vial adaptor, and determining whether the vial adaptor is genuine or not.

221. The automated method according to Embodiment 219 or 220, wherein said operating the automated vial preparation module for preparing the vial comprises operating the automated vial preparation module based on a real-time feedback according to said monitoring of the one or more vial adaptor related indications.

222. The automated method according to any one of Embodiments 209 to 221, wherein said preparation of the vial includes placing the vial on a vial mount.

223. The automated method according to Embodiment 222, further comprising monitoring one or more vial related indications based on the images.

224. The automated method according to Embodiment 223, wherein the one or more vial related indications comprises at least one of:

alignment of the vial with respect to the vial mount, orientation of the vial on the vial mount, position of the septum of the vial, position of the vial with respect to the vial mount, position of the vial on the vial mount, identification of a label of the vial, height of the vial, geometry of the vial, content of the vial, movement of the vial and/or the vial mount, and disinfection of the septum of the vial.

225. The automated method according to Embodiment 223 or 224, wherein said operating the automated vial preparation module for preparing the vial comprises operating the automated vial preparation module based on a real-time feedback according to said monitoring of the one or more vial related indications.

226. The automated method according to any one of Embodiments 209 to 225, wherein said cleaning the septum of the vial includes exposing the septum to an ultraviolet (UV) radiation.

227. The automated method according to Embodiment 226, further comprising monitoring one or more UV related indications.

228. The automated method according to Embodiment 227, wherein the one or more UV related indications comprises at least one of:

wavelength of the UV radiation, intensity of the UV radiation, duration of the exposure, angle of the exposure, and distance between the septum and source of the UV radiation.

229. The automated method according to Embodiment 227 or 228, wherein said operating the automated vial preparation module for preparing the vial comprises operating the automated vial preparation module based on a real-time feedback according to said monitoring of the one or more UV related indications.

230. The automated method according to any one of Embodiments 209 to 229, wherein said preparation of the vial includes delivering and directing an airflow on the vial.

231. The automated method according to Embodiment 230, further comprising monitoring one or more airflow related indications.

232. The automated method according to Embodiment 231, wherein the one or more airflow related indications comprises at least one of:

laminarity of the airflow, first air contact of the airflow at the vial and/or vial adaptor, velocity of the airflow, direction of the airflow,
presence of the airflow, and
airflow path.

233. The automated method according to Embodiment 231 or 232, wherein said operating the automated vial preparation module for preparing the vial comprises operating the automated vial preparation module based on a real-time feedback according to said monitoring of the one or more airflow related indications.

234. An automated vial preparation and drug compounding arrangement comprising:

an automated vial preparation module that, when in use, prepares vials for being used in pharmaceutical compounding, said preparation of vials comprising at least cleaning a septum of a vial;

an automated pharmaceutical compounding system that, when in use, performs drug compounding;

transferring means for transferring a vial prepared by the automated vial preparation module at least from the automated vial preparation module to the automated pharmaceutical compounding system for further handling by the automated pharmaceutical compounding system; and control circuitry for maneuvering the transferring means to transfer the vial.

235. The automated vial preparation and drug compounding arrangement according to Embodiment 234, further comprising a first hood including a controlled inner volume in which clean air conditions are maintained.

236. The automated vial preparation and drug compounding arrangement according to Embodiment 235, wherein the automated vial preparation module and the automated pharmaceutical compounding system are positioned within the first hood.

237. The automated vial preparation and drug compounding arrangement according to Embodiment 235, further comprising a second hood including a controlled inner volume in which clean air conditions are maintained.

238. The automated vial preparation and drug compounding arrangement according to Embodiment 237, wherein the automated vial preparation module is positioned within the first hood and the automated pharmaceutical compounding system is positioned within the second hood.

239. The automated vial preparation and drug compounding arrangement according to any one of Embodiments 234 to 238, wherein the automated vial preparation module comprises an exit platform from which the transferring means is configured to pick up the prepared vial for transferring the prepared vial to the automated pharmaceutical compounding system.

240. The automated vial preparation and drug compounding arrangement according to any one of Embodiments 234 to 239, further comprising control circuitry configured to determine the amount of vial content used or remaining in the prepared vial after the use of the prepared vial by the automated pharmaceutical compounding system, and based thereupon determine whether the prepared vial is to be returned to the automated vial preparation module.

241. The automated vial preparation and drug compounding arrangement according to any one of Embodiments 234 to 240, wherein the transferring means is configured to transfer the prepared vial, after the use of the prepared vial by the automated pharmaceutical compounding system, from the automated pharmaceutical compounding system to the automated vial preparation module.

242. The automated vial preparation and drug compounding arrangement according to any one of Embodiments 234 to 241, wherein the automated vial preparation module comprises a vial storage for storing pre-prepared vials and/or prepared vials.

243. The automated vial preparation and drug compounding arrangement according to Embodiment 242, wherein the transferring means is configured to transfer the pre-prepared vials and/or prepared vials from and/or to the vial storage.

244. The automated vial preparation and drug compounding arrangement according to any one of Embodiments 234 to 243, wherein the drug compounding comprises at least one of dilution of the prepared vial, reconstitution of the prepared vial, transfer of drug to and/or from the prepared vial, and agitating the prepared vial.

245. The automated vial preparation and drug compounding arrangement according to any one of Embodiments 234 to 244, wherein the automated pharmaceutical compounding system comprises a dilution module operable for performing said drug compounding including at least one of dilution of the prepared vial and reconstitution of the prepared vial.

246. The automated vial preparation and drug compounding arrangement according to any one of Embodiments 234 to 245, wherein the automated pharmaceutical compounding system comprises a shaking module operable for performing said drug compounding including agitating the prepared vial.

247. The automated vial preparation and drug compounding arrangement according to any one of Embodiments 234 to 246, wherein the automated vial preparation module is an automated vial preparation module according to any one of Embodiments 1 to 47 or Embodiments 92 to 108 or Embodiments 120 to 132 or Embodiments 146 to 150 or Embodiments 156 to 169 or Embodiments 184 to 207.

248. A vial mount comprising:

a mount top portion including a mount top surface for positioning of a vial thereon;

a mount bottom portion;

a first rotary arrangement that is operatively associated with the mount top portion and rotates at least the mount top surface about a central axis; and a second rotary arrangement that is operatively associated with the mount bottom portion and rotates at least the mount bottom portion about the central axis.

249. The vial mount according to Embodiment 248, further comprising a vial gripper displaceable between a grip state in which the vial gripper grips the vial when the vial is positioned on the mount top surface, and a release state in which the vial gripper releases the vial.

250. The vial mount according to Embodiment 249, said vial gripper comprising at least two gripping portions positioned on opposite sides of the central axis, said gripping portions being a gripping distance apart from each other at the grip state and a release distance, greater than the gripping distance, apart from each other at the release state.

251. The vial mount according to Embodiment 250, wherein the gripping portions are equidistant from the central axis at least at the grip state to centralize the vial on the mount top surface.

252. The vial mount according to Embodiment 250 or 251, wherein the vial gripper comprises at least two arms positioned on opposite sides of the central axis, each of said arms comprising: a respective connection end connected to the mount bottom portion, a respective gripping end constituting a respective one of the gripping portions, and a respective extension portion extending between the respective connection end and the respective gripping end at least partially along a direction extending between the mount top portion and the mount bottom portion.

253. The vial mount according to any one of Embodiments 250 to 252, wherein the gripping portions are positioned beyond the mount top surface in a direction from the mount bottom portion towards the mount top portion.

254. The vial mount according to any one of Embodiments 250 to 253, wherein at the grip state, each of the gripping portions engages the vial.

255. The vial mount according to any one of Embodiments 250 to 254, wherein each of the gripping portions comprise at least two vial engaging regions spaced apart from each other, wherein at the grip state, each of the at least two vial engaging regions engages the vial.

256. The vial mount according to any one of Embodiments 250 to 255, wherein the vial mount comprises a vial gripper actuation mechanism that moves at least one of the gripping portions for the gripping portions to be selectively at the gripping distance apart from each other and the release distance apart from each other.

257. The vial mount according to Embodiment 256, wherein the vial gripper actuation mechanism moves at least one of the gripping portions to displace the vial gripper between the grip sate and the release state.

258. The vial mount according to Embodiment 256 or 257, when dependent at least indirectly on Embodiment 252, wherein the vial gripper actuation mechanism is operatively associated with at least one of the arms and moves said at least one arm with respect to the other to displace the vial gripper between the grip sate and the release state.

259. The vial mount according to any one of Embodiments 248 to 258, wherein the first rotary arrangement rotates the mount top surface about the central axis independently of the mount bottom portion.

260. The vial mount according to any one of Embodiments 248 to 259, wherein the second rotary arrangement rotates the mount bottom portion about the central axis independently of the mount top surface.

261. The vial mount according to any one of Embodiments 248 to 259, wherein the second rotary arrangement rotates the mount bottom portion about the central axis together with the mount top surface.

262. The vial mount according to any one of Embodiments 248 to 261, wherein the first rotary arrangement comprises a first motor.

263. The vial mount according to Embodiment 262, wherein the second rotary arrangement comprises a second motor.

264. The vial mount according to Embodiment 263, wherein the second motor has a higher maximum torque than that of the first motor.

265. The vial mount according to any one of Embodiments 248 to 264, wherein the first rotary arrangement rotates the mount top surface about the central axis selectively in clockwise direction and counter-clockwise direction.

256. The vial mount according to any one of Embodiments 248 to 265, wherein the second rotary arrangement rotates the mount bottom portion about the central axis selectively in clockwise direction and counter-clockwise direction.

267. The vial mount according to any one of Embodiments 248 to 266, wherein the first rotary arrangement rotates the mount top surface about the central axis selectively at different speeds.

268. The vial mount according to any one of Embodiments 248 to 267, wherein the second rotary arrangement rotates the mount bottom portion about the central axis selectively at different speeds.

269. The vial mount according to Embodiment 252 or any one of Embodiments 253 to 268, when dependent at least indirectly on Embodiment 252, wherein a dimension of the extension portions along the direction extending between the mount top portion and the mount bottom portion is adjustable.

270. A swab cartridge comprising:

a cartridge housing formed with a plurality of swab stabilizing locations; and a plurality of swabs corresponding to the plurality of swab stabilizing locations, each of the plurality of swabs stabilized at a corresponding one of the plurality of swab stabilizing locations independently of adjacent swabs.

271. The swab cartridge according to Embodiment 270, wherein each of the plurality of swabs comprises a swab stabilizing portion held at the cartridge housing for stabilizing the swab, and a swab grippable portion protruding from the swab stabilizing portion and grippable by a swab gripper.

272. The swab cartridge according to Embodiment 271, wherein the swab grippable portion of each of the plurality of swabs is at least partially spaced apart from the swab grippable portions of the adjacent swabs.

273. The swab cartridge according to any one of Embodiments 270 to 272, wherein each of the plurality of swabs is spaced apart from the adjacent swabs.

274. The swab cartridge according to any one of Embodiments 270 to 273, wherein each of the plurality of swab stabilizing locations comprises an opening, wherein each of the plurality of swabs is partially received within the corresponding opening.

275. The swab cartridge according to Embodiment 274, when dependent on Embodiment 271, wherein the swab stabilizing portion is received within the corresponding opening in a swab insertion direction, and the swab grippable portion protrudes from the opening in the swab insertion direction.

276. The swab cartridge according to Embodiment 275, wherein the swab stabilizing portion has a swab cross-sectional area perpendicular to the swab insertion direction and a rim of the opening has an opening cross-sectional area perpendicular to the swab insertion direction, wherein the swab cross-sectional area is larger than the opening cross-sectional area.

277. The swab cartridge according to Embodiment 275 or 276, wherein the swab stabilizing portion has a circular swab cross-section taken perpendicular to the swab insertion direction, and a rim of the opening has a circular opening cross-section taken perpendicular to the swab insertion direction, wherein a diameter of the circular swab cross-section is longer than a diameter of the circular opening cross-section.

278. The swab cartridge according to any one of Embodiments 270 to 277, wherein each of the plurality of swabs is removable from the corresponding swab stabilizing location upon application of a removing force of magnitude greater than a threshold force.

279. The swab cartridge according to any one of Embodiments 270 to 278, wherein the swab stabilizing locations are arranged in one or more circles.

280. The swab cartridge according to any one of Embodiments 270 to 279, wherein the swab stabilizing locations are arranged in a plurality of concentric circles.

281. The swab cartridge according to any one of Embodiments 270 to 280, wherein each of the swab stabilizing locations is spaced from the adjacent swab stabilizing location by at least 1 mm.

282. The swab cartridge according to any one of Embodiments 270 to 281, wherein each of the swabs is made of a nonwoven material.

283. The swab cartridge according to any one of Embodiments 270 to 282, wherein each of the swabs is made of an at least partially absorbent material.

284. The swab cartridge according to any one of Embodiments 270 to 283, wherein each of the swabs is made of a breathable material.

285. The swab cartridge according to any one of Embodiments 270 to 284, wherein each of the swabs is made of a hydrophilic material.

286. The swab cartridge according to any one of Embodiments 270 to 285, wherein each of the swabs is made of a thermoplastic material.

287. The swab cartridge according to any one of Embodiments 270 to 286, wherein each of the swabs is made of ultra-high-molecular-weight polyethylene (UHMW-PE).

288. The swab cartridge according to any one of Embodiments 270 to 287, wherein each of the swabs is made of a material having average pore size between 8 μm to 12 μm.

289. The swab cartridge according to any one of Embodiments 270 to 288, wherein each of the swabs has a height dimension, in the direction extending between the swab top portion and the swab bottom portion, and a width dimension orthogonal to the height dimension.

290. The swab cartridge according to Embodiment 289, wherein the height dimension is between 6 mm to 15 mm.

291. The swab cartridge according to Embodiment 289 or 290, wherein the width dimension is between 4 mm to 10 mm.

292. The swab cartridge according to any one of Embodiments 289 to 291, wherein a ratio of the height dimension and the width dimension is between 1.2 and 1.7.

293. The swab cartridge according to any one of Embodiments 289 to 292, wherein each of the swabs has a rigidity along the height dimension higher than a rigidity along the width dimension.

294. The swab cartridge according to any one of Embodiments 270 to 293, wherein the swab cartridge is disc shaped.

295. The swab cartridge according to any one of Embodiments 270 to 294, wherein each of the swabs is cylindrical shaped.

296. The swab cartridge according to any one of Embodiments 270 to 295, wherein each of the swab stabilizing locations is shaped to support the swab along at least a portion of the height dimension of the swab.

297. A swab for cleaning a septum of a vial, the swab being made of a nonwoven material and having a ratio of a height dimension to a width dimension ranging between 1.2 and 1.7, wherein the swab has a rigidity along the height dimension higher than a rigidity along the width dimension.

298. The swab according to Embodiment 297, wherein the swab is made of an at least partially absorbent material.

299. The swab according to Embodiment 297 or 298, wherein the swab is made of a breathable material.

300. The swab according to any one of Embodiments 297 to 299, wherein the swab is made of a hydrophilic material.

301. The swab according to any one of Embodiments 297 to 300, wherein the swab is made of a thermoplastic material.

302. The swab according to any one of Embodiments 297 to 301, wherein the swab is made of ultra-high-molecular-weight polyethylene (UHMW-PE).

303. The swab according to any one of Embodiments 297 to 302, wherein the height dimension is between 6 mm to 15 mm.

304. The swab according to any one of Embodiments 297 to 303, wherein the width dimension is between 4 mm to 10 mm.

305. The swab according to any one of Embodiments 297 to 304, wherein the nonwoven material has average pore size between 8 μm to 12 μm.

306. The swab according to any one of Embodiments 297 to 305, wherein the swab is cylindrical shaped.

307. An automated vial preparation module that, when in use, prepares vials for being used in pharmaceutical compounding, said preparation of vials comprising at least cleaning a septum of a vial, said vial preparation module comprising:

a vial mount for receiving a vial to be prepared;

a disinfecting solution reservoir holder for holding a disinfecting solution reservoir storing a disinfecting solution;

wherein the automated vial preparation module comprises at least one of the following combinations:

a first combination comprising:

a dropper mechanism operable to selectively drip the disinfecting solution from the disinfecting solution reservoir held at the disinfecting solution reservoir holder; and control circuitry for maneuvering the dropper mechanism for dripping a controlled volume of the disinfecting solution from the disinfecting solution reservoir held at the disinfecting solution reservoir holder onto a septum of the vial to apply the disinfecting solution on the septum; and a second combination comprising:

a manipulator including a swab gripper operable to grip a first swab; and control circuitry for:

maneuvering the manipulator for: gripping the first swab, and at least partially soaking the first swab with the disinfecting solution stored in the disinfecting solution reservoir held at the disinfecting solution reservoir holder; and maneuvering at least one of the vial mount and the manipulator for contacting the soaked first swab with a septum of the vial to apply the disinfecting solution on the septum.

It is noted that all features described herein with respect to a certain aspect can be applied to any of the other aspects.

As referred to herein, a "manipulator" may include a structure and/or a mechanism configured to controllably interact with at least one component, for example a vial or portions thereof (e.g. a cap), a swab, or other component. The manipulator can be configured to engage and optionally move the component. The manipulator can include an actuator, e.g. a motor for facilitating its operation.

As referred to herein, "transferring means" may include a robot arm, a lifting apparatus, a gripper, jaws, or other holder suitable for engaging a component, such as a vial, and moving the component to a desired position and/or orientation.

As referred to herein, an "automated pharmaceutical preparation system" can be configured for performing the operations related to transfer of pharmaceuticals between different fluid transfer apparatuses including containers, fluid transfer assemblies, connectors, conduits, pumps, syringes, vials, IV bags, adaptors, needles, etc. The pharmaceutical preparation system may comprise any one or more of a dilution station, namely a reconstitution station where any type of a dilutant is added to a drug which is in solid and/or liquid form and/or any one or more of a filling station, namely a compounding station where an at least partially or fully prepared drug is transferred into a container.

As referred to herein, a "vial" may include a closable vessel, formed for example of glass or plastic, such as an ampule or bottle, and containing a drug in liquid or dry form, such as powder. The vial can be a single or multiple use vial. The vial can be tubular or bottle shaped, having a neck portion in proximity to the vial septum. The vial can be topped with a cap.

In some examples, a vial adaptor is mounted onto an open, decapped vial. The vial adaptor may include a device mountable onto a vial, for facilitating transfer of the vial itself (e.g. by grasping the adaptor instead of grasping the vial) and/or for facilitating fluid transfer into or from the vial. The vial adapter may provide closed access to the contents of the vial. The vial adaptor may be a single use or multiple use.

Typically, contents of a vial may include a fluid or powder. Fluid may typically comprise a drug, a diluent, saline solution, water or any other fluid.

As referred to herein, a "vial mount" may include a designated location inside the module for the vial to be positioned on, for example when preparation of the vial is carried out, such as removal of the vial cap and disinfecting of the vial. The vial mount may be shaped as a raised platform, and may include means, such as grippers, for stably holding the vial to the mount. In some examples, at least the surface on which the vial is positioned is rotatable, for turning the vial about the vial long axis.

As referred to herein, a controller or control circuitry may comprise a computer controller configured to perform operations in accordance with a set of instructions stored on a memory readable by the controller, which may be executed by a central processing unit (CPU), one or more processors, processor units, microprocessors, etc. In some examples, the controller or control circuitry can include one or more mechanism controllers or any other suitable means for controlling elements of modules and/or systems as described herein.

As referred to herein, a position or a location of a component within the vial preparation module may be defined relative to other components, surfaces, or reference points within the module. In some cases, the location may be adjustable or variable to accommodate different vial sizes, preparation processes, or module configurations. The position may be characterized by coordinates in one or more dimensions, angular orientations, or distances from specified features. In certain implementations, the location of a component may be dynamically controlled or monitored by the control circuitry to optimize performance or adapt to changing conditions. The position may also be designed to facilitate access, visibility, cleaning, or interaction with other module elements. In some embodiments, the location of certain components may be critical for maintaining sterile conditions, ensuring proper disinfection, or enabling precise manipulations during the vial preparation process. In some examples, a position or a location of a component of the module is identified in images captured by an image apparatus, and is then monitored, verified, and/or otherwise controlled in accordance the identification in the image(s).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 10A-G are various views of a vial preparation module at various stages of operation, according to embodiments of the present disclosure;

DETAILED DESCRIPTION OF EMBODIMENTS

Figure 1:
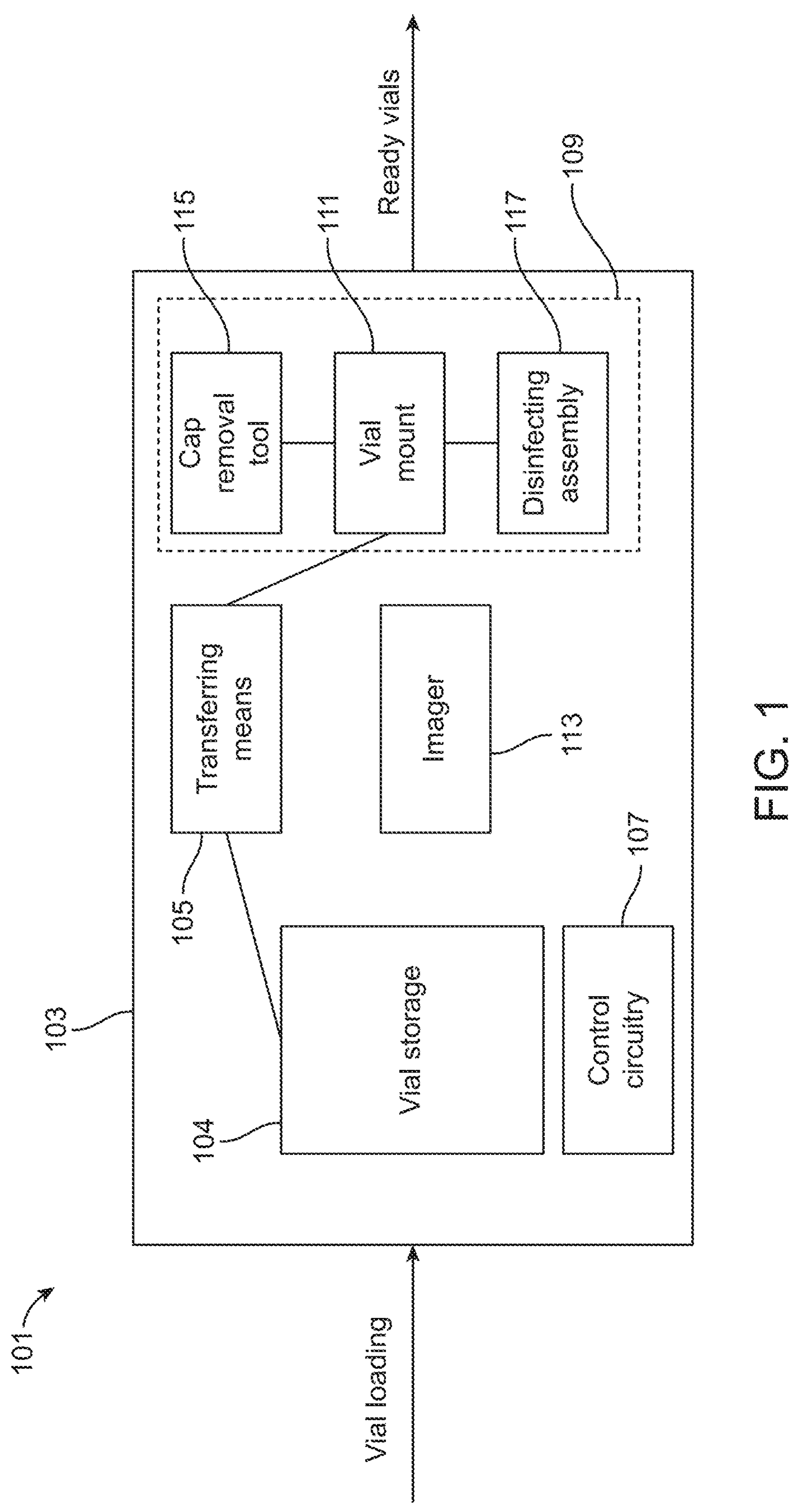
FIG. 1 is a block diagram of a vial storage and preparation module, according to embodiments of the present disclosure.

FIG. 1 is a block diagram of a vial storage and preparation module, according to embodiments of the present disclosure.

In some embodiments, the module serves both as a vial inventory in which vials are stored and managed, and as a preparation station for decapping and disinfecting of vials. The module can be used for preparing one or more selected vials for a pharmaceutical compounding process, performed either by an automated system or manually.

The module is intended to at least partially replace the work of a pharmacist, nurse, lab technician or any other human operator. For instance, the human operator may be involved only at the stage of loading vials onto the module, while one or more of sorting of the vials, storing of the vials, decapping and cleaning of the vials can be performed in a fully automated without human intervention. By that, a risk of contamination of the vial contents and/or a risk of exposure of the human operator to dangerous contents (e.g. hazardous drugs) may be reduced or prevented.

As shown in FIG. 1, module 101 comprises an external housing 103 which defines a controlled, regulated, clean volume therein. The module can comprise air filtration and/or ventilation mechanisms for controlling the flow inside the housing, capturing hazardous fumes and/or particles, and preventing contamination. Housing 103 is generally sealed, in a manner in which any access opening(s) to the housing are normally closed and are configured to maintain the controlled conditions (e.g. air flow and circulation, humidity, temperature, or as such) inside the housing. Generally, in at least a portion of the housing a clean air environment is maintained, for example as defined in regulation "ISO 14644-1-Cleanrooms and associated controlled environments", in which air cleanliness by particle concentration is defined. In some embodiments, components for providing clean air such as fans, high efficiency particulate air (HEPA) filters and/or ultraviolet (UV) lamp are used.

Module 101 is configured for receiving vials, and transferring the vials into a vial storage 104 of the module. In some embodiments, the vials can be loaded onto the module in a random, non-restricted order or position, for example placed on a tray of the module, and picked up by transferring means 105 of the module, for example, a robotic arm having a gripper at an end thereof. The transferring means can then move each of the loaded vials to a designated cell, slot or other opening of the vial storage. Sorting of the vials into designated positions in the vial storage can be performed based on vial data such as the vial content, expiration date, maintenance conditions, level of toxicity, or other data. In some embodiments, a vial label is scanned, and the vial data is obtained from a vial barcode or other suitable coding. In some embodiments, vial data is obtained with the aid of an imager 113 of the module.

A control circuitry 107 of the module can be programmed to manage the inventory of the vials in the storage, time the loading of the vials into the module, select a vial position based on the vial data, select a vial for use based on the expiration date (e.g. use older vials before newer ones), notify regarding an expired vial, move vials from one location to another in the storage, queue the vials, or otherwise manage the loaded vials, the stored vials and/or the vials which are selected for preparation. In some embodiments, the control circuitry sets the timing in which loading of the vials into the module is performed, for example so that loading can take place when the transferring means 105 are not otherwise occupied (e.g. for transferring vials from the storage into preparation, as further described hereinbelow).

For the purposes of the present description, a control circuitry or controller or a controller unit can be understood as comprising a computer controller configured to perform operations in accordance with a set of instructions stored on a memory readable by the controller, which may be executed by a central processing unit (CPU), one or more processors, processor units, microprocessors, etc. In another embodiment the control circuitry or controller unit includes one or more control circuits. The controller circuitry may comprise any means to control elements in the automated pharmaceutical preparation systems and may comprise at least any one of a controller, a synchronizing unit and a processer.

Generally, vial storage 104 can comprise a plurality of shelves or drawers, each including multiple vial positions. The shelves can be movable, for example slidable along the vertical and/or horizontal axis of the module housing. In some embodiments, one or more of the shelves are temperature controlled, for example actively cooled, and are used for storing vials which require cooled storage conditions. Similarly, lighting conditions can be controlled, e.g. exposure of the vials to direct light can be avoided; as well as humidity conditions.

Upon receipt of a request to prepare a vial, e.g. as received by the control circuity of the module, (with the request being made by a system user; an interfacing system (e.g. a hospital or pharmacy system), a network request or other), transferring means 105 approach the vial based on its designated position in the storage; pick up the vial and transfer the vial to a vial preparation zone 109 of the module, for example, to a vial mount 111 located in the preparation zone. Once the transferred vial is verified, e.g. with the aid of the imager (or imaging apparatus) 113 (for example according to a scanned label or other ID of the vial), preparation of the vial can include removal of the vial cap by a cap removal tool 115; followed by disinfecting of the vial septum, neck and/or other vial portions by a disinfecting assembly 117.

In some embodiments, the cap removal tool and the disinfecting assembly are positioned and configured to operate on the vial when the vial remains held at a same position, e.g. on the vial mount. Potential advantages of the cap removal tool and the disinfecting assembly being located with respect to the vial mount and configured to act on a vial held on the mount may include reducing or preventing movement of the vial during preparation, thereby potentially increasing safety, reducing a risk of spill, reducing a risk of breakage, reducing undesired agitation of the vial contents, and potentially simplifying and accelerating the preparation process.

Ready vials prepared by the module can then be transferred to an exit platform of the module, from which they can be picked up for compounding or other future processing.

Although the vial preparation module 101 has been illustrated and described with respect to FIG. 1 as including the housing 103, vial storage 104, transferring means 105, control circuitry 107, imager 113, vial mount 111, cap removal tool 115, and disinfecting assembly 117, it is to be understood herein that a vial preparation module can include only some of these components in various combinations. For instance, in some examples, a vial preparation module can include a vial mount and a disinfecting assembly. In some examples, a vial preparation module can include a cap removal tool, a vial mount, and a disinfecting assembly. In some examples, a vial preparation module can include a vial mount, a disinfecting assembly, and a control circuitry. In other words, one or more of the vial storage, control circuitry, transferring means, imager, and cap removal tool can be external to a vial preparation module.

Accordingly, a vial preparation module can generally include only those components required for holding a vial (for example, a vial mount) and disinfecting a vial (for example, a disinfecting assembly). In such examples, the vial can be directly positioned at a vial mount after removal of its cap, and the disinfecting assembly can clean (disinfect) at least the septum of the vial. In some examples, a vial preparation module can generally include a cap removal tool in addition to those components required for holding a vial (for example, a vial mount) and disinfecting a vial (for example, a disinfecting assembly). In such examples, the vial can be directly positioned at a vial mount without removing its cap, and the cap removal tool can remove the cap, and the disinfecting assembly can clean (disinfect) at least the septum of the vial. The operation of the cap removal tool (if included in the module), vial mount (gripping the vial and/or moving the vial, as described in detail herein), and the disinfecting assembly can be controlled by a control circuitry, which can be a part of the vial preparation module or external to the module. One or more of the above-mentioned operations can be monitored by the control circuitry and/or an imaging apparatus (imager) based on images of the preparation process captured by the imaging apparatus. The imaging apparatus can be a part of the vial preparation module or external to the module.

It is to be understood herein that a vial preparation module can include as a part thereof a housing, for example, as illustrated in FIG. 1, or the components thereof can be positioned in any housing having controlled inner environment, for example a hood for a drug compounding system. In such examples, the control circuitry and/or imaging apparatus of the drug compounding system can operate with the vial preparation module as well. In some examples, a vial preparation module can be positioned in a hood for a drug compounding system and can still have its separate control circuitry and/or imaging apparatus.

In some or all of the examples described above, a disinfecting assembly can include at least one of: a means to apply a disinfecting solution on at least the septum of the vial; and a means to grip a swab and wipe at least the septum of the vial. For example, the disinfection of the vial can include either or both of applying a disinfecting solution on the septum and wiping the septum with a swab. In some examples, the disinfecting assembly can further include a means for an ultraviolet (UV) radiation to expose at least the septum of the vial to the UV radiation. The vial preparation module can include a manipulator including the means of the disinfecting assembly. For the purposes of disinfecting the vial, either or both of the vial mount and the manipulator can be maneuvered by a control circuitry, as described in detail herein further below.

In some or all of the examples described above, the vial preparation module can include a means for mounting a vial adaptor on the vial after disinfection of the vial, and accordingly, the preparation of the vial can include mounting a vial adaptor on the vial. In some examples, the vial adaptor is provided in a sterile package or blister which is unsealed prior to use of the adaptor. The vial preparation module may include means (optionally, the same means that are usable for moving the vial, such as a robotic arm) for picking up the adaptor from its package or blister and placing the adaptor onto the cleaned vial septum.

Figure 2:
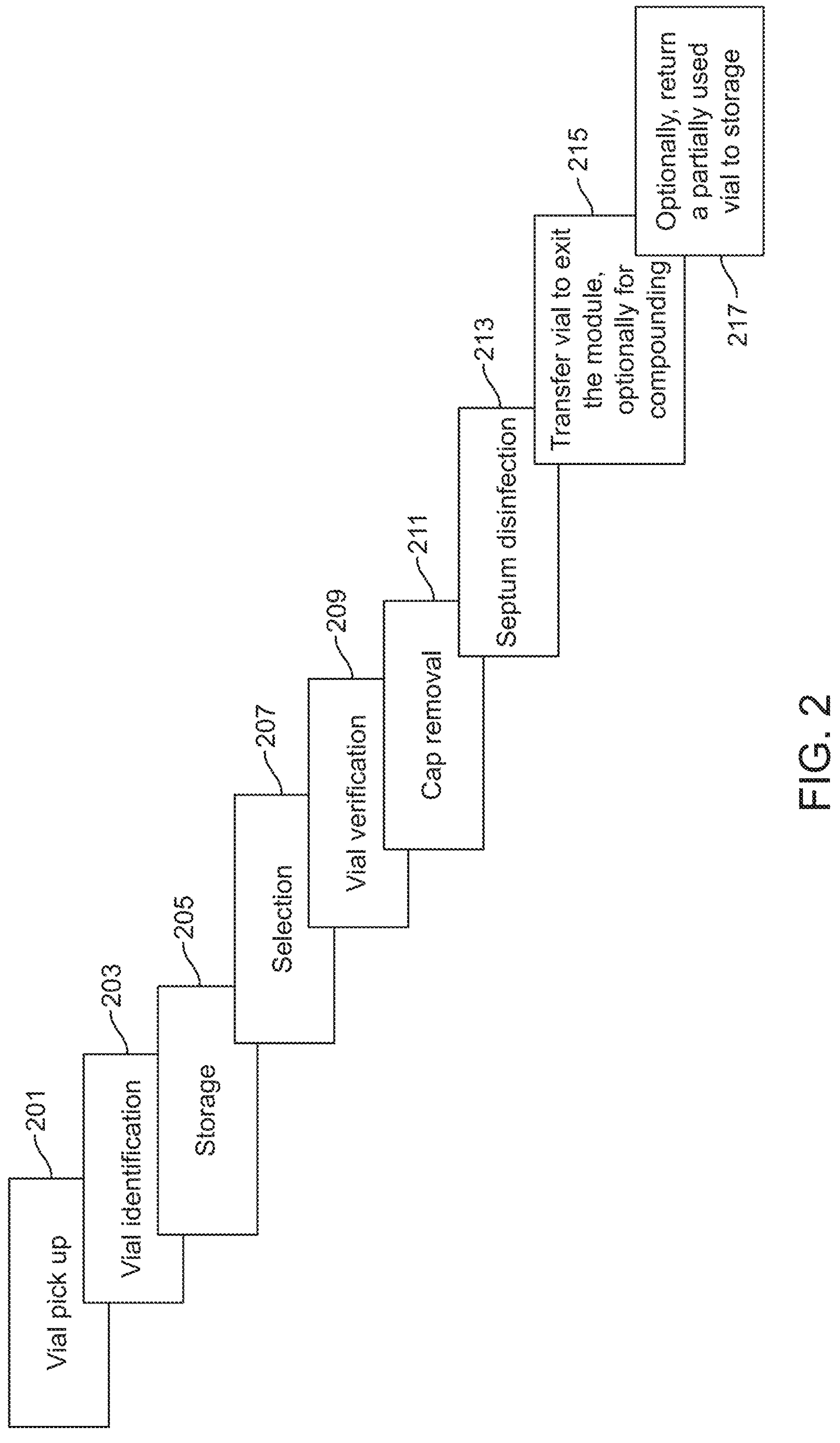
FIG. 2 is a flowchart of a work process carried out by a vial storage and preparation module, according to embodiments of the present disclosure.

FIG. 2 is a flowchart of a work process carried out by a vial storage and preparation module, according to embodiments of the present disclosure.

At 201, a vial that was placed (e.g. by a user) on a tray of the module is picked up by the module, for example by the transferring means (e.g. robot arm or other suitable lifting, gripping and transferring means).

At 203, the vial is identified, for example by scanning its label, capturing an image of the vial, and/or other suitable identification. Optionally, the identified vial is compared with listing on a database or a memory, which details the number and/or content of the vials that are expected to be loaded onto the module.

At 205, the identified vial is placed in its designated storage position, for example within a slot of a storage shelf or drawer of the module.

At 207, upon receipt of an order for one or more specific vials (or contents thereof), the required vial is selected and picked up from the storage by the transferring means.

At 209, verification of the vial is carried out, ensuring that the correct vial was selected.

At 211, preparation of the vial begins by removal of the vial cap. The cap may be removed by one or more of: lifting the cap, rotating the cap with respect to the vial and/or rotating the vial with respect the cap, penetrating the cap (or a safety seal, if exists), or other cap removal methods.

At 213, disinfection of the vial, such as of the vial septum, is carried out, for example by applying a disinfecting solution on the septum and/or wiping the vial septum with a swab, for example, by passing the swab over the surface of the septum, optionally repetitively. The applying of the disinfecting solution can be performed in any one or both of the following manners:

- dripping a disinfecting solution directly on the septum, for example, directly from a solution reservoir or by soaking a swab with the disinfecting solution and squeezing (or otherwise manipulating) the swab from above the septum to drop the disinfecting solution from the swab onto the septum; and
- soaking a swab with the disinfecting solution and contacting the soaked swab with the septum.

At 215, the prepared vial is moved to out from the module, e.g. to an exit platform of the module, for further compounding or other use;

At 217, in some cases, a prepared vial which was not used or only partially used during compounding, is returned back into the module, and optionally back into storage. This may be especially relevant in situations where the module is used with an automated compounding system, with both optionally being in the same hood. In such situation, the vial can be prepared, transferred into the compounding system, used in part (or not used at all), and returned to the module for storage. Circuitry of the module, compounding system or both altogether may keep track of the vial content that was used and/or the remaining vial content (e.g. volume), for determining whether to return the vial into storage. In addition, the circuitry can check the expiry date as well as the time period from opening during which the vial is still allowed to be used, and determine if to store the vial again, for how long, and in which storage conditions. A potential advantage of the described scenario in which a vial is returned into storage may include that the vial remains in a volume in which conditions are controlled (e.g. air is filtered, circulated, or the like) throughout initial storage, preparation, compounding and re-storage processes, optionally without involvement and handling by a human. Another potential advantage of the described scenario may include reducing waste and providing a more cost-effective use of the vial contents.

In some embodiments, a vial that was returned from the compounding system includes a vial adaptor that had been previously placed onto the exposed vial septum (e.g. before/when the vial was transferred from the module to the compounding system). The adaptor therefore serves as a temporary cap for the vial, and the vial can be returned to storage in the module along with the attached adaptor. In some cases, when the partially used vial is again selected for use, it can be disinfected again before being transferred to the compounding system, for example by wiping the vial adaptor with the swab, in a similar manner to wiping a vial septum with the swab.

It is to be understood herein that in various examples, an automated work process carried out by a vial preparation module can include only some of the steps described above in various combinations.

In general, a process of preparation of a vial can include only receiving (and/or holding) a vial on a vial mount and disinfecting the vial (for example, by a disinfecting assembly, as described herein). In such examples, the vial can be directly positioned at a vial mount after removal of its cap, and disinfecting of at least the septum of the vial can be performed by a vial preparation module. In some examples, the process of preparation of a vial can include a cap removal step in addition to receiving a vial and disinfecting the vial. In such examples, the vial can be directly positioned at a vial mount without removing its cap, and a cap removal tool of the vial preparation module can remove the cap, and a disinfecting assembly can clean (disinfect) at least the septum of the vial. The operations of the vial preparation process can be monitored and accordingly controlled by a control circuitry, which can be a part of the vial preparation module or external to the module. One or more of the above-mentioned operations can be monitored by the control circuitry, optionally based on images of the preparation process captured by an imaging apparatus. The imaging apparatus can be a part of the vial preparation module or external to the module.

It is to be understood that controlling and/or monitoring the module based on images captured by the imaging apparatus may include one or more of receiving the images, storing the images at a memory, processing the images (e.g. using image processing algorithms or any relevant image analysis methods). In some examples, the one or more imaging apparatuses of the module are configured to continuously capture images (optionally, video) throughout the vial preparation process. Alternatively, images are captured at predetermined times of the process. Optionally, the captured images are analyzed in real time, allowing the control circuitry to make decisions and control upcoming actions immediately based on the results of the image analysis.

Further with respect to the imaging apparatus and its use, the imaging apparatus is generally configured to capture images of various components and/or processes within the module. The imaging apparatus may comprise one or more cameras, sensors, or other image capture devices positioned to monitor different areas of the module. These may include, but are not limited to, the vial mount, swab manipulator, disinfecting assembly, vial storage, and vial transfer mechanisms. The imaging apparatus may capture still images, video, thermal images, or other types of visual data. This visual information may be processed by the control circuitry to verify proper execution of preparation steps, detect errors or anomalies, identify vials, assess cleanliness, measure fluid levels, or gather other relevant data to optimize and validate the vial preparation process. The type, number, positioning and capabilities of the imaging components may be customized based on the specific monitoring needs of a given module configuration.

In some or all of the examples described above, disinfecting a vial can include at least one of: applying a disinfecting solution on at least the septum of the vial; and wiping at least the septum of the vial with a swab. In some examples, disinfecting the vial can further include exposing the vial (at least the septum) to ultraviolet (UV) radiation. For the purposes of disinfecting the vial, either or both of the vial mount and a manipulator including means for disinfecting the vial can be maneuvered, as described in detail herein further below.

In some or all of the examples described above, the vial preparation process can include mounting a vial adaptor on the vial after disinfection of the vial.

Figures 3A, 3B:
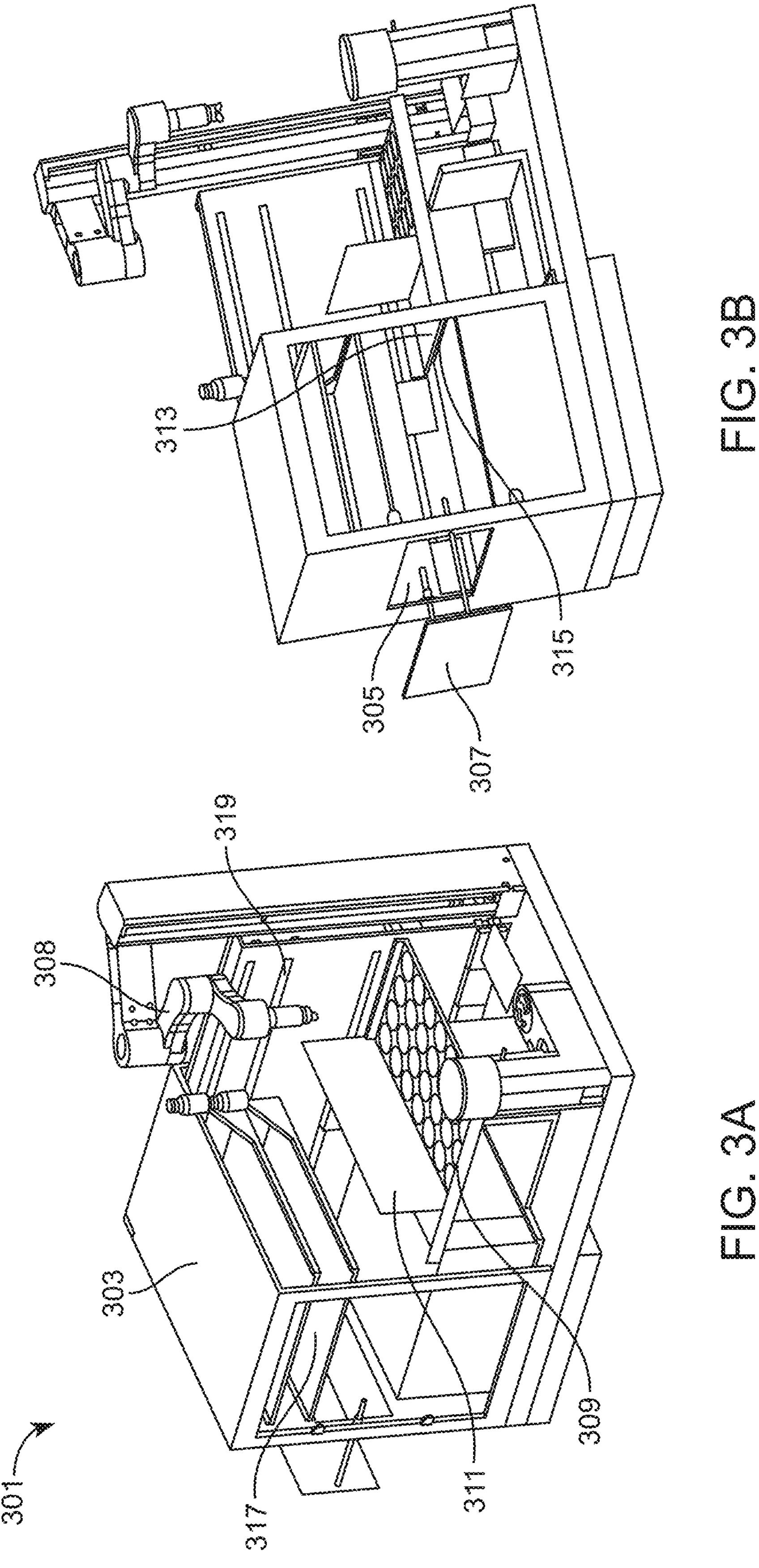
FIGS. 3A-B are two views of a vial storage and preparation module, according to embodiments of the present disclosure.

FIGS. 3A-B are two views of a vial storage and preparation module, according to embodiments of the present disclosure.

As shown, module 301 comprises a housing 303 (shown only in part). The housing defines an inner volume in which conditions are controlled.

To enable access to the housing, an opening 305 (e.g. a window) in the housing is covered by a normally closed cover 307. In some embodiments, cover 307 is spring-actuated so that it is normally in a sealed fit with the opening, covering the opening, and when pushed (or pulled, or otherwise manipulated) the cover is moved to expose the opening. Once the cover is released, it returns to its normally closed state.

The module includes a tray 309 for loading the vials, configured behind cover 307. Tray 309 includes a vertically extending wall 311, which is shaped and sized similarly to cover 307, so as to enable closure of the opening 305. Tray 309 includes a surface 313 on which vials can be placed during loading, the surface extending from the vertical wall and in the direction of opening 305 of the module housing. In some embodiments, surface 313 is planar and has no defined locations (smooth surface), so that vials can be randomly placed thereon, for example by a human operator. In some embodiments, surface 313 can have defined slot locations for the vials.

In use, for enabling vial loading, tray 309 is moved, for example slides on a track, (e.g. via motorized actuation) in the direction of opening 305. The tray (for example the front edge 315 of the tray) then pushes the cover 307 outwardly from the housing and away from the opening, positioning surface 313 at least partially externally to the housing. Vials can then be placed on the tray, e.g. by a user, to be loaded onto the system. In this position of the tray, the vertical wall 311 is located to sealingly close the opening instead of the cover, thereby maintaining the controlled conditions of the inner volume of the housing. Once the vials are loaded onto surface 313, the tray can be returned into the housing, and the cover 307 springs back to its original position in which it closes the opening. Once the vials are inside the module, they can be identified, picked up and transferred to designated storage locations by the robot arm 308.

Figure 4:
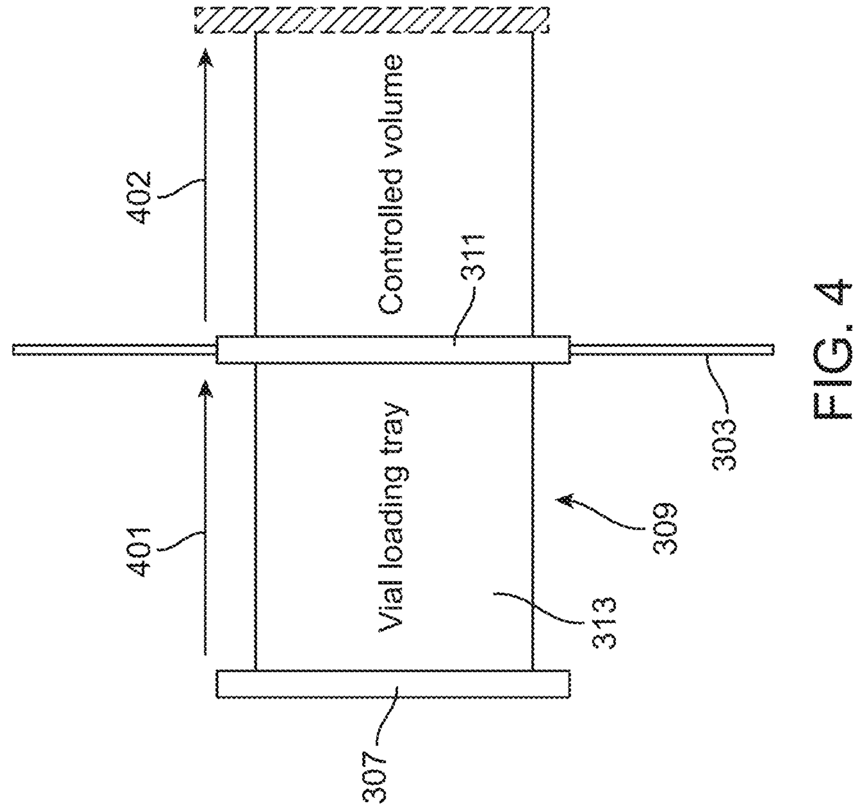
FIG. 4 schematically illustrates movement of a vial loading tray of the module between at least two positions, according to embodiments of the present disclosure.

The above construction is shown conceptually in FIG. 4, which schematically illustrates movement of the vial loading tray of the module between at least two positions. Spring actuated cover 307 is shown in its extended position, being pushed externally to housing 303; vertical wall 311 of the tray 309 is shown to close the opening in the housing, while the surface 313 of the tray is located externally to the housing to enable placing vials thereon. Arrows 401 and 402 indicate the movement of cover 307 and of tray 309 (inclusive of vertical wall 311), respectively, to return to their initial position, in which the tray is inside the housing, and cover 307 seals the opening.

Referring now again to FIG. 3, storage of the vials that are loaded onto the module can be in the form of a plurality of shelves or drawers 317, whereby each drawer includes multiple designated locations (e.g. slots arranged as a matrix or a grid) for receipt of the vials. In some embodiments, each of the drawers is movable, for example slidable sideways along a track 319, to enable access to the vials stored therein. In some embodiments, robot arm 308 is configured to reach into drawers located at different heights, for example when a selected drawer is moved sideways and can be accessed. The robot arm can then reach a vial stored in a specific slot location of the moved drawer, grasp the vial and lift it. A potential advantage of the storage drawers each being independently movable to a position in which the drawer is not directly aligned with the other drawers may include facilitating access of the robot arm to the vials stored in the drawer, and further allowing for a more compact arrangement of the drawers, since they can closely fit one on top of the other when not selected for use.

Figure 5:
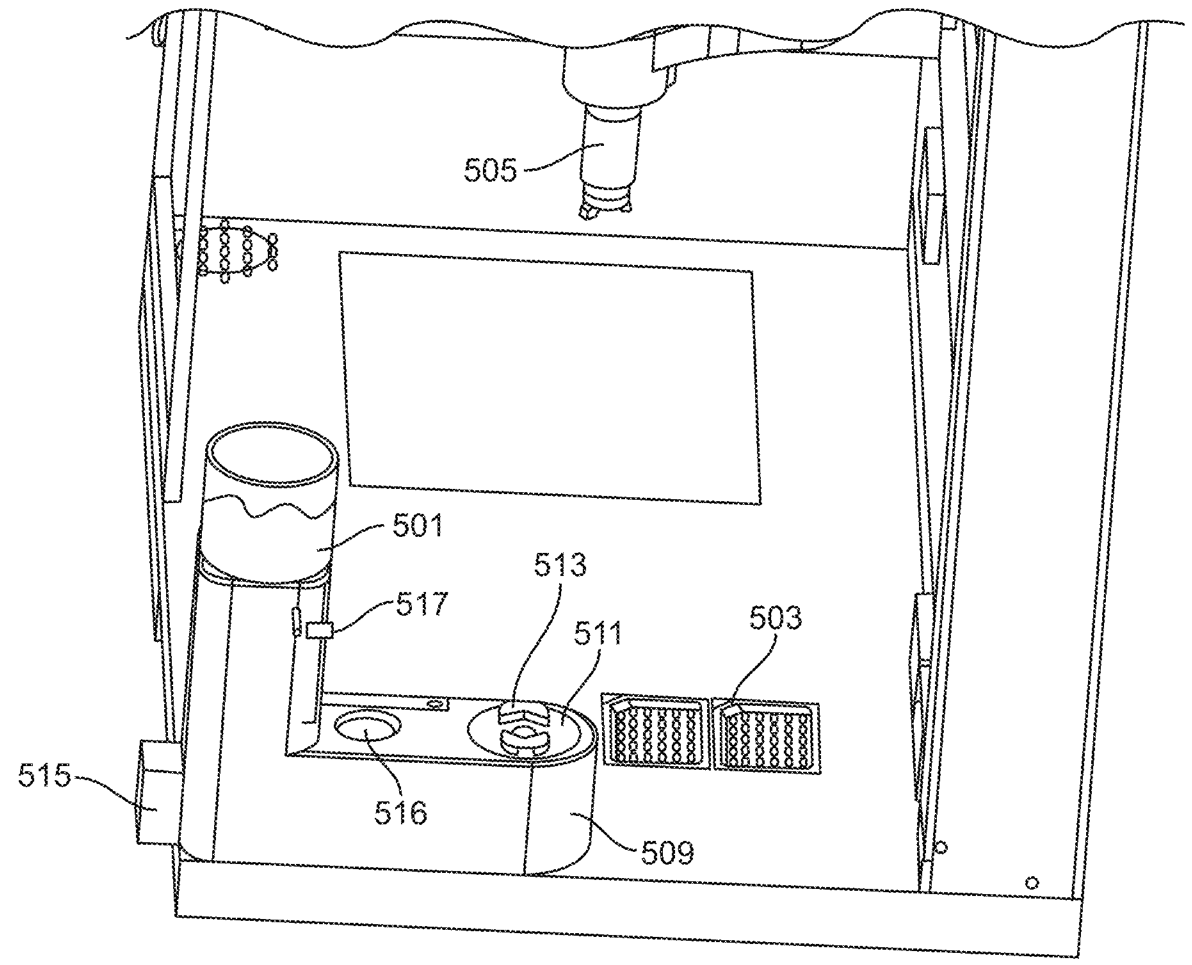
FIG. 5 shows an example of a vial disinfecting assembly of the module, according to embodiments of the present disclosure.

FIG. 5 shows an example of a vial disinfecting assembly of the module, according to embodiments of the present disclosure.

The disinfecting assembly is generally configured for cleaning at least a portion of the vial, such as the vial septum and/or neck, to reduce or eliminate contaminants (such as microbial contamination) and remove dust, dirt or the like. The assembly can apply a disinfectant (disinfecting solution), such as an alcohol-based solution, onto an outer surface of the vial, and specifically onto the septum. The disinfectant can be applied by spreading the solution on the vial, e.g. by wiping the vial with a swab previously dipped in (and soaked with) the solution.

In the example shown in FIG. 5, the disinfecting assembly comprises the following components:

- A reservoir 501 of the disinfecting solution, e.g. a container, tank or other suitable receptacle in which a desired volume of solution can be contained;
- A swab stock 503 comprising a plurality of swabs, for example arranged on a blister or tray (swab cartridge). In some embodiments, a swab comprises a small sponge, pad or other absorbent material, for example formed as a cylindrical stub;
- A manipulator 505, which, in this example, includes a swab gripper of the robot arm (transferring means of the module); in other embodiments, the swab gripper can be any suitable gripping and transferring tool which can pick a swab from the swab stock, dip the swab in the reservoir, move the swab to the vial and along at least a portion of the vial septum surface, and release the swab;
- A vial mount 509, having an upper surface 511 shaped to receive and hold a vial thereon. The vial mount can include stabilizers 513, optionally, adjustable in position, for engaging a bottom of a vial held on the mount and holding the vial steady;
- A swab disposal bin 515, having an opening 516 leading thereto;
- An imager 517 configured to capture images of one or more of: a vial held on the vial mount, the reservoir, the swab gripper.

In use, the following is performed: a vial that was selected from storage, identified and de-capped is placed on the vial mount. (Optionally, identification and cap removal are carried out when the vial is already placed on the vial mount).

The swab gripper is configured to engage a single swab from the swab stock; pick the swab up and then dip the swab, at least partially, in the solution reservoir. The soaked swab is then transferred by the manipulator to the position of the vial mount, and guided, optionally with the aid of the imager, to the septum of the vial. In some embodiments, the swab gripper comprises a resilience, shock absorbing mechanism which allows the swab to be pushed by the swab gripper against the surface of the vial septum, yet restrain the push force so as to prevent damage to the vial or to the manipulator (e.g. to the swab gripper end of the manipulator). In some embodiments, the mechanism comprises an anti-collision unit for reducing or preventing collision of the swab gripper with the vial septum. In some embodiments, a telescopic structure of the swab gripper arm and/or one or more springs incorporated in the swab gripper constitute the mechanism.

The manipulator then moves the swab along the vial septum, for example circumferentially along the septum, to spread the solution thereon. In some embodiments, a diameter of the vial septum and/or the height of the septum (e.g. with respect to the vial mount surface or other reference plane) and/or other vial parameters are assessed with the aid of imaging and/or are provided as inputted vial data, and the swab gripper moves the swab to the level of the septum (according to the height data) and then along the septum (e.g. circumferentially along the septum) according to the diameter data.

Additionally or alternatively to moving the swab along the vial septum, in some embodiments, the vial mount is configured to rotate surface 511 so that the vial itself is rotated with respect to the swab, causing the solution absorbed in the swab to be spread onto the septum.

Generally, during de-capping and disinfecting, the vial can be maintained in an upright orientation, for example standing on the vial mount. This may be advantageous in that the vial contents, fluid or powder, can remain under gravitational force and accumulate towards the bottom of vial, for example as opposed to flowing or being spread alongside walls of the vial or accumulating towards the septum of the vial, which is likely to occur if a vial is not upright, for example, inverted. Maintaining the vial upright may also reduce or prevent potential leaks.

Following spreading of the solution on the vial septum, the used swab is tossed by the swab gripper into the swab disposal bin 515. The disinfected vial can then be transferred to a module exit position (e.g. an exit platform).

It is noted that in some embodiments, the same robot arm is configured for one or more of: gripping a vial, transferring a vial, de-capping a vial, functioning as a manipulator (picking a swab, moving the swab, disposing the swab). This may be achieved by an adjustable gripper located at a distal end of the robot arm, and/or by interchangeable grippers.

In some embodiments, image data captured by imager 517 can be processed for determining one or more of:

- A volume of remaining solution in the reservoir, which can be measured by the checking the surface level in an image of the reservoir. The reservoir may include one or more transparent walls which allow observing the level of solution inside;
- Verifying that a vial is being held on the mount, verifying the vial orientation (e.g. that the vial is not slanted), verifying parameters related to the content of the vial (e.g. type of content, presence of air bubbles, volume, cloudiness levels, or others).

Figure 6:
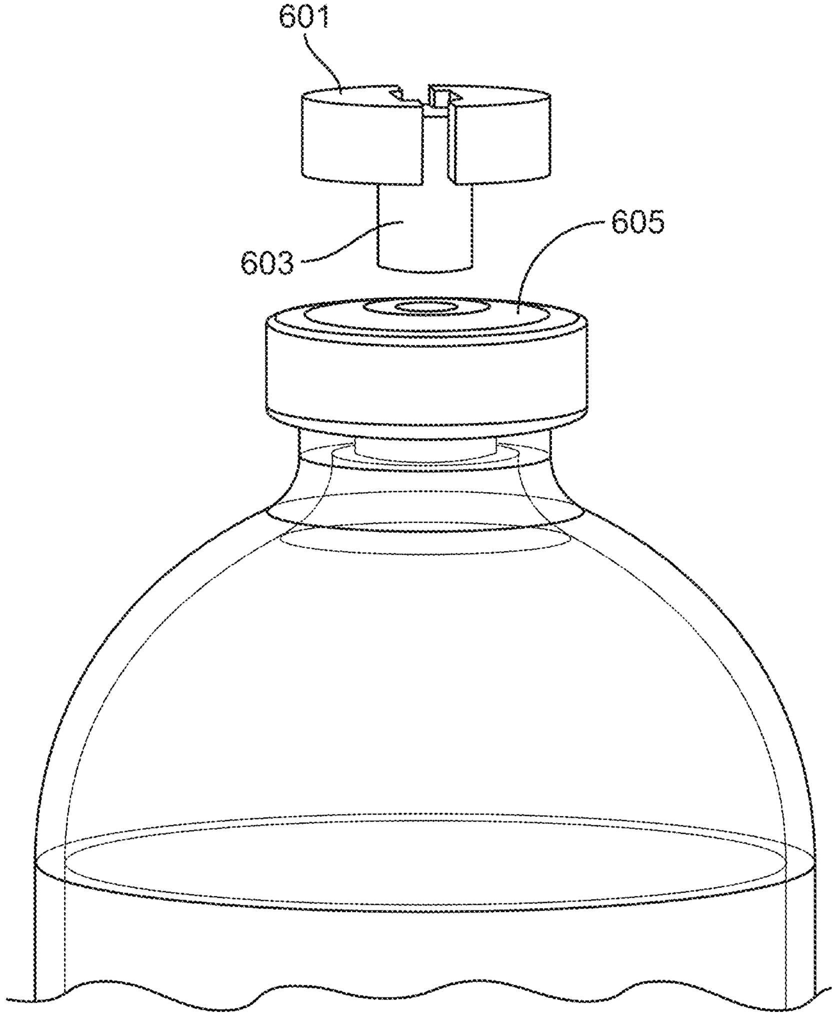
FIG. 6 schematically illustrates a disinfecting swab approaching a vial septum, according to embodiments of the present disclosure.

Checking that the solution had been spread on the vial septum; optionally, assessing whether the whole surface of the septum had been contacted by the swab. The spread solution may be identified in the image for example based on a different (e.g. darker) shade or color of the vial septum which had been cleaned, for example, immediately following contact with the swab. Additionally or alternatively, thermal imaging can be performed to identify presence of the solution on the vial. In some cases, thermal imaging is selectively applied only to vials that were not stored under cooled conditions, e.g. vials maintained at room temperature conditions. FIG. 6 schematically illustrates a disinfecting swab approaching a vial septum, according to embodiments of the present disclosure. As shown, a gripper 601 (e.g. a gripper at a distal end of the manipulator, not shown) firmly holds the swab 603. After the swab was dipped in the solution, the manipulator brings the swab into contact with the vial septum 605. The manipulator can then move the swab along the septum (e.g. in a circular movement) and/or hold the swab steady while the vial itself is rotated with respect to the swab. Following disinfecting of the vial septum, the gripper releases the swab, for example allowing the swab to drop into a swab disposal bin.

Figure 7:
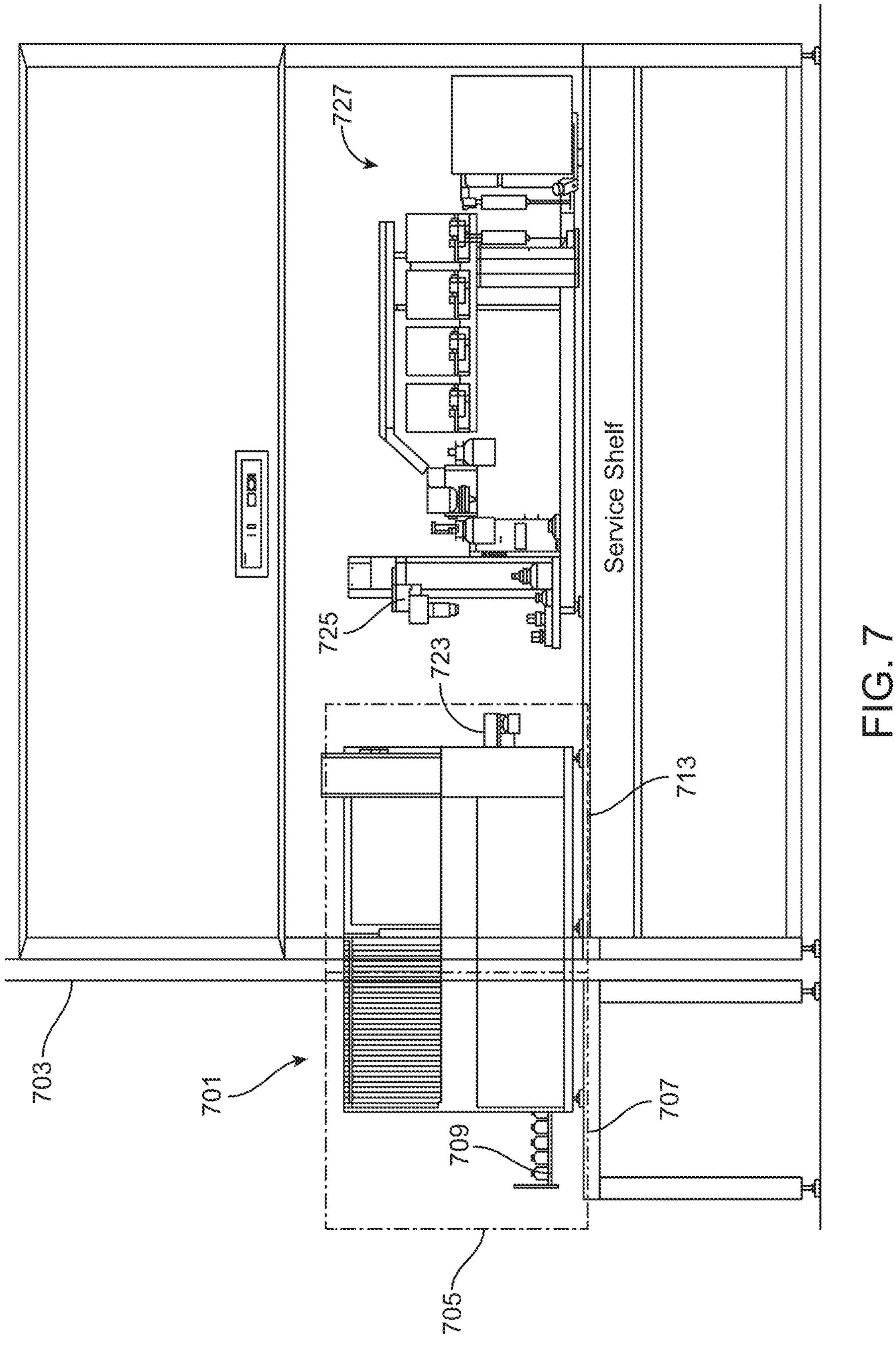
FIG. 7 is a side view of a hood in which a vial storage and preparation module is at least partially contained, the module being in an operational interface with an automated compounding system, according to embodiments of the present disclosure.
Figure 8:
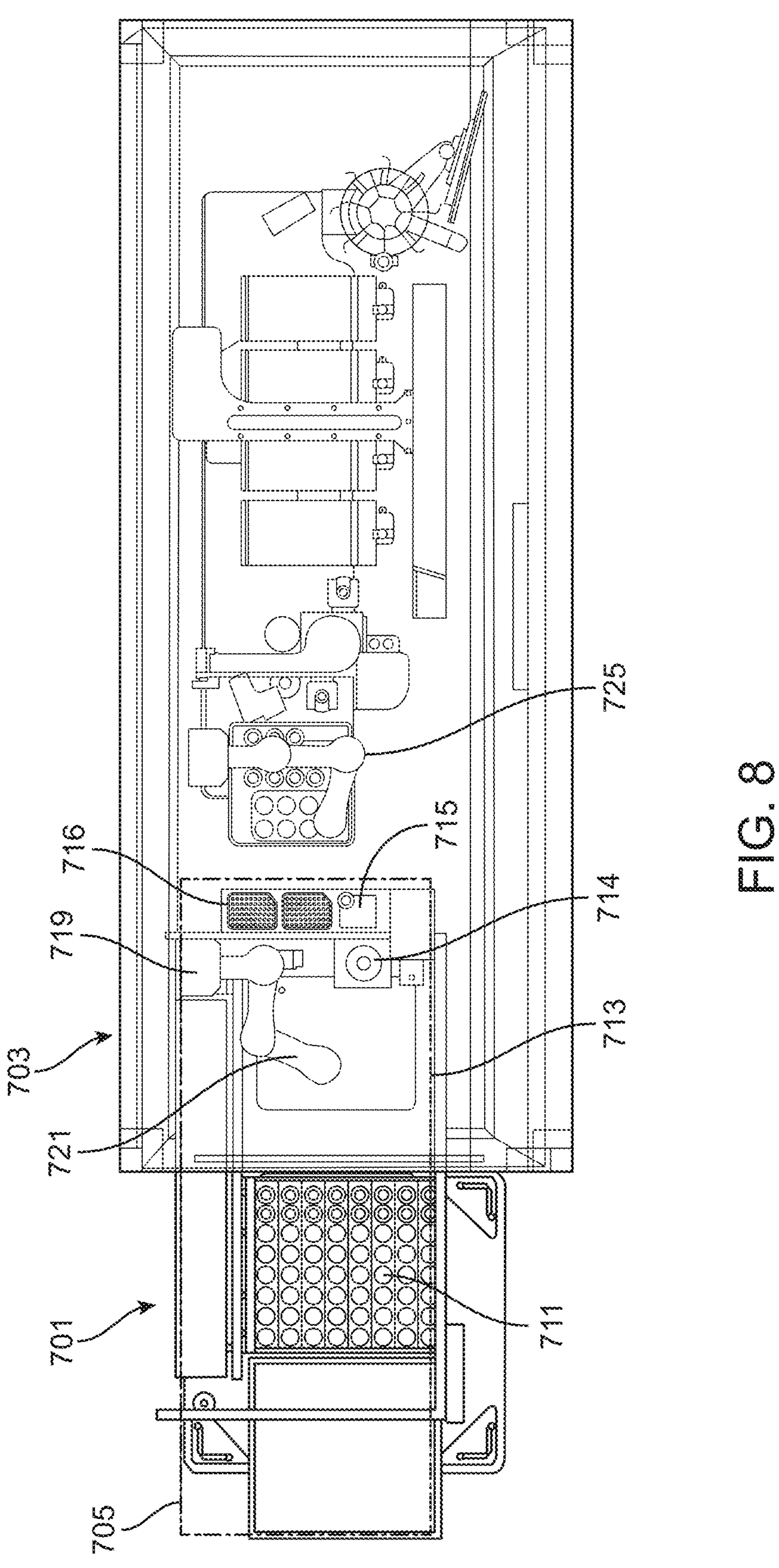
FIG. 8 is a top view of another example of a hood in which a vial storage and preparation module is at least partially contained, the module being in an operational interface with an automated compounding system, according to embodiments of the present disclosure.

FIGS. 7 and 8 are two examples of hoods in which a vial storage and preparation module is at least partially contained, the module being in an operational interface with an automated compounding system constituting a vial preparation and drug compounding arrangement, according to embodiments of the present disclosure. The module and compounding system can generally by mounted on a work surface of the hood.

In the examples shown (components are marked in either FIG. 7 or 8, where they are best shown), the module 701 is at least partially contained within a housing of a hood 703, such as a laminar flow hood. In some embodiments, a first portion of the module, schematically marked by the dashed lines and designated 705, is located outside the hood, for example supported by an external surface 707 (e.g. of a table). The first portion can include the loading tray 709 (which is configured to protrude outwardly from the module, for example as described in FIGS. 3-4); and the vial storage 711, for example including a plurality of storage drawers having designated vial storage locations. In some embodiments, a second portion of the module, schematically marked by the dashed lines and designated 713, is located inside the hood. The second portion can include, for example, the vial mount (or other suitable vial placement) 715, the disinfecting assembly (for example as described above, including a reservoir 714, a swab stock 716, and a manipulator), a base 719 of the robot arm 721, and/or other module components. As the second portion 713 is maintained inside the hood, its environmental conditions and flow of air can be controlled, for example by the hood filtration systems. In some embodiments, the continuity of the two module portions can be maintained due to a designated side opening formed in the housing of the hood, which is sealed by the module itself, such that the inner conditions of the hood can be maintained. In an arrangement as described, conditions such as of air flow and circulation, filtration etc. may differ between the first portion and the second portion of the module, whereby at the first portion the vials are loaded and optionally stored at the storage drawers, while still being capped; and at the second portion the selected vial(s) are decapped and disinfected, requiring a higher level of contamination prevention as compared to the first portion.

It is noted that in some embodiments, the module can be used independently, without a hood. For instance, the vial preparation module can have an independent hood or housing and the drug compounding system can have an independent housing or hood, and there can a transferring means that transfers the vial between the two housings.

In general, conditions which should controlled in the first and/or second portions of the module are determined based on one or more of the following, or combinations thereof:

Whether the portion is located in a hood, and is therefore under laminar flow and air filtering; in some cases, the second portion is inside the hood, while the first portion is outside the hood. Keeping the first portion outside the hood may be advantageous in that there is less interference to the laminar flow in the hood as compared to including both the first and second portions inside the hood;

The external environment in which the module is located: for example, if the module is in a clean room or lab, as opposed to a standard, non-controlled room. In case of a clean room, the first portion of the module can be free of filtration (or other "clean air") components, while the second portion will comprise filtration (or other "clean air") components; alternatively, if the module is in a non-controlled room, it can be required to at least partially control the conditions in the first portion as well, for example by suction and cycling of air, e.g. from under the storage drawers;

The type of drugs being stored and prepared by the module: if the drugs are hazardous drugs, then measures should be taken to prevent toxic gases from exiting the module, for example by suction of air as describe above; if the drugs are non-hazardous drugs, it may be possible to maintain the first portion without filtration or other air control mechanism, especially if the module is kept in a clean room. Another criteria according to which conditions of the module can be set is whether the drugs stored and prepared by the module are biological drugs or chemical drugs, which require different cleanliness conditions and maintenance. In some embodiments, in use, a vial that was stored in the module and prepared for use by the module is moved to an exit platform 723 of the module. In some embodiments, as shown, the exit platform is located at an end of the module which is opposite the loading tray of the module.

From the exit platform, the prepared vial can be picked up by transferring means (e.g. a robot arm 725) of the automated pharmaceutical compounding system 727. Optionally, a vial adaptor is installed on the open vial, for example mounted onto the vial septum by robot arm 725.

At the compounding system, the vial may go through processes such as dilution, reconstitution, agitation, withdrawal of fluid therefrom, and/or other processes carried out the by the system. At the end of use, the vial can be disposed of, or alternatively, if there still a usable volume of content (e.g. fluid, powder) in the vial, and if restrictions pertaining to the specific contents of the vial allow continued use, the vial can be returned to the module. This can be achieved, for example, by the transferring means 725 of the compounding system returning the non or partially used vial to the exit platform; from which the vial can be picked up by the robot arm 721 of the module, optionally, disinfected again and capped, and then placed back in a designated storage location, until further use. In this manner, the non or partially used vial can be returned to storage in the module in a fully automated manner, without involvement of a human operator. The described ability of returning a non or partially used vial from the compounding system into the module may be potentially advantageous in that: a risk of contamination is reduced, since the return process is carried out fully inside hood, without involvement of a human operator; wastage of pharmaceuticals can be reduced, since the vial contents are efficiently used.

In some embodiments, the module comprises only a partial housing or infrastructure, for example including a bottom surface and one more side walls. Optionally, first portion 705, if and when located outside a hood, includes a housing which fully seals it and comprises a bottom portion, side walls and a top ceiling portion; second portion 713, if and when located inside a hood, may include only a bottom portion (and optionally partial side walls) and no top ceiling portion, thereby enabling the air flow and filtering mechanisms of the hood to affect the inner volume of the second portion, reaching environmental conditions similar to those of the rest of the hood (e.g. laminar flow conditions).

In embodiments in which the module is used without a hood, the housing should be constructed to fully envelope the module, allowing for controlling conditions of the inner volume in at least a part of the housing, such as in the second portion of the module. In such case, at least the second portion can include an air flow source (such as for providing laminar flow, circulation of air flow, etc.) and one or more air filters for maintaining clean air conditions.

Figure 9:
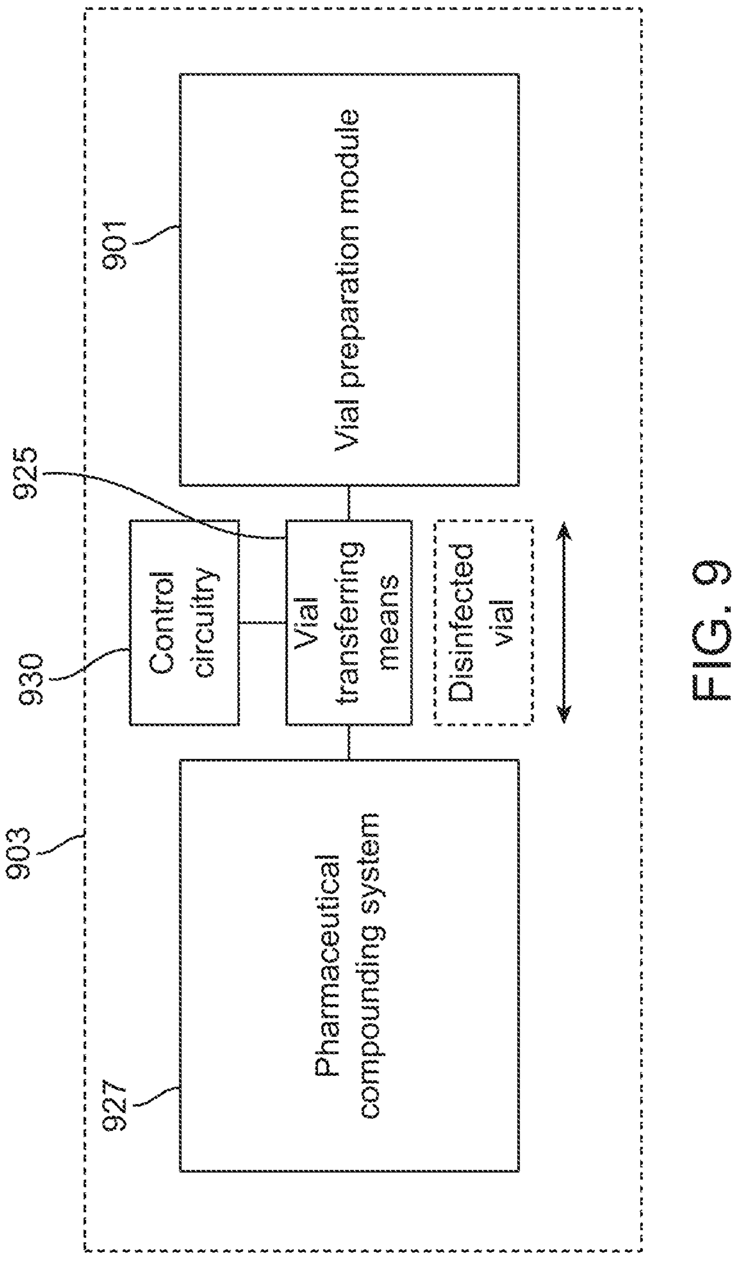
FIG. 9 is a block diagram of a vial preparation module, according to embodiments of the present disclosure.
Figure 10B:
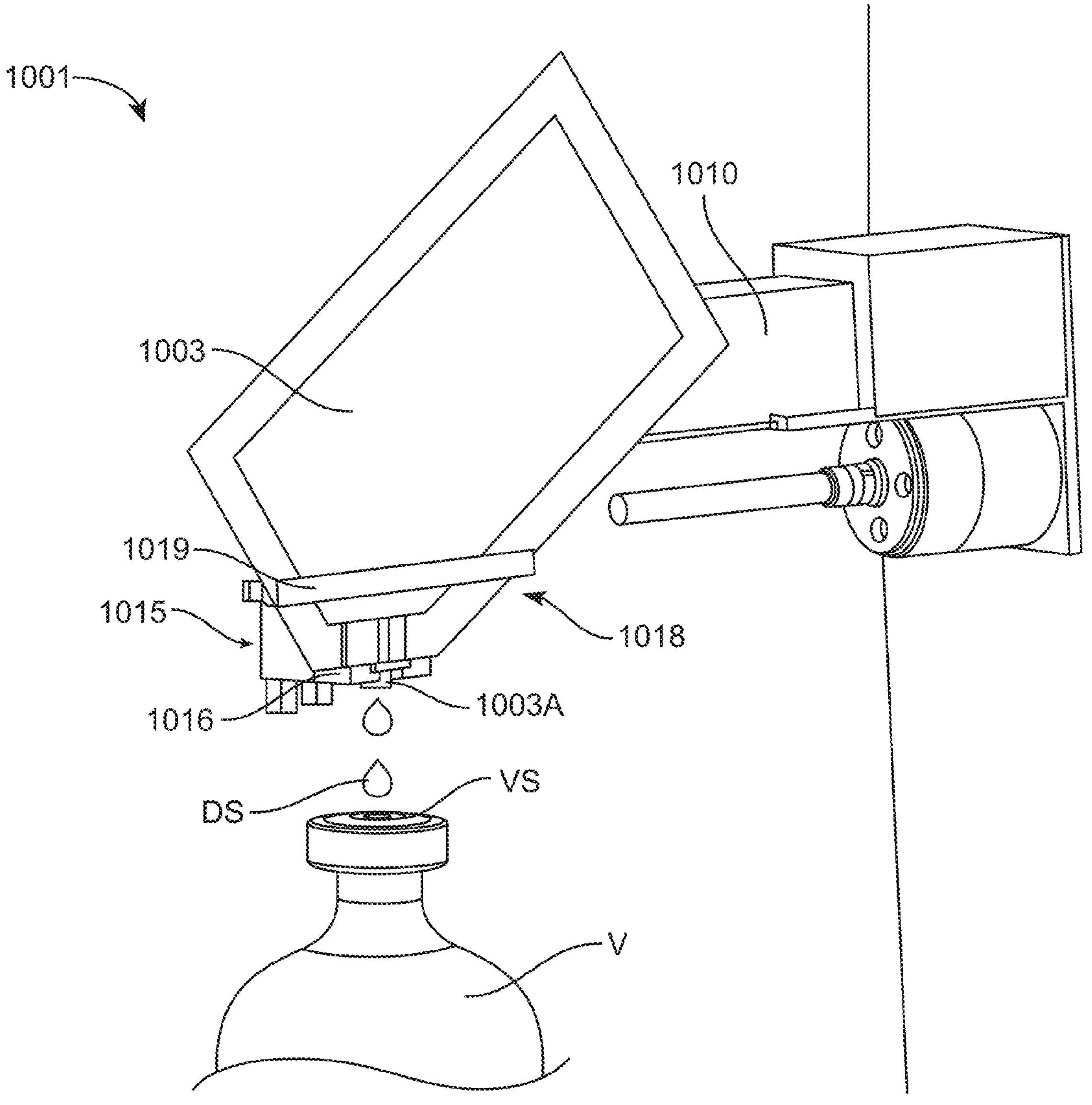
Figure 10C:
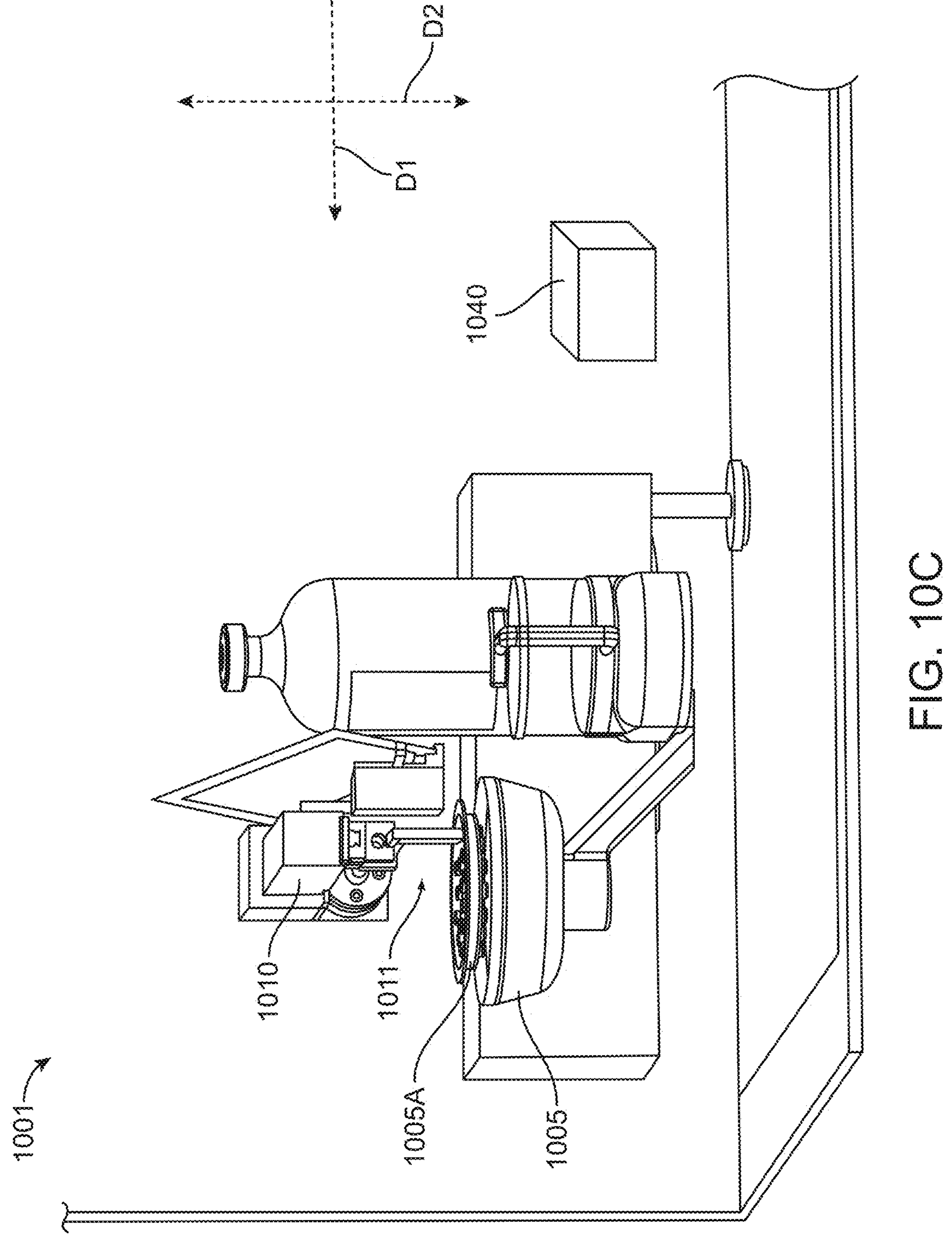
Figure 10D:
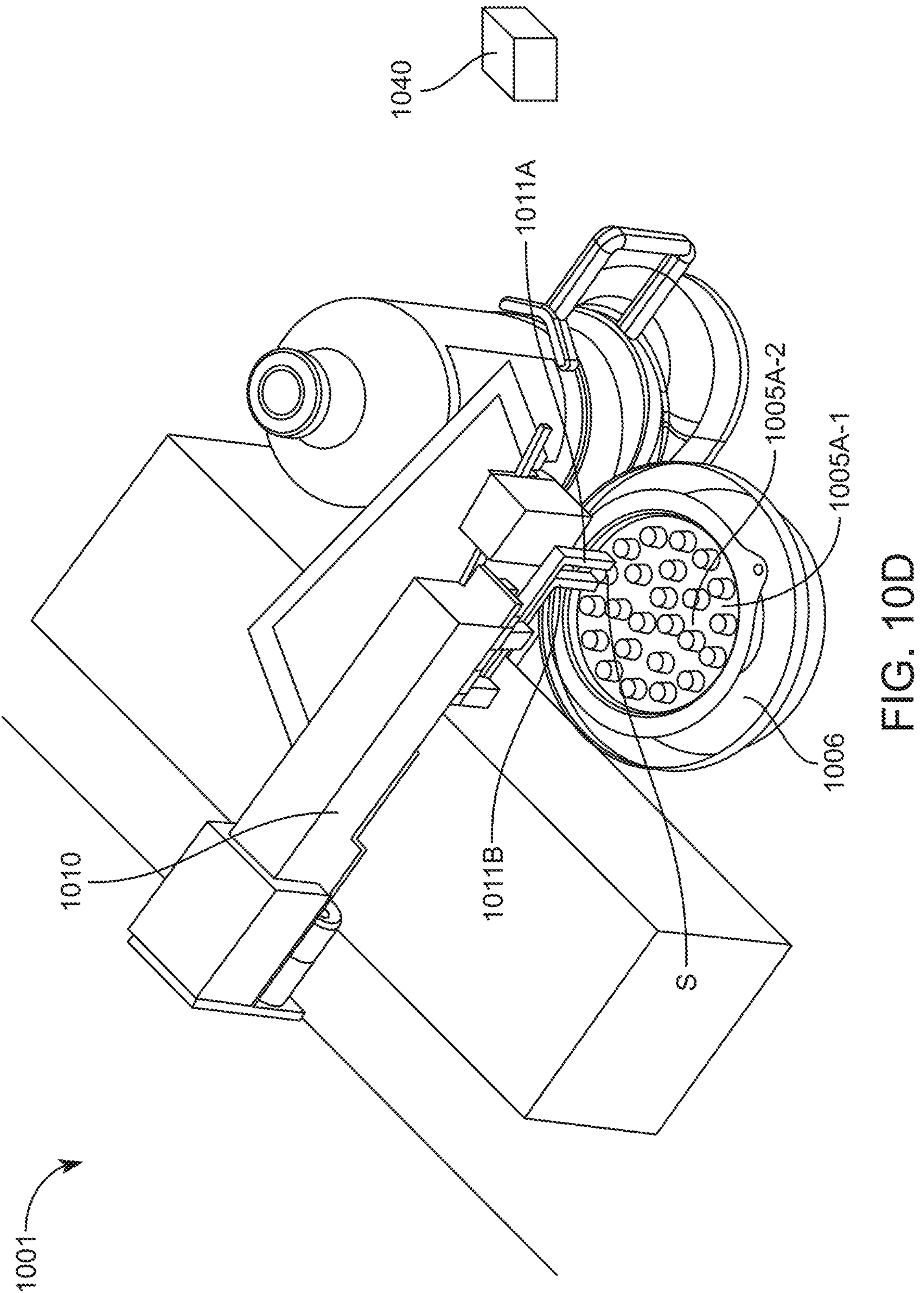
Figure 10E:
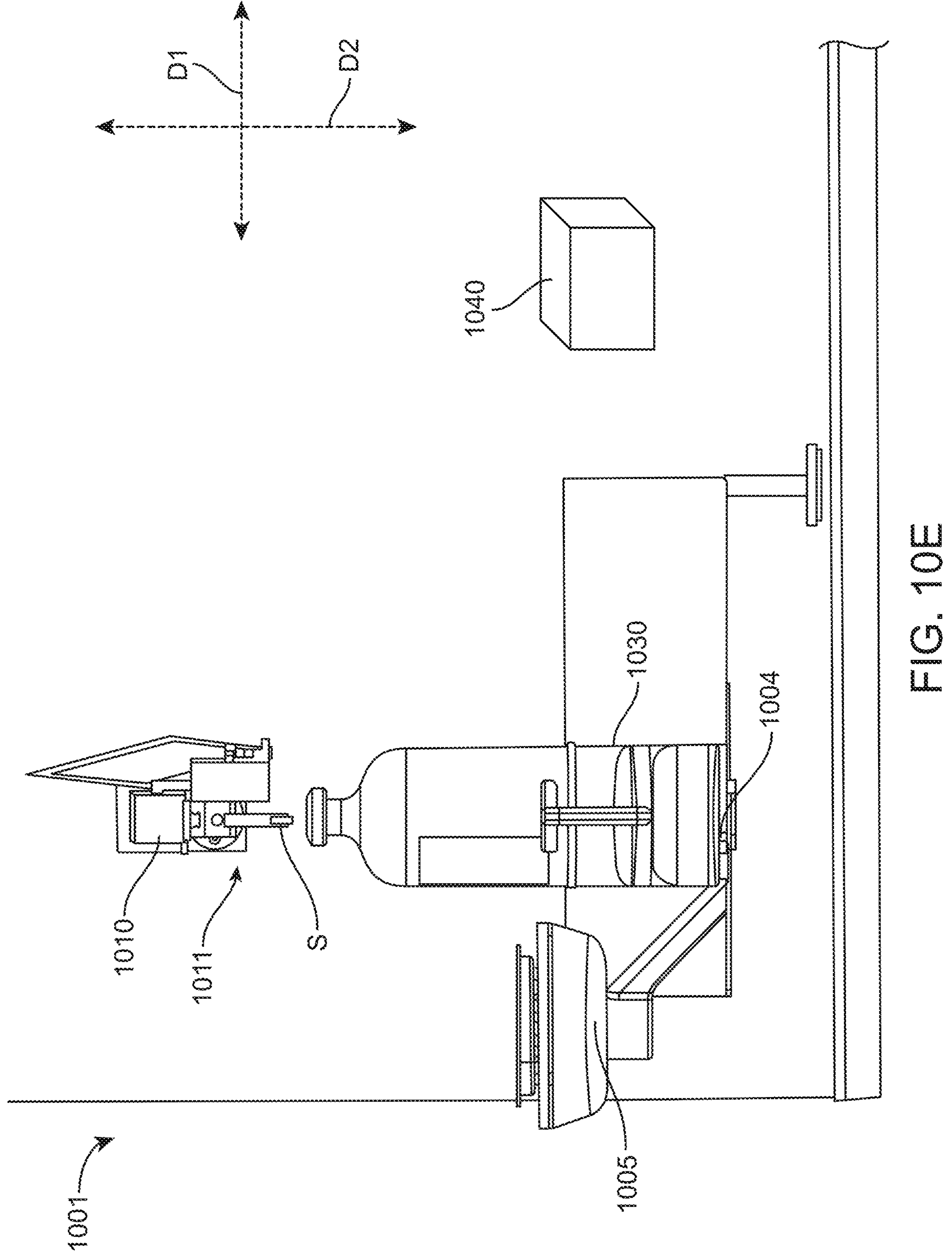
Figure 10F:
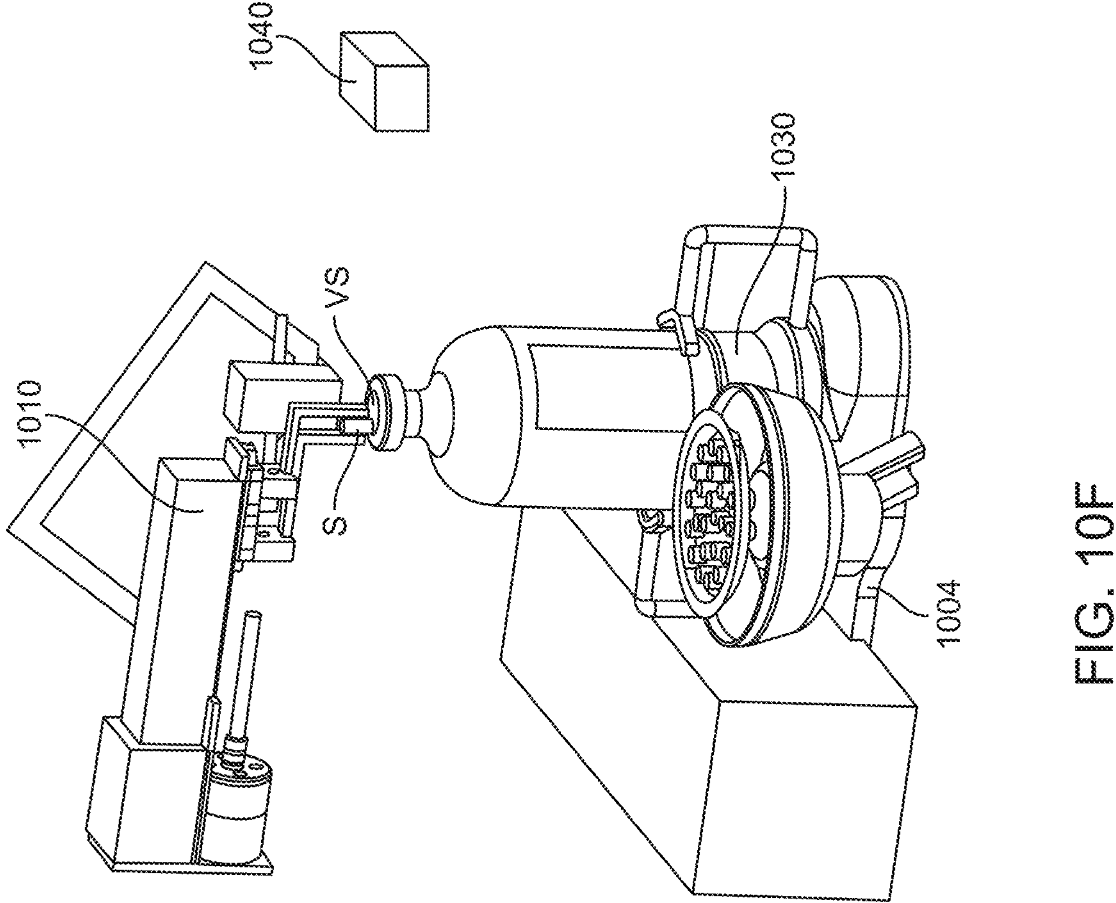
Figure 10G:
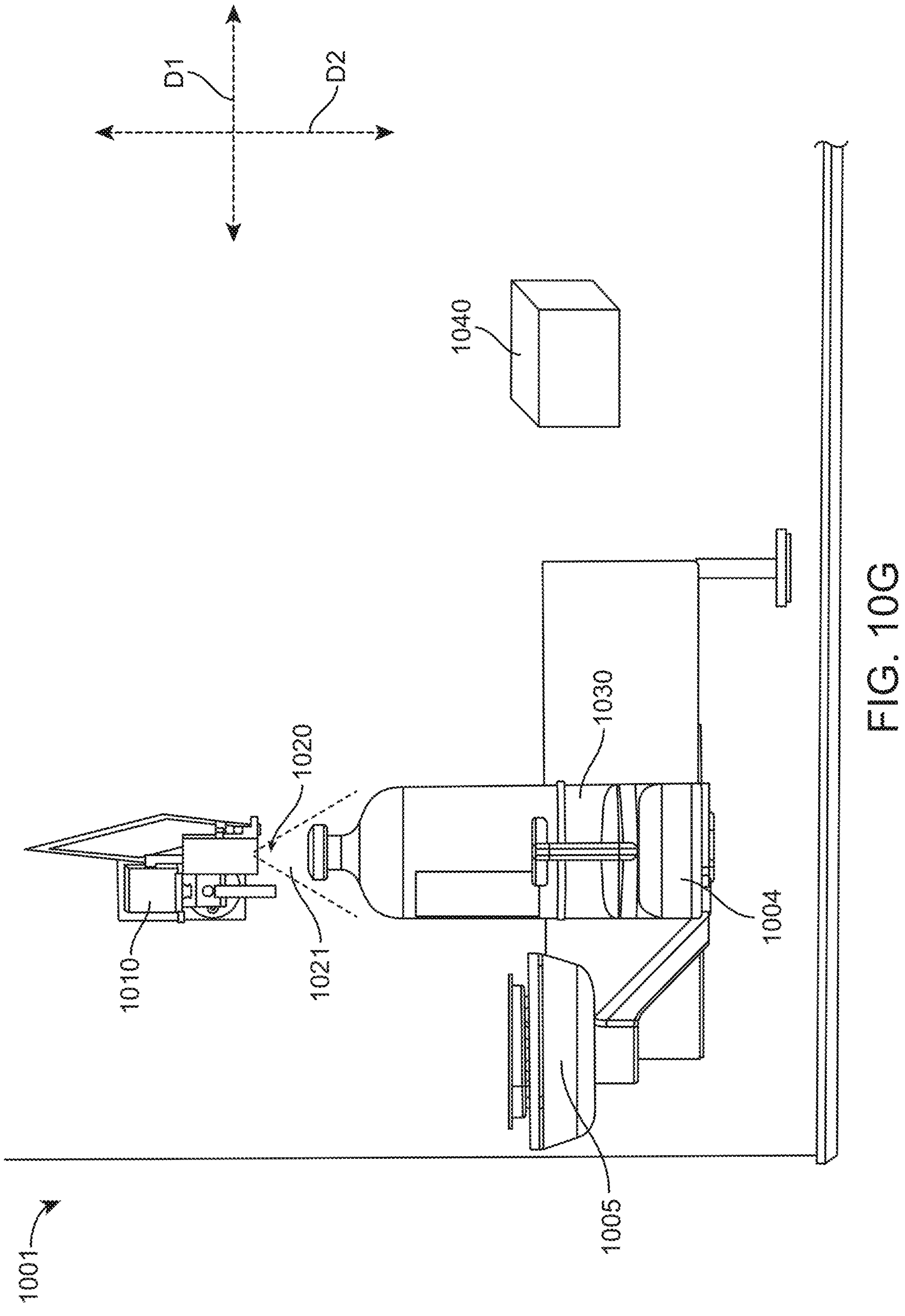

FIG. 9 illustrates another example of an automated vial preparation and drug compounding arrangement comprising an automated vial preparation module 901, and an automated pharmaceutical compounding system 927 that, when in use, performs drug compounding. The automated vial preparation module 901 can be a vial preparation module according to any example of the vial preparation modules described herein, which in general prepares vials for being used in pharmaceutical compounding. The automated vial preparation and drug compounding arrangement further comprises a transferring means 925 for transferring a vial prepared by the automated vial preparation module 901 at least from the automated vial preparation module 901 to the automated pharmaceutical compounding system 927 for further handling by the automated pharmaceutical compounding system 927.

In general, the automated pharmaceutical compounding system 927 can perform any operation related to drug compounding, for example operations including at least one of dilution of the prepared vial, reconstitution of the prepared vial, transfer of drug to and/or from the prepared vial, and agitating the prepared vial. Accordingly, the automated pharmaceutical compounding system can comprise a dilution module operable for performing the dilution of the prepared vial and/or reconstitution of the prepared vial. In some examples, the automated pharmaceutical compounding system can comprise a shaking module (for example, in the form of a vial manipulator) operable for performing said drug compounding including agitating the prepared vial.

The automated vial preparation and drug compounding arrangement further comprises a control circuitry 930 that maneuvers the transferring means 925 in a controlled manner to perform its operations. The control circuitry 930 can constitute a part of any one of the automated vial preparation module 901 and the automated pharmaceutical compounding system 927, can be external to both the automated vial preparation module 901 and the automated pharmaceutical compounding system 927.

In general, the transferring means can include a robotic arm, transfer belt, platform, chain mechanism, carousel, or any other equivalent structure, operable (for example, by a control circuitry) for transferring the vials between the automated vial preparation module 901 and the automated pharmaceutical compounding system 927. The transferring means can transfer the prepared (disinfected) vials from the automated vial preparation module 901 to the automated pharmaceutical compounding system 927, and the partially (or even fully) used vials by the pharmaceutical compounding system 927 from the automated pharmaceutical compounding system 927 to the automated vial preparation module 901. For instance, a control circuitry can determine the amount of vial content used or remaining in the prepared vial after the use of the prepared vial by the automated pharmaceutical compounding system 927, and based thereupon determine whether the prepared vial is to be returned to the automated vial preparation module 901, and if so, then transfer the vial to the automated vial preparation module 901. This may be especially relevant when the vial preparation module 901 includes vial storage positions.

In some examples, the automated vial preparation module 901 can comprise an exit platform from which the transferring means can pick up the prepared vials for transferring the prepared vials to the automated pharmaceutical compounding system 927. In some examples, the automated vial preparation module 901 can comprise vial storage for storing pre-prepared vials and/or prepared vials, and the transferring means can be configured to transfer the pre-prepared vials and/or prepared vials from and/or to the vial storage.

In the example illustrated in FIG. 9, the automated vial preparation and drug compounding arrangement has been shown as including and being positioned within a first hood 903 having a controlled inner volume (maintaining clean air), in which both of the automated vial preparation module 901 and the automated pharmaceutical compounding system 927 are positioned. It is to be understood herein that in some examples, the automated vial preparation module 901 and the automated pharmaceutical compounding system 927 can be positioned within respective separate hoods or housings. For instance, the automated vial preparation and drug compounding arrangement can include a first hood in which the automated vial preparation module 901 can be positioned and a second hood in which the automated pharmaceutical compounding system 927 can be positioned. The transferring means 925 can act as an interface between the two hoods for transfer of vials. It is to be understood herein that in some examples, the automated vial preparation and drug compounding arrangement may not include a hood. In some examples, the vial preparation module and the compounding system may be modular in the sense that each of them can be selectively placed in an existing hood, for use separately or together. In some examples, each of the vial preparation module and compounding system may include its own dedicated housing. In some examples, the housing may provide a controlled environment (in which, for example, one or more of airflow circulation, temperature, humidity, lighting and/or other conditions are controlled).

FIGS. 10A-G show an example of a vial preparation module 1001, according to embodiments of the present disclosure. The vial preparation module 1001 can be operable to prepare vials prior to being used in drug compounding. The preparation can generally include cleaning, for example, disinfecting at least a septum of the vial. Disinfection can be performed by at least one of: applying a disinfecting solution (for example, an alcohol based solution) on the septum, and wiping the septum by at least one (at least a first) swab. The wiping can include friction-based contact of a swab with the septum, for microbial reduction.

Accordingly, in general, a vial preparation module can include a vial mount for receiving (and optionally holding) a vial to be prepared, and a manipulator for performing disinfection of the vial. In some examples, the manipulator can include a swab gripper which can grip a swab that can be used for wiping the septum. In some examples, the manipulator can include a disinfecting solution reservoir holder for holding a disinfecting solution reservoir (interchangeably referred to herein as reservoir) storing a disinfecting solution, and dropper mechanism for selectively dripping the disinfecting solution from the reservoir on the vial.

The dropper mechanism can include any structure suitable to drop/drip the solution onto the vial. For instance, in some examples, the dropper mechanism can directly engage the reservoir to drip (by dropping the drops, spraying, mist formation, etc.) the solution directly from the reservoir on the septum. In some examples, the dropper mechanism can include a swab gripper to pick up a swab, soak it in the solution (for example, by dipping the swab in the reservoir or by any other equivalent manner such as spraying the solution on the swab), position the soaked swab above the septum and drip (for example, by squeezing the swab, shaking the swab, by dropping the drops, spraying, mist formation, etc.) the solution on the septum.

A vial preparation module can include a control circuitry for maneuvering at least one of the vial mount and the manipulator with respect to the other for performing the disinfection of the vial. Accordingly, the vial preparation module can be operated to perform an automated vial preparation method including the steps of receiving a vial on a vial mount and disinfecting the septum by at least one of: applying a disinfecting solution (for example, an alcohol based solution) on the septum, and wiping the septum by at least one (at least a first) swab. It is to be understood herein that the description of the automated vial preparation module can apply to the corresponding automated method for vial preparation.

In the example illustrated in FIGS. 10A to 10G, the automated vial preparation module 1001 comprises a manipulator 1010 and a vial mount 1030. The manipulator 1010 has a swab gripper 1011 for gripping at least a first swab, for example from a swab cartridge. The vial preparation module 1001 further comprises a disinfecting solution reservoir holder 1015 for holding a disinfecting solution reservoir, for example the reservoir 1003 which in the illustrated example is a pouch. The disinfecting solution reservoir holder 1015 is attached to the manipulator 1010 and is moveable therewith.

In the illustrated example, the vial mount 1030 has a top mount surface 1031, onto which a vial, for example vial V can be placed in an upright orientation, as shown. For the purposes of the present description, an upright orientation of a vial may include an orientation in which a vial can be placed on a flat surface without falling over without any support or hold by an external element, and/or an orientation in which the contents of the vial are generally leveled and not tilted, and/or an orientation in which the vial long axis is substantially perpendicular to a surface on which the vial is located, with the vial septum facing upwards (in a direction opposite the surface). In some examples, the vial can be held (e.g. restricted by mechanical means, such as one or more arms) on the vial mount. In some examples, the vial can be held while not being in an upright orientation.

The vial mount 1030 is moveable along a first linear axis D1, which in the illustrated example is the width axis of the module 1001, for example together with a mounting base 1004 on which the vial mount 1030 is mounted. The mounting base 1004 can be connected to and moveable by a linear movement mechanism, for example a motor, a linear drive, or any other equivalent mechanism operable to move a base in a linear direction.

The manipulator 1010 is moveable along a second linear axis D2, which in the illustrated example is the height axis of the module 1001. The manipulator 1010 can be connected to and moveable by a linear movement mechanism, for example a motor, a linear drive, or any other equivalent mechanism operable to move the manipulator in a linear direction. In some examples, the manipulator is movable (e.g. slidable) along a track.

The control circuitry (not shown) can maneuver the vial mount 1030 (together with a mounting base 1004) along the first linear axis D1 to position the mounting base at a mounting base first position (FIGS. 10E and 10F) along the first axis D1, in which the vial mount 1030 (and the vial positioned thereon) is at least partially vertically aligned with the swab gripper 1011.

The control circuitry (not shown) can maneuver the manipulator 1010 along the second linear axis D2 to position the manipulator 1010 at a manipulator raised position along the second linear axis D2 (FIGS. 10A, 10E, and 10G) and a manipulator first lowered position (FIG. 10F) along the second axis D2, corresponding to the mounting base first position along the first axis D1.

The control circuitry (not shown) can maneuver at least one of the manipulator 1010 and the vial mount 1030 to bring a swab gripped at the swab gripper 1011 into contact with the septum of the vial (for example, FIG. 10F) and wipe the septum with the swab, for example in any pattern, some of which are described herein. It is to be understood herein that the direction of movement of the manipulator 1010 and the vial mount 1030 is exemplary in the illustrated example, and in some examples, the control circuitry (not shown) can maneuver at least one of the manipulator 1010 and the vial mount 1030 in any directions for performing their respective operations.

In the example illustrated in FIGS. 10A to 10G, the automated vial preparation module 1001 further comprises a swab cartridge holder 1005 for holding a swab cartridge (including a swab stock, i.e. multiple swabs), for example 1005A. The swab cartridge holder 1005 is attached to and moveable with the mounting base 1004. In some examples, the swab cartridge holder 1005 can be moveable independently of the mounting base 1004, for example by a respective movement mechanism.

In general, the control circuitry can be operable for maneuvering at least one of the swab cartridge holder and the swab gripper with respect to the other for using the swab gripper to pick up a swab from a swab cartridge held at the swab cartridge holder.

In the illustrated example, the control circuitry (not shown) can maneuver the mounting base 1004 along the first linear axis D1 to position the mounting base 1004 at a mounting base second position (FIGS. 10C and 10D) along the first axis D1, in which the swab cartridge holder is at least partially vertically aligned with the swab gripper 1011, so that the swab gripper 1011 can engage a swab in the cartridge and pick up the swab. The control circuitry (not shown) can maneuver the manipulator 1010 along the second linear axis D2 to position the manipulator 1010 at a manipulator second lowered position (FIGS. 10C and 10D) along the second axis D2, corresponding to the mounting base second position along the first axis, so that the swab gripper 1011 can pick a swab from the swab cartridge held at the swab cartridge holder.

The swab gripper 1011 has two swab gripping elements 1011A and 1011B, which in the illustrated example are formed as rods and together constitute a clamp or tweezer like structure, extending from the manipulator in the direction of the vial mount. The control circuitry can control a movement mechanism, for example a motor, connected to at least one of the swab gripping elements 1011A and 1011B to change a distance between them, to grip a swab. As can be best seen in FIG. 10D, the swab gripper 1011 is aligned with the outer circle 1005A-1 of the swab cartridge 1005A. At this position, the control circuitry can control the swab gripping elements 1011A and 1011B to change a distance between them, and to grip a swab, for example a swab S. It is to be understood herein that as clear from FIG. 10D, the swab cartridge 1005A can be rotated in the position shown in FIG. 10D such that the swab gripper 1011 can access each of the swabs in the outer circle 1005A-1. The swab cartridge 1005A can be moved along the first axis D1 (together with the cartridge holder 1005 and mounting base 1004) to align the inner circle 1005A-2 (and all the circles in the same manner) under the swab gripper 1011. Thus, the swab gripper 1011 can access each circle, and by rotating the swab cartridge in each such position, each swab in each circle of the swab cartridge 1005. Generally, the swab cartridge geometry can be defined as including multiple co-centric rings (referred to above as circles) along which the swabs are located.

Accordingly, the swab cartridge holder 1005 comprises a cartridge mount 1006 onto which a swab cartridge (for example, 1005) is mountable, and a swab cartridge motor (not visible) for rotating the cartridge mount 1006 and the swab cartridge together therewith.

In the example illustrated in FIGS. 10A to 10G, the automated vial preparation module 1001 further comprises the disinfecting solution reservoir holder 1015 for holding a disinfecting solution reservoir, for example the reservoir 1003, which in the illustrated example is a pouch having squeezable walls (for example, similar to an IV bag). The disinfecting solution reservoir holder 1015 comprises a reservoir gripper 1016 for, at least during the dripping of the solution from the reservoir, stabilizing at least an opening 1003A of the disinfecting solution reservoir 1003 via which the disinfecting solution drips from the disinfecting solution reservoir. The reservoir gripper 1016 is in the form of a slot in which the opening of the reservoir 1016 is received and stabilized, for example due to corresponding size of the slot and the opening of reservoir. The remaining portion of the reservoir 1003 can be supported by other supporting portions 1017 of the disinfecting solution reservoir holder 1015. The reservoir can be removed, replaced, and/or refilled once empty or the remaining volume is below a threshold.

The dropper mechanism 1018 is generally operable to selectively drip the disinfecting solution from the disinfecting solution reservoir held at the disinfecting solution reservoir holder. For instance, the control circuitry can maneuver the dropper mechanism 1018 for dripping a controlled volume of the disinfecting solution DS from the disinfecting solution reservoir 1003 held at the disinfecting solution reservoir holder 1015 onto a septum VS of the vial V to apply the disinfecting solution on the septum.

In some examples, a high enough volume of the disinfecting solution can be applied to ensure that the disinfecting solution accumulates on the septum, and in general can flood the septum. When a sufficient volume of disinfecting solution is dispensed onto the septum, the disinfecting solution may enter a gap between the septum and a cover of the vial covering partially the septum. In this manner, even non-exposed or less exposed surfaces of the septum (which may be hard to access by direct contact) can be disinfected by the solution. In some examples, a sufficient volume of disinfecting solution released from the reservoir includes at least two, three, four, five (or any other number of) drops of the disinfecting solution (optionally, the number of drops depends on an average volume of each drop).

In general, a dropper mechanism can comprise a dropper actuator that at least selectively engages the disinfecting solution reservoir, and the control circuitry can be operable for maneuvering the dropper actuator for dripping the controlled volume of the disinfecting solution from the disinfecting solution reservoir. The dropper actuator can engage with the opening (for selectively opening and closing the opening) of the reservoir or other parts of the reservoir. The dropper actuator can shake the reservoir causing the solution to drip. In some examples, the dropper actuator may constitute a mechanism which shakes or squeezes a dipped, soaked swab on the septum or directly above the septum. In some examples, the dropper actuator can be a structure suitable for applying a force onto the reservoir, for example, squeezing the reservoir when the reservoir has squeezable walls (e.g. provided as a pouch). In some examples, the dropper actuator can be moved with respect to the disinfecting solution reservoir for dripping the controlled volume of the disinfecting solution from the disinfecting solution reservoir. In some examples, the dropper actuator can apply a controlled force on the disinfecting solution reservoir for dripping the controlled volume of the disinfecting solution from the disinfecting solution reservoir. In some examples, the dropper actuator can slide along at least a part of the disinfecting solution reservoir for dripping the controlled volume of the disinfecting solution from the disinfecting solution reservoir.

In the illustrated example, the dropper mechanism 1018 includes dropper arms 1019 that can slide along the walls of the reservoir (pouch) 1003 to cause or promote the release of a controlled volume of the disinfecting solution DS from the disinfecting solution reservoir 1003. The control circuitry can control a movement mechanism (for example, motor or drive) connected to the dropper arms 1019 to maneuver the dropper arms 1019.

The disinfecting solution reservoir holder 1015 is attached to the mounting base 1004, and the control circuitry can maneuver the mounting base 1004 along the first linear axis D1 to position the mounting base 1004 at a mounting base third position (FIGS. 10A and 10B) along the first axis D1, in which the disinfecting solution reservoir holder is at least partially vertically aligned with the vial mount (and the vial V positioned thereon), so that the disinfecting solution can be dropped on the vial VS. The control circuitry can maneuver the manipulator 1010 along the second linear axis D2 to position the manipulator 1010 at a manipulator third lowered position (FIG. 10B) along the second axis D2, corresponding to the mounting base third position along the first axis, to adjust a distance between the septum and the reservoir to avoid spillage of the solution.

In some examples, the disinfecting solution reservoir holder 1015 can be moveable independently of the mounting base 1004, for example via a corresponding movement mechanism.

In the example illustrated in FIGS. 10A to 10G, the automated vial preparation module 1001 further comprises a UV radiation source (or a means for UV radiation source) 1020 attached to the manipulator 1010. In some examples, the UV radiation source can be independent of the manipulator 1010 (for example, mounted at a different location in the module).

In general, the control circuitry can be operable for maneuvering at least one of the vial mount and the UV radiation source with respect to the other for exposing the septum VS to the UV radiation (depicted by lines 1021 in FIG. 10G) emitted from the UV radiation source 1020.

In the illustrated example, the control circuitry can maneuver the mounting base 1004 along the first linear axis D1 to position the mounting base 1004 at a mounting base fourth position (FIG. 10G) along the first axis D1, in which the vial mount 1030 (and the vial placed thereon) is at least partially vertically aligned with the UV radiation source. The control circuitry (not shown) can maneuver the manipulator 1010 along the second linear axis D2 to position the manipulator 1010 at a manipulator fourth lowered position along the second axis D2, corresponding to the mounting base fourth position along the first axis, so as to adjust the distance between the UV radiation source and the septum of the vial.

It is to be understood herein that the manipulator lowered positions can be based on the heights of the vial mount, vial, swab cartridge holder, disinfecting solution reservoir holder, UV radiation source, and/or swab gripper. Accordingly, based thereupon, one or more the manipulator first, second, third, and fourth lowered positions can be same as any other of the manipulator first, second, third, and fourth lowered positions or the manipulator raised position.

In some examples, a vial preparation module can include a transferring means (for example, a robotic arm) that can perform at least one of the following operations:

placing a vial on the vial mount;
removing a vial from the vial mount;
de-cap a vial;
picking a vial adaptor from a blister; and
mounting a vial adaptor on the vial.

It is to be understood herein that the transferring means can be in accordance with any example of the transferring means described herein above and the corresponding description thereof can apply to the transferring means. For example, the transferring means can include a cap removal tool, a vial gripper, and/or a vial adaptor gripper. The transferring means may include a robotic arm. In an example, such robotic arm can include articulation joints and at least a gripper at its distal end.

In general, the control circuitry can maneuver at least one of the vial mount and the swab gripper (together with the manipulator) to bring the swab and the septum of the vial into contact with each other, and then to wipe the septum by the swab. The wiping can be performed in any pattern including rotation, linear movement, spiral movement, pivoting, etc., of the swab and/or the septum with respect to each other. Further, the wiping can be performed by a single swab, two swabs one after other (a first swab and a second swab), or more than two swabs one after other.

Figure 11:
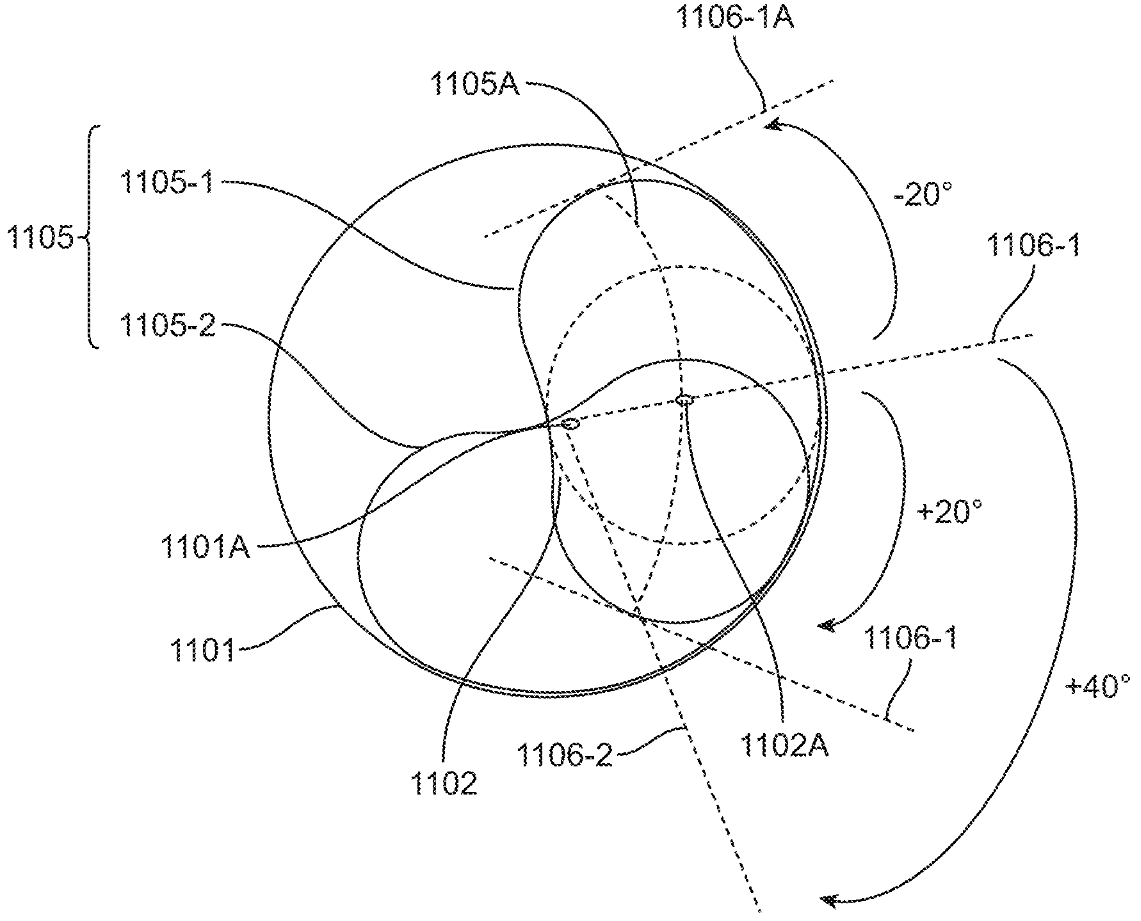
FIG. 11 schematically illustrates an example of a pattern for cleaning a vial septum with a swab, according to embodiments of the present disclosure.

Reference is now made to FIG. 11 schematically illustrating an example of a pattern of wiping a vial septum with a swab. In the illustrated examples, the swab is brought into contact with the septum such that a center of the swab is not aligned with (or is offset with respect to) a center of the septum. For instance, a swab can have a swab surface that contacts the septum, and the center of the swab surface can be offset from the center of the septum, for example as can be seen the best in FIG. 10F.

In FIG. 11, the septum (top surface thereof) is depicted as 1101 having a center 1101A, and a projection of the swab surface (circular in the illustrated example) on the septum 1101 has been depicted as circle 1102 having a center 1102A. An outline of the movement of the swab surface on the septum is depicted by shapes 1105. The center 1102A of the swab surface 1102 is offset from the center 1101A of the septum 1101. In FIG. 11, an outline of the movement of the swab surface on the septum is depicted by shapes 1105, and the dotted line 1105A depict a path of movement of the center 1102A of the swab surface 1102 during wiping.

Once the swab is in contact with the septum 1101, the vial (and thus the septum 1101) can be rotated about a vial longitudinal axis of the vial passing through the center 1101A. The rotation of the vial can include sets of repeated to and fro pivoting movements with respect to corresponding one or more neutral positions by a first predetermined angle, each neutral position corresponding to a set of repeated to and fro pivoting movement. For example, a relative position of the vial (or septum) and the swab on the septum when the swab is first brought in contact with the septum can be referred to as a first neutral position. A neutral position can be depicted by a line connecting the center of the septum 1101A and the center 1102A of the swab surface 1102. Accordingly, the first neutral position is depicted by the line 1106-1.

In a first set of repeated to and fro pivoting movements, the vial is rotated to and fro by a first predetermined angle, which in the illustrated example is 20°, including +20° in a first direction and −20° in opposite direction with respect to the first neutral position 1106-1. The outline (virtual) of the movement of the swab on the septum during the first set of to and fro pivoting movements has been depicted by shape 1105-1 and the path followed by the center 1102A during the first set of to and fro pivoting movements has been depicted by line 1105A. The lines 1106-1A and 1106-1B depict the extents of the to and fro pivoting movements during the first set of to and fro pivoting movements.

After a predetermined time or number of repeated to and fro pivoting movements in the first set, the neutral position can be changed, for example by rotating the vial by a second predetermined angle which in the illustrated example is 40° in the first direction to the second neutral position depicted by the line 1106-2.

A second set of repeated to and fro pivoting movements is performed with respect to the second neutral position 1106-2, in which the vial is rotated to and fro by a first predetermined angle with respect to the first neutral position 1106-2 similarly to the first set of to and fro pivoting movements. The outline (virtual) of the movement of the swab on the septum during the second set of to and fro pivoting movements has been depicted by shape 1105-2. The shapes 1105-1 and 1105-2 represent contact regions in which the swab surface contacts the septum during the first set and second set of movements, and the contact regions may have an overlapping area, as shown. An overlapping area may be advantageous for ensuring that all of the septum surface has been contacted by the swab, and no areas remain unwiped.

The neutral positions can similarly be repeatedly and intermittently changed by rotating the vial by a second predetermined angle until whole 360° rotation is covered and the whole of the septum is wiped with sets of to and fro pivoting movements. Thus, each neutral position can correspond to a respective set of to and fro pivoting movements.

The first and the second predetermined angles can be predetermined and can be executed by control circuitry for example by rotating the vial (for example by rotating the vial mount or a portion thereof). The first predetermined angle can vary between 5 degrees and 60 degrees or other higher or lower values. The second predetermined angle can vary between 10 degrees and 120 degrees or other higher or lower values. The predetermined time of repeating to and fro pivoting movements in a set can be at least 1 second, 2 seconds, 3 seconds, 5 seconds, 10 seconds, or other higher or intermediate values.

In some examples, the wiping can be include linear to and fro movements of the swab and the septum with respect to each other, for example, movements in a lateral direction. In some examples, the wiping can be include linear movements of the swab and the septum with respect to each other, for example to wipe off any contaminants and/or remaining disinfecting solution from the septum to dry off the septum. Such linear movements can be performed with a second swab, or optionally with the same (first) swab. For instance, the swab gripper can be maneuvered to dispose off the first swab (after performance of the wiping described with respect to FIG. 11) in a garbage bin, and to pick up a second swab from the swab cartridge. The linear movements can be performed for example by moving the vial mount along the first linear direction D1 (in FIG. 10F).

In general, a vial preparation module can include an imaging apparatus (or imager) 1040 for imaging at least a vial preparation region, for example the region in which one or more operations of the vial preparation are performed. Based on the images captured by the imaging apparatus, the controller can monitor the positions of various components of the vial preparation module and their operations, as described in detail further below herein.

Figure 12:
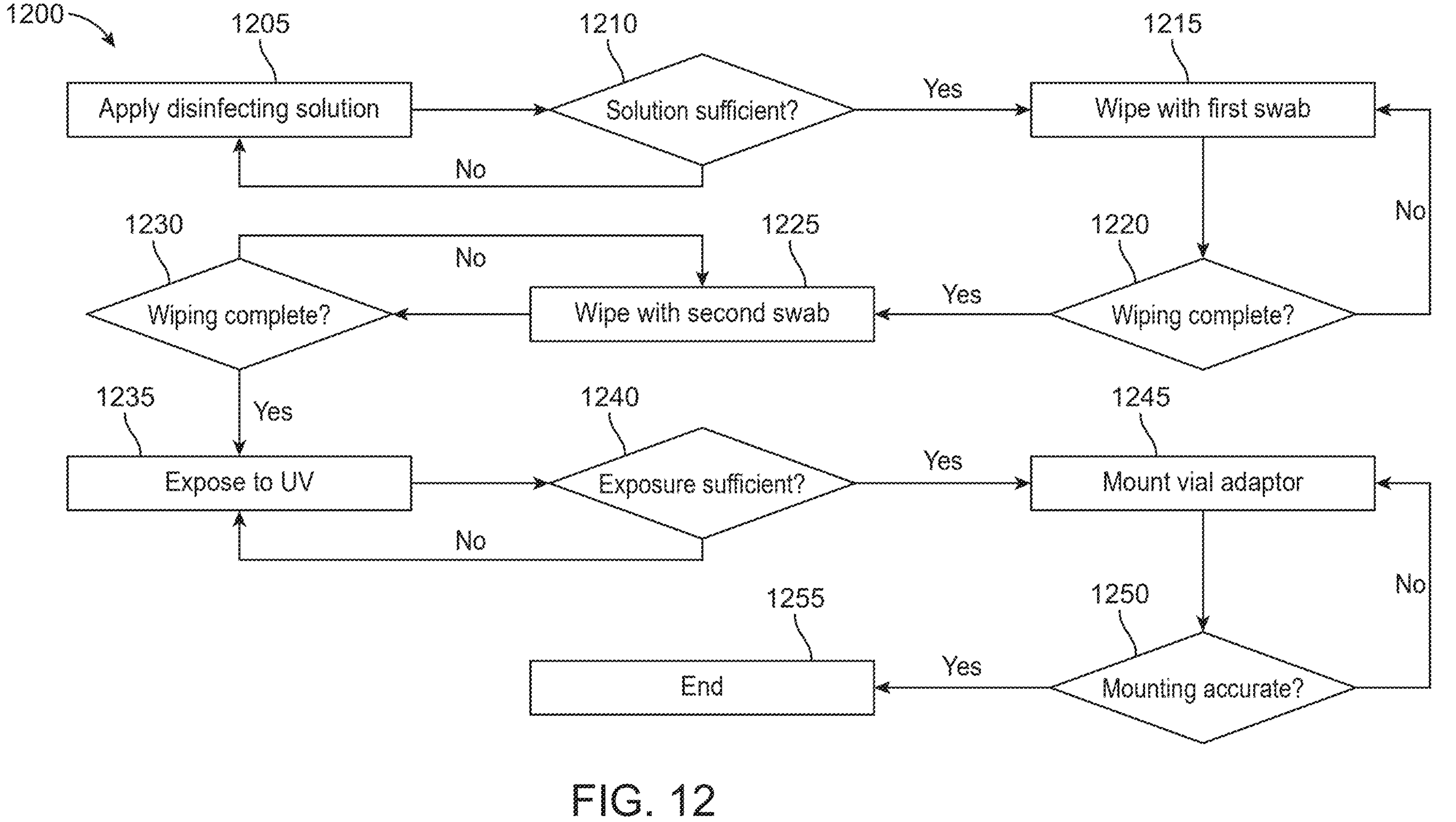
FIG. 12 is another flowchart of an example of a work process carried out by a vial preparation module, according to embodiments of the present disclosure.

FIG. 12 illustrates a flowchart of an automated method 1200 for vial preparation carried out by a vial preparation module, for example the vial preparation modules described herein. The steps of the automated method 1200 can be performed by corresponding structure of the vial preparation modules described herein and thus the corresponding description of the vial preparation modules apply to the automated method 1200 as well. The vial preparation can be performed (by a vial preparation module) within a vial preparation zone, for example on a vial mount, and an imaging apparatus of the vial preparation module can image a field of view including the vial preparation zone. A control circuitry can receive those images, process the acquired images, and monitor, based on the processing, preparation of the vial, for example at least the cleaning of the septum of the vial. The control circuitry can operate the vial preparation module based on the monitoring of the process, i.e., based on real-time feedback generated according to the monitoring.

A vial to be prepared can be positioned on a vial mount and a cap of the vial can be removed. These steps can be performed manually by a user or automatically by a transferring means (robotic arm). At 1205, a disinfecting solution is applied on at least the septum of the vial. The application of the disinfecting solution can be performed in any manner described herein above, or in any other equivalent manner.

At 1210, the application of the disinfecting solution is monitored to determine whether the disinfecting solution is sufficient or not. In monitoring the sufficiency of the disinfecting solution, one or more disinfecting solution related indications can be monitored. The one or more disinfecting solution related indications can include at least one of: a volume of the disinfecting solution released from the reservoir; a volume of disinfecting solution accumulated on the septum of the vial; whether the septum is wet or dry; and whether the volume of the disinfecting solution on the septum is sufficient or not. For instance, upon application of the disinfecting solution, if it is determined that the solution is not sufficient (e.g. if the solution did not accumulate on the septum, if the solution is not clearly visible in an image, if the septum is dry, or the like), step 1205 is performed again (based on the real-time feedback of monitoring), and monitored again until it is determined that the disinfecting solution on the septum is sufficient. Additional options for assessing whether a sufficient amount of disinfecting solution was received on the septum may include counting the drops of the solution dripped on the septum, checking whether the solution has flooded the septum or not, and/or whether the solution has entered between the septum and a cover of the vial partially covering the septum.

Once it is determined that the disinfecting solution on the septum is sufficient in volume, the process moves onto step 1215, at which the septum is wiped with at least a first swab. Wiping can be performed in any manner and according to any of the wiping patterns described herein above.

At 1220, which can be simultaneous with 1215, the wiping of step 1215 is monitored to determine if the wiping is complete or not. In monitoring the wiping, one or more swab related indications can be monitored. The one or more swab related indications can include at least one of: pattern of the movement of the swab on the septum, duration of wiping, accuracy of wiping, contact between the swab and the septum, pressure applied by the swab on the septum, a position of the swab, a relative position of the swab and the septum during wiping, whether the swab is wet or dry, an orientation of the swab with respect to the septum, a time of initiation of a wiping, a duration of wiping. If the wiping is performed in the pattern described above with respect to FIG. 11, then the one or more swab related indications can include at least one of: the first predetermined angle for at least one of the one or more sets, the second predetermined angle for at least one of said repeated changes of the neutral position, duration of the pivoting in at least one of the one or more sets, number of repetitions of the pivoting in at least one of the one or more sets, and total duration of the relative movement between the swab and septum. If wiping is performed in a linear pattern, e.g. the vial septum and/or the swab move linearly sideways (in a lateral direction) with respect to each other, then the one or more swab related indications can include at least one of: a duration of wiping, a number of repetitions of wiping, presence of disinfecting solution on the septum, and contact between septum and the second swab. If wiping is performed to dry off the solution from the septum, then monitoring the wiping can include monitoring whether the septum is dry or not, and wiping is determined as being complete only when the septum is dry.

If at 1220, it is determined that the wiping is not complete and/or not accurate (based on the above-described indications), step 1215 is performed again or continued (based on the real-time feedback of monitoring), and monitored until it is determined that the wiping is complete and accurate. Upon such a determination, the process moves onto step 1225, at which the septum is wiped with at least a second swab.

Steps 1225 and 1230 can include one or more operations of steps 1215 and 1220 and the description thereof applies to steps 1225 and 1230. In some examples, steps 1225 and 1230 may not be performed. In some examples, the wiping pattern and/or purpose of wiping in step 1225 can be different as compared to that of step 1215, and monitoring of such wiping at step 1230 can be according to the wiping pattern and/or purpose of wiping in step 1225.

At 1235, the septum of the vial is exposed to a UV radiation, for example as described herein above. At 1240, which can be simultaneous with 1235, exposure to UV radiation is monitored to determine if the exposure is sufficient or not. In monitoring the exposure, one or more UV related indications can be monitored. The one or more UV related indications can include at least one of: wavelength of the UV radiation, intensity of the UV radiation, duration of the exposure, angle of the exposure, and distance between the septum and source of the UV radiation. For instance, upon or during the exposure, if it is determined that the exposure is not sufficient, the step 1235 is performed again or continued (based on the real-time feedback of monitoring), and monitored again until it is determined that the exposure is sufficient.

Once it is determined that the exposure is sufficient, the process moves onto step 1245, at which a vial adaptor is mounted on the vial, for example by a transferring means.

At 1250, which can be performed simultaneously with 1245, the mounting is monitored to determine whether the mounting of the vial adaptor is accurate or not. In monitoring the accuracy of mounting of the vial adaptor, one or more vial adaptor related indications can be monitored. The one or more vial adaptor related indications can include at least one of: alignment of the vial adaptor with respect to the vial, angle of the vial adaptor with respect to the vial, final position of the vial adaptor on the vial, expiry date of the vial adaptor, and a an assessment if the vial is genuine (for example, based on a label on the blister of the vial adaptors and/or the vial adaptor itself).

If it is determined that the adaptor mounting is not accurate, step 1245 is adjusted (based on the real-time feedback of monitoring), and monitored again until it is determined that mounting is accurate. Once it is determined that mounting is accurate and that the adaptor is correctly and placed and seals the vial septum, the process ends, and the vial can be considered as prepared for use in drug compounding. The method can further include adding a label onto the vial indicating the present date and time and, in some examples, a beyond-use-date of the vial. In some examples, the beyond-use-date may be extended with respect to an original beyond-use-date of the vial. By utilizing controlled, sterile conditions and automated processes for vial preparation, the module may reduce contamination risks compared to manual handling, allowing the potential extending of the beyond-use-date. The precise application of disinfectant, thorough cleaning of the vial septum, and minimal human intervention may allow for a longer period of safe use after initial preparation. The control circuitry may be programmed to determine an appropriate extended beyond-use date based on factors such as the specific drug, previous or future storage conditions, and/or the monitored disinfection process. The exact duration of any beyond-use date extension may also vary depending on applicable regulations, drug stability data, and facility protocols.

The method 1200 can include during or prior to vial preparation process, monitoring one or more vial related indications. For example, the vial related indications can be used to control placement of the vial on the vial mount and/or other operations of the vial preparation, for example that require determination of vial related indications. The one or more vial related indications can include at least one of: alignment of the vial with respect to the vial mount, orientation of the vial on the vial mount, position (for example, a spatial location) of the septum of the vial, position of the vial on the vial mount, identification of a label of the vial, height of the vial, geometry of the vial, content of the vial, movement of the vial and/or the vial mount, and disinfection of the septum of the vial. The vial preparation operations can be performed and/or controlled based on real-time feedback in accordance with the vial related indications.

In some examples, the method 1200 can include delivering and directing an airflow on the vial, for example within a hood having a controlled inner volume, as described herein above. The method can further include monitoring one or more airflow related indications, which can include at least one of: laminarity of the airflow, the timing of first air contact of the airflow at the vial and/or vial adaptor, velocity of the airflow, direction of the airflow, presence of the airflow, and airflow path. The vial preparation operations can be performed and/or controlled based on real-time feedback in accordance with the airflow related indications.

It is to be understood herein that one or more of the above-described steps of the method 1200 can be optional, and only the steps related to cleaning of the septum can be included in the method 1200. In some examples, the cleaning steps can include only steps 1205 and 1210. In some examples, the cleaning steps can include only steps 1215 and 1220. In some examples, the cleaning steps can include only steps 1205, 1210, 1215, and 1220.

FIGS. 13A to 13D show a vial mount that can be used with an automated systems for vial preparations and/or drug compounding. The vial mount described herein below can be used with any automated or semi-automated system in which a vial is required to be positioned and manipulated. For instance, the vial mount described herein below can be used in any or all of the vial preparation modules and/or pharmaceutical compounding systems described herein above.

In general, a vial mount can include a mount top portion including a mount top surface on which a vial can be positioned, for example optionally in an upright orientation, and a mount bottom portion, which can be mounted to a mounting base of the system or module in which the vial mount is used. A first rotary arrangement can be operatively associated (connected so as to co-operate) with the mount top portion and can rotate at least the mount top surface about a central axis thereof. A second rotary arrangement can be operatively associated with the mount bottom portion and can rotate at least the mount bottom portion about the central axis.

Accordingly, a vial mount can have two rotatable portions rotatable about a common axis. The two rotatable portions can be rotatable independently of each other or optionally together. The first and the second rotary arrangements can rotate their respective rotatable components either independently of each other or together with each other, at same or different speeds, and/or in same or opposite directions (clockwise and counter-clockwise). The first rotary arrangement can rotate the mount top surface at different speeds, and/or the second rotary arrangement can rotate the mount bottom portion at different speeds.

Figure 13A:
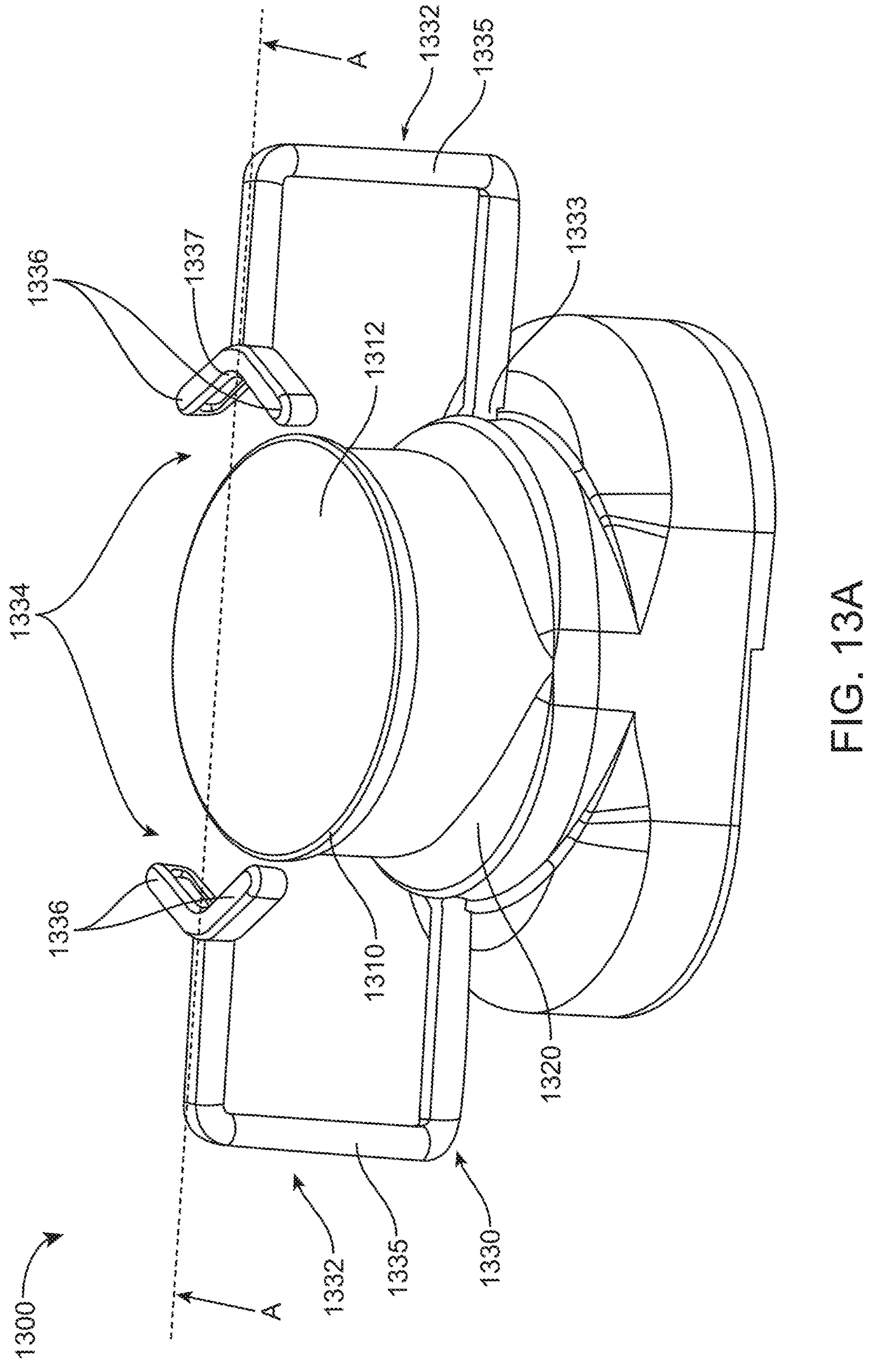
FIG. 13A is a top perspective view of a vial mount, according to embodiments of the present disclosure.
Figure 13B:
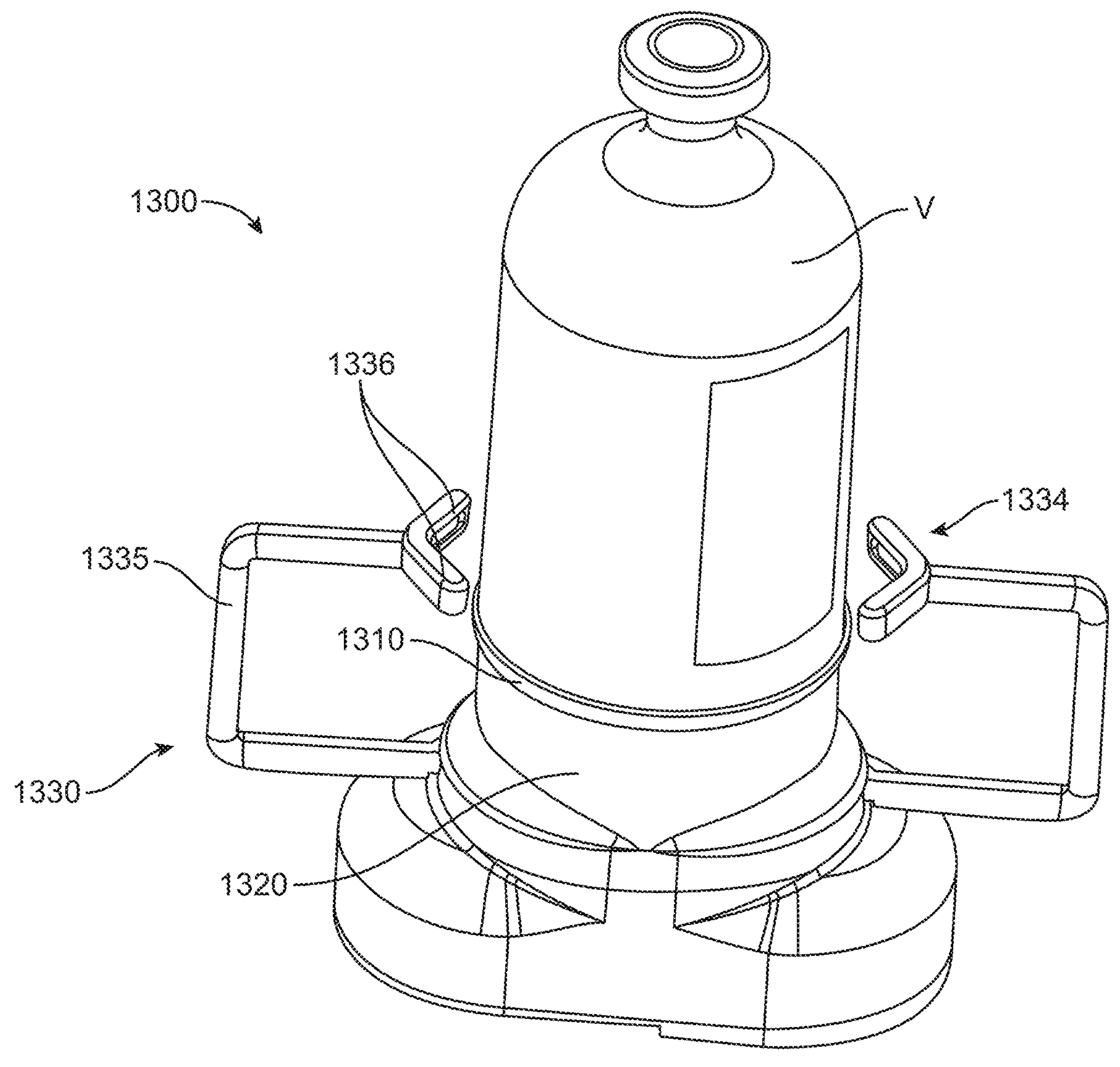
FIG. 13B is the vial mount of FIG. 12A with a vial placed thereon.
Figure 13C:
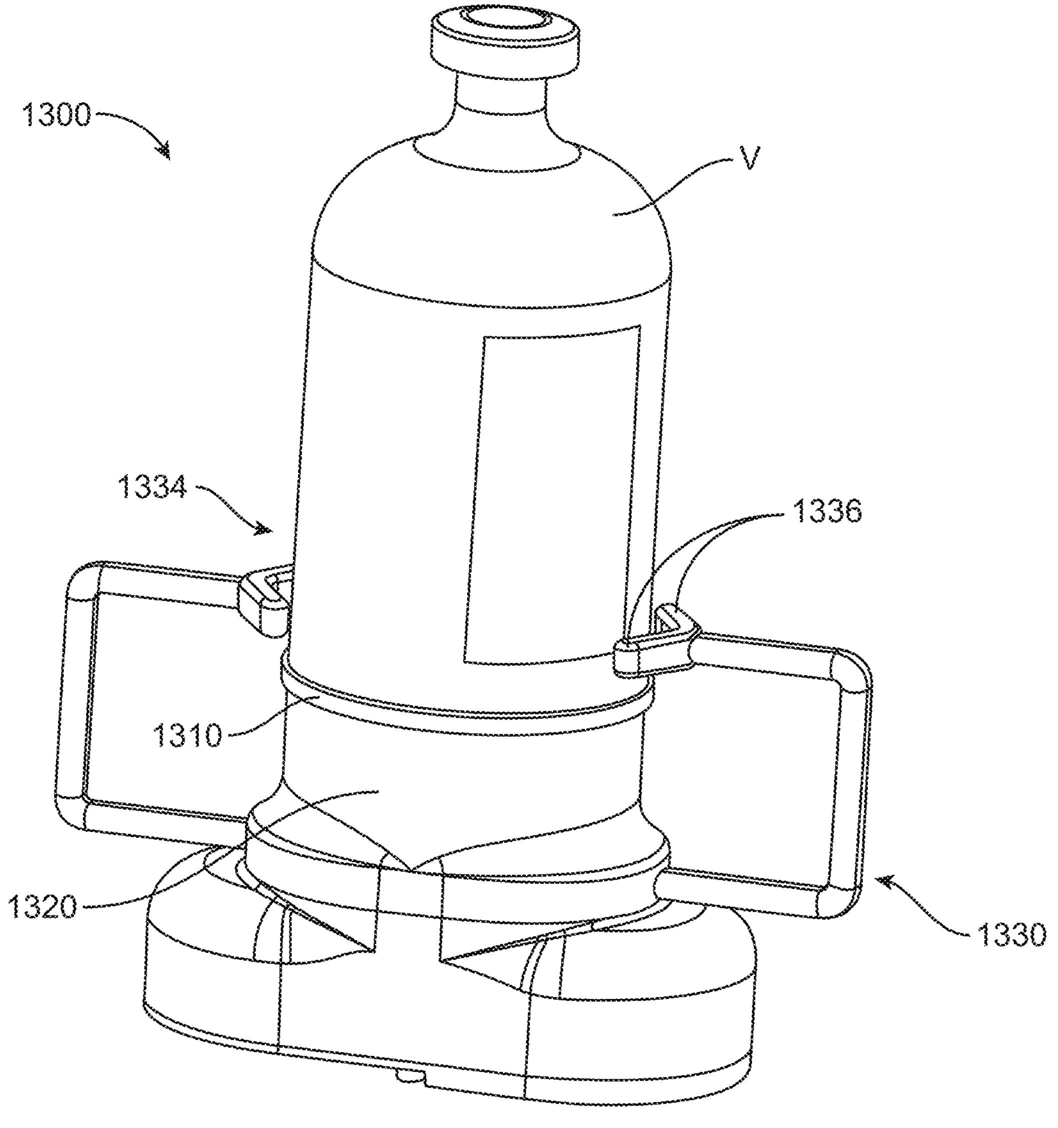
FIG. 13C is the vial mount of FIG. 12B with vial gripper gripping the vial.
Figure 13D:
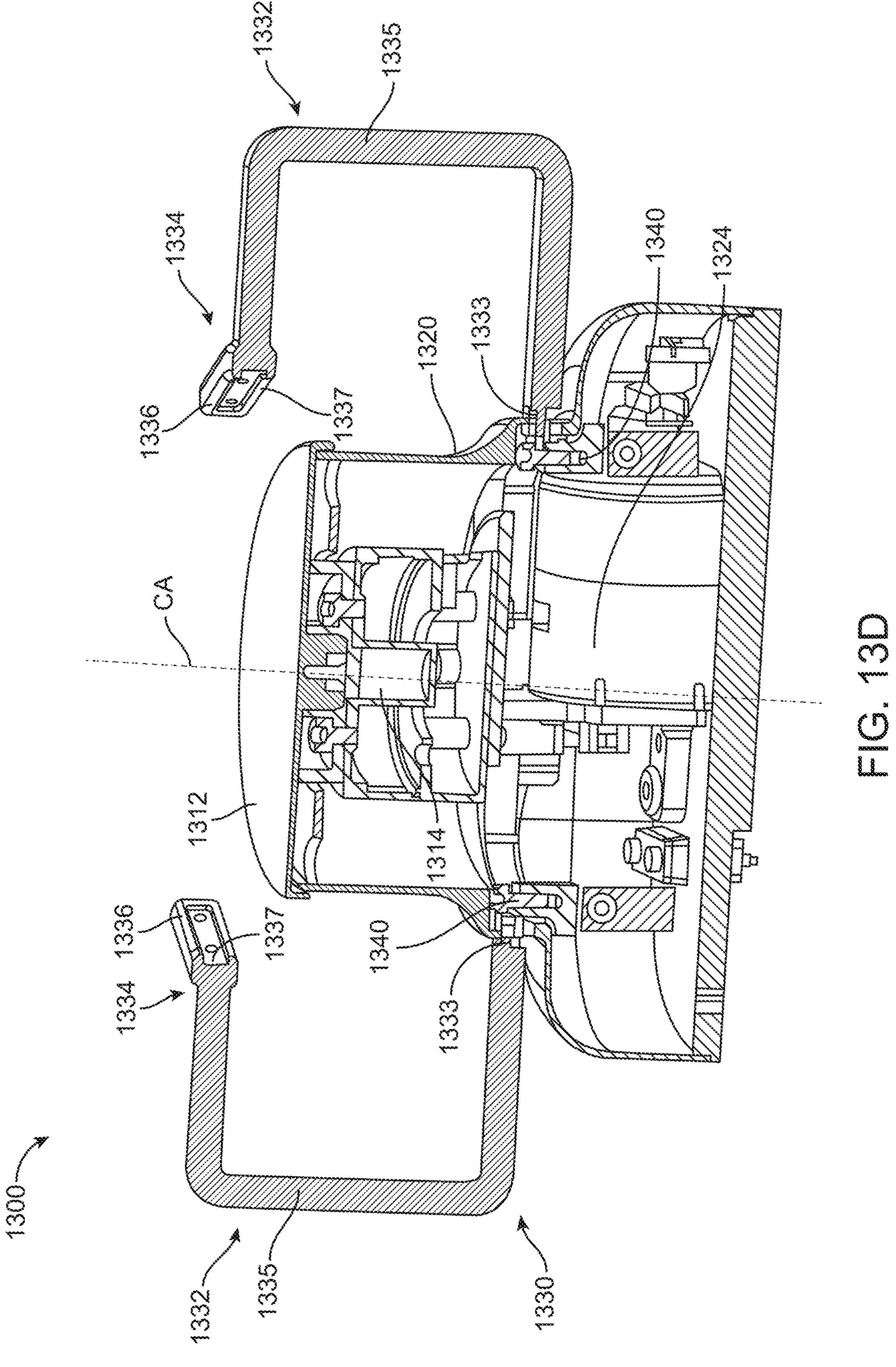
FIG. 13D shows a cross-section taken along line A-A in FIG. 12A.

The first and/or second rotary arrangement can include any mechanical, electrical, or magnetic structure operable to rotate the respective portion of the vial mount. For instance, in some examples, the first rotary arrangement can include a first motor and the second rotary arrangement can include a second motor. In the example illustrated in FIGS. 13A to 13D, the vial mount has been generally designated as 1300, and includes a mount top portion 1310 having a mount top surface 1312 on which a vial V can be positioned, as shown in FIGS. 13B and 13C, mount bottom portion 1320. The first rotary arrangement is constituted by a first motor 1314 connected to the mount top portion 1310 and operable to rotate the mount top surface 1312 about the central axis CA. The second rotary arrangement is constituted by a second motor 1324 connected to the mount bottom portion 1320 and operable to rotate the mount bottom portion 1320 about the central axis CA. In some examples, the second motor 1324 can have a higher maximum torque than that of the first motor 1314.

In general, a vial mount can include a vial gripper for selectively gripping the vial placed on the vial mount. For instance, the vial gripper can be displaceable between a grip state in which the vial gripper grips the vial when the vial is positioned on the mount top surface, and a release state in which the vial gripper releases the vial. The vial gripper can include at least two gripping portions (e.g. gripping arms or clamps) for engaging the vial to grip the vial. For example, the gripping portions can be positioned on opposite sides of the central axis, and thus can engage the vial from opposite side thereby restricting movement of the vial at least in a direction transverse the central axis. The gripping portions can have any structure, shape and size suitable to grip the vial, for example by clamping the vial from opposite sides. The gripping portions can include padded regions or otherwise smooth regions to engage the vial.

At the grip state, the gripping portions can be a gripping distance apart from each other, and at the release state, the gripping portions can be at a release distance, greater than the gripping distance, apart from each other. In some examples, at least one of the gripping portions can be displaced towards and away from the other, for example by a vial gripper actuation mechanism, which can be a motor, a linear drive, or any other structure suitable to move the gripping portions linearly or rotatably towards and away from each other. At least at the grip state, the gripping portions are equidistant from the central axis of the vial mount so as to centralize the vial on the mount top surface. For instance, if the vial is placed on the mount offset of the center of the mount top surface, then displacing the gripping portions to the grip state brings the vial to the centralized location. The gripping portions may slightly push or slide the vial on the mount top surface to centralize the vial.

In the example illustrated in FIGS. 13A to 13D, the vial mount 1300 includes a vial gripper 1330 including two arms 1332 positioned on opposite sides of the central axis CA. Each of the two arms 1332 has a respective connection end 1333 connected to the mount bottom portion 1220, a respective gripping end 1334 constituting a gripping portion 1334, and a respective extension portion 1335 extending between the respective connection end 1333 and the respective gripping end 1334 at least partially along a direction extending between the mount top portion and the mount bottom portion, i.e., the direction along the central axis CA.

The extension portions 1335 are long enough such that the gripping portions 1334 are positioned beyond the mount top surface 1212 so as to engage the vial V when the vial V is placed on the mount top surface 1312.

Each of the gripping portions 1334 includes two vial engaging regions 1336 spaced apart from each other such that the gripping portion 1336 engages the vial V at the vial engaging regions 1336. A portion 1337 between the two vial engaging regions 1336 can engage or not engage the vial depending one a size (diameter) of the vial. For example, if the diameter of the vial is smaller than the distance between the two vial engaging regions 1336, then the portion 1337 can engage the vial. If the diameter of the vial is longer than the distance between the two vial engaging regions 1336, then the vial engaging regions 1336 engage the vial and the portion 1337 does not engage the vial. Accordingly, the vial gripper 1330 can be used to grip vials having different sizes and geometry.

The vial mount 1300 includes a vial gripper actuation mechanism 1340, in the form of motors 1340 connected to the connection ends of the arms 1332. One or both the motors 1340 can move the respective arm 1332 linearly towards and away from the central axis and thus the other arm, thereby displacing the vial gripper between grip state (FIG. 13C) and release state (FIG. 13B)

In some examples, the dimensions of the extension portions 1335 along the direction extending between the mount top portion and the mount bottom portion (along the central axis CA) can be adjustable, for example by a telescopic mechanism or any other equivalent linear extension mechanism. Accordingly, the position of the gripping portions 1334 above the mount top surface 1312 can be adjusted based on a height of the vial positioned on the mount top surface 1312.

In some examples, the gripping portions are controlled based on parameters of a vial being held on the mount, as determined for example from images of the vial. For example, the gripping portions may be approximated closer to each other when it is identified that a vial has a small diameter, and distanced from each other when it is identified that a vial has a large diameter.

In some examples, during the identifying of a label of the vial using the image apparatus, the gripping portions are at the release state so as not to interfere with identifying the label. Optionally, only the mount top portion is rotated during such process. Optionally, prior to identifying the label, the gripping portions are moved to their gripping position so that the vial is centralized on the mount top surface.

In some examples, unitary rotation of the vial mount (inclusive of the top and bottom portions) is carried out when the gripping portions are moved to the gripping distance from each other.

In some examples, the first and second rotary arrangements may differ from each other in the range or limit of rotation velocity. For instance, the first rotary arrangement can be set with a lower rotation velocity limit than the second rotary arrangement.

Rotation of the vial mount can be performed in accordance with the above described cleaning patterns and depending on any respective movement of the swab, when the swab is brought into contact with the vial septum to clean it.

Figure 14A:
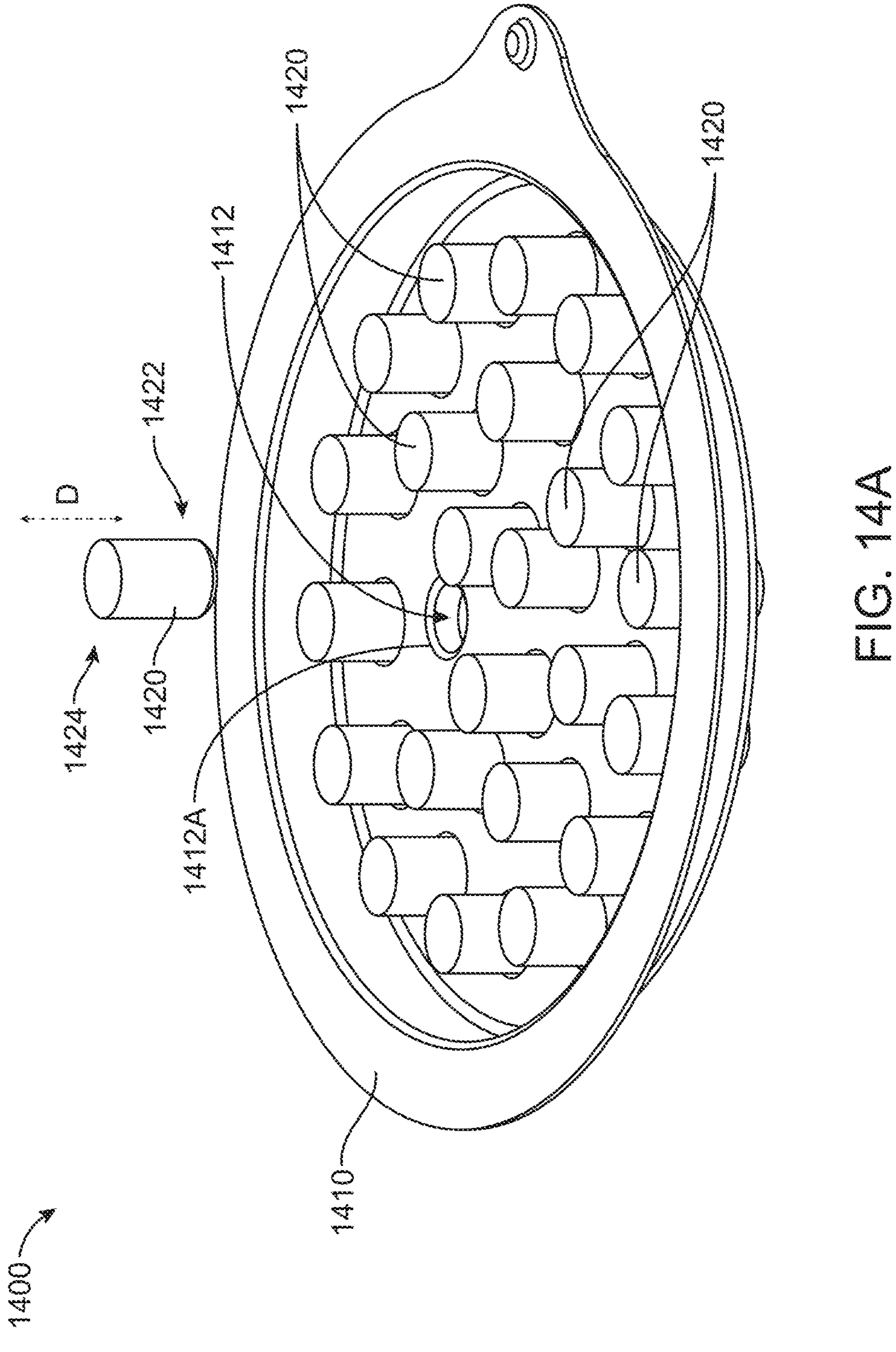
FIG. 14A is a top perspective view of a swab cartridge, according to embodiments of the present disclosure.
Figure 14B:
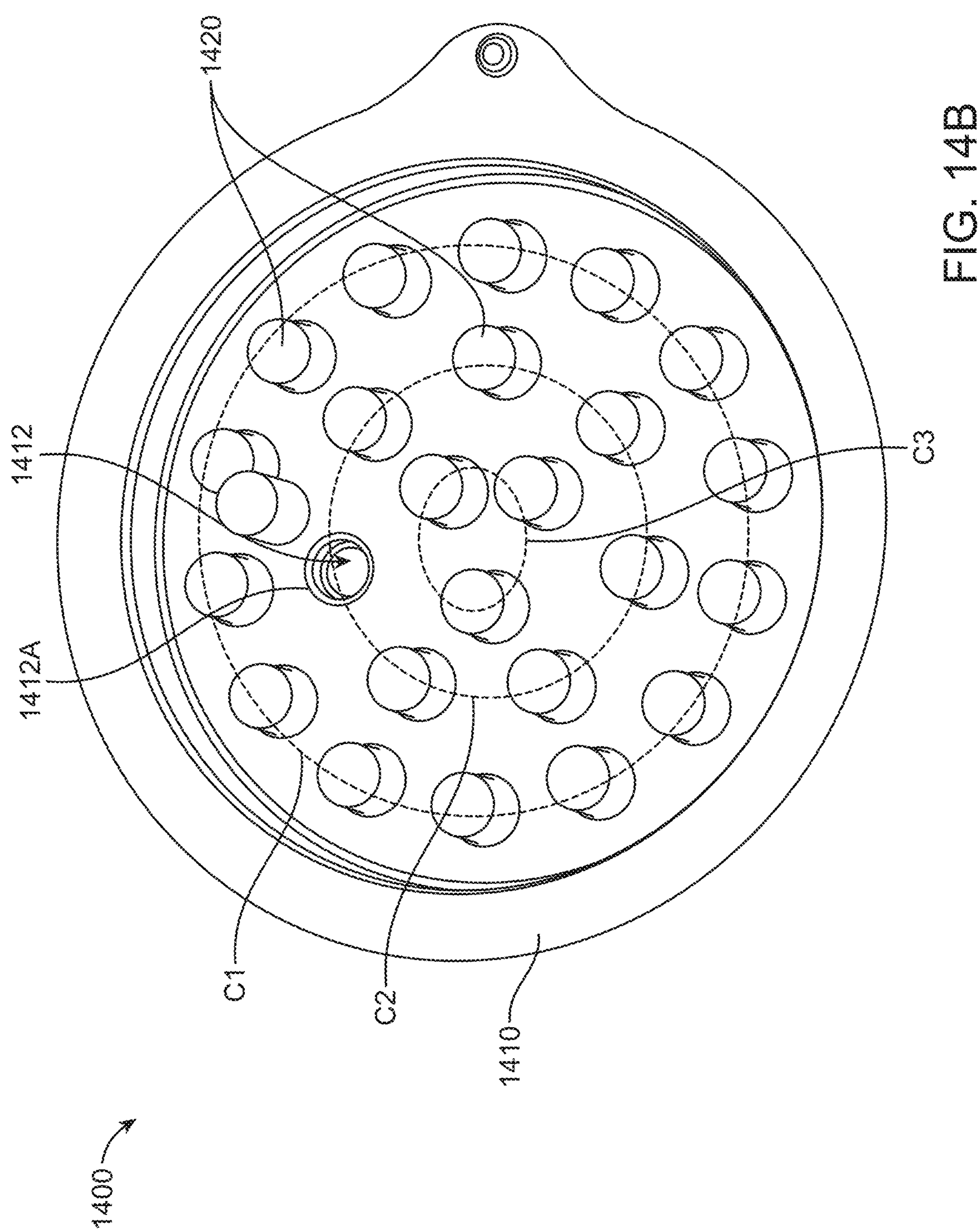
FIG. 14B is another top perspective view of the swab cartridge of FIG. 14A.

FIGS. 14A and 14B show a swab cartridge that can be used in an automated system for vial preparations. The swab cartridge described herein below can be used with any automated or semi-automated system in which a vial is required to be disinfected. For instance, the swab cartridge described herein below can be used in any or all of the vial preparation modules described herein above.

A swab cartridge for use with an automated vial preparation module can hold a plurality of swabs (swab stock) in such a manner that each swab can be accessed by a swab gripper (for example, the swab gripper described herein above), optionally with minimal movement of the gripper and the swab cartridge, and that each swab can be gripped by the gripper independently of the other swabs. For instance, each of the swabs can be held in the swab cartridge independently of adjacent swabs.

In general, a swab cartridge can comprise a cartridge housing formed with a plurality of swab stabilizing locations, each location for receiving and stabilizing (for example, holding or otherwise supporting in place) a single swab. A plurality of swabs corresponding to the plurality of swab stabilizing locations can be stabilized at locations, with each swab being stabilized at a corresponding one of the plurality of swab stabilizing locations independently of adjacent swabs. Each swab can be spaced apart from adjacent swabs such that a gripper can enter into that space and access each swab independently to pick up the swab from the cartridge. Accordingly, each of the stabilizing locations can be spaced from adjacent swab stabilizing locations by at least 1 mm, 2 mm, 3 mm, 4 mm, 5 mm, or higher distance.

Each of the swab stabilizing locations can have any suitable structure for holding a single swab. For example, the stabilizing locations can include slots or openings, each suitable for at least partially receiving therein a single swab; mounting elements in which a single swab can be mounted at a single mounting element; or any other equivalent structure to stabilize single swabs independently. Each of the swab stabilizing locations can be shaped, for example, to have a depth or height dimension, to support the swab along at least a portion of the height dimension of the swab. For example, the height dimension of the swab can be supported by a height or depth dimension of the stabilizing location.

Each swab can have a swab stabilizing portion that can be used for stabilizing the swab at the stabilizing location, and a swab grippable portion that can protrude from the stabilizing location and can be used for gripping the swab. The swab grippable portion of each swab can be spaced from adjacent swabs, so as to allow space (e.g. an empty volume surrounding the grippable portion) for the gripper to access the swab.

FIGS. 14A and 14B show a swab cartridge 1400 including a cartridge housing 1410 formed with a plurality of swab stabilizing locations 1412, which in the illustrated example are formed as openings 1412. Each opening 1412 receives therewithin a corresponding one swab 1420 of the plurality of swabs 1420. Each swab 1420 comprises a swab stabilizing portion 1422 and a swab grippable portion 1424. The swab stabilizing portion 1422 is received with a corresponding opening 1412, and the swab grippable portion 1424 protrudes therefrom. As can be seen in FIGS. 14A and 14B, the swab grippable portion 1424 of each swab 1420 is spaced from the adjacent swabs.

Each of the openings 1412 comprises a rim 1412A through which the swab 1420 can be received in the opening 1412 in a direction of insertion, which in the illustrated example is the longitudinal direction of the swab. The swab 1420 can be inserted and removed in the corresponding opening in the direction of insertion D (which can be referred to as swab removal direction D as well). The openings 1412 have depth dimensions at least enough to support the swab along at least a portion of the height dimension of the swab 1420.

In some examples, removal of swabs from the corresponding swab stabilizing locations may require application of a removing force of magnitude greater than a threshold force. For example, the force required to remove a swab can be understood as a force required to pluck a swab from the cartridge. The dimensions of the swab and the stabilizing location can define the force required for removal (and insertion) of the swab. In some examples, the swab is compressively held in the swab stabilizing location.

In the illustrated example, the swab stabilizing portion 1422 can have a swab cross-sectional area perpendicular to the swab insertion direction D and the rim 1412A of the opening 1412 can have an opening cross-sectional area perpendicular to the swab insertion direction D, and the swab cross-sectional area can be larger than the opening cross-sectional area. In other words, or additionally, the swab stabilizing portion 1422 has a circular swab cross-section taken perpendicular to the swab insertion direction D, and the rim 1412A of the opening 1412 has a circular opening cross-section taken perpendicular to the swab insertion direction D, and a diameter of the circular swab cross-section can be longer than a diameter of the circular opening cross-section.

In general, the stabilizing locations can be arranged in concentric circles (rings), such that each swab can be accessed by a gripper by minimal movement of the gripper. For example, a gripper can be aligned vertically above a swab in an outermost circle, and then the swab cartridge can be rotated (about an axis passing through the center of circles) and each swab in the outermost circle can be positioned under the gripper without moving the gripper. Thus, the gripper can access each swab in the outermost circle by just rotating the cartridge. Similarly, the gripper can be aligned vertically above a swab in any one of the concentric circles, and by rotating the cartridge each swab in that circle can be accessed without moving the gripper other than towards and away from the swab. One such example is described above with reference to FIG. 10D.

In the illustrated example, the cartridge 1400 is disc shaped and the openings 1412 and thus the swabs 1420 are arranged in concentric circles depicted by dotted circles C1 (outermost), C2, and C3 (innermost), and thus can be accessed as described above.

Figures 15A, 15B:
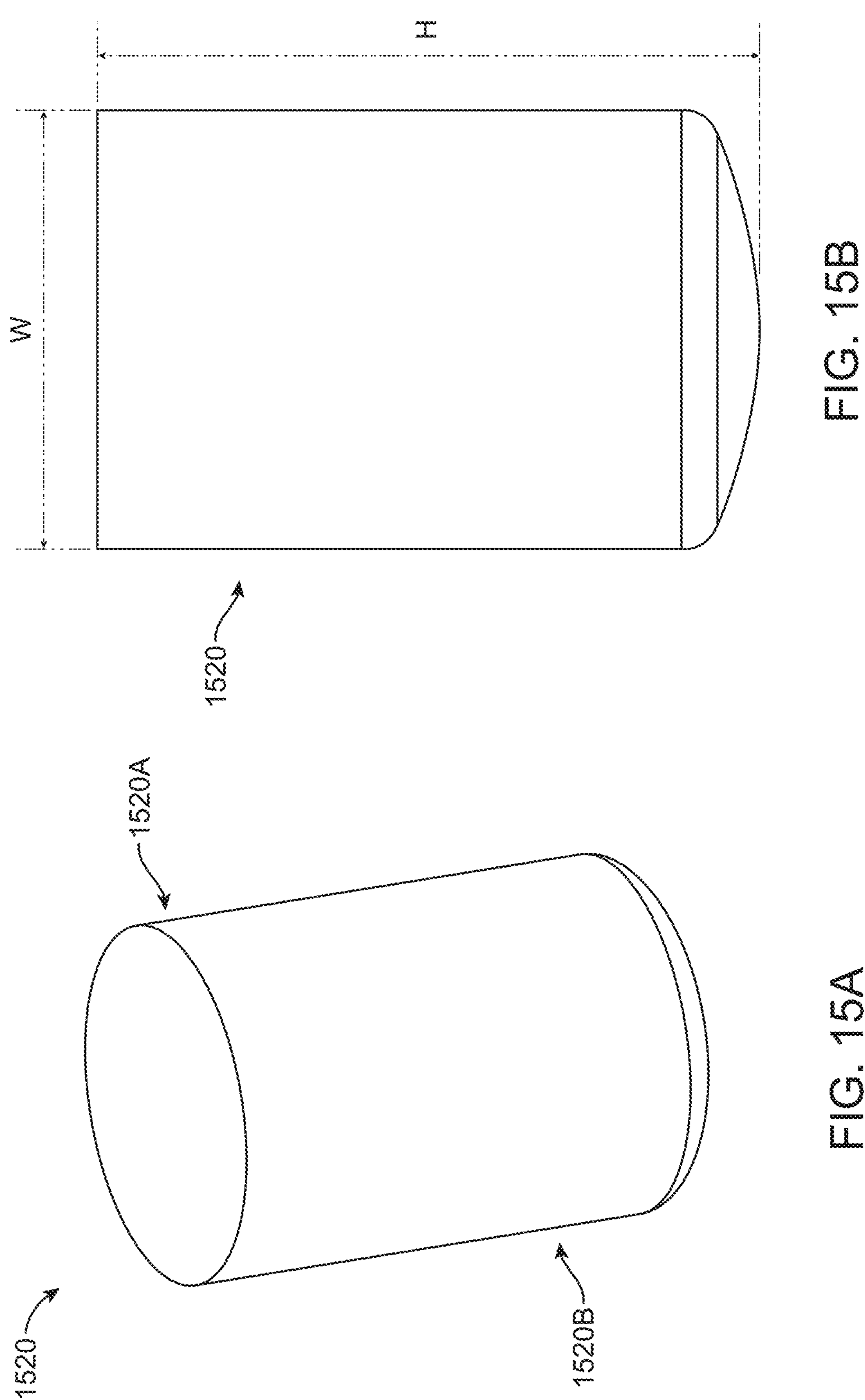
FIG. 15A is a top perspective view of a swab, according to embodiments of the present disclosure.
FIG. 15B is a side view of the swab of FIG. 15A.

FIGS. 15A and 15B show an exemplary swab 1520 that can be used for disinfecting a vial septum, for example, manually or in an automated system for vial preparations. The swab 1520 can be arranged in a swab cartridge, for example the swab cartridge 1400 described above, and all the description provided below with respect to the swab 1520 can apply to swabs 1420 of the swab cartridge 1400 described above.

In general, a swab can include one or more of following features, in any combinations:

- the swab can be made of a nonwoven material;
- the swab can have a height dimension, in the direction extending between a swab top portion and a swab bottom portion, and a width dimension orthogonal to the height dimension;
- a ratio of a height dimension to a width dimension can range between 1.2 and 1.7;
- the swab can have a rigidity along the height dimension higher than a rigidity along the width dimension;
- the nonwoven material can have average pore size between 8 μm to 12 μm;
- the swab can be made of an at least partially absorbent material;
- the swab can be made of a breathable material;
- the swab can be made of a hydrophilic material;
- the swab can be made of a thermoplastic material;
- the swab can be made of ultra-high-molecular-weight polyethylene (UHMW-PE);
- the height dimension can be between 6 mm to 15 mm;
- the width dimension can be between 4 mm to 10 mm;
- the swab can be cylindrical shaped.

In the example illustrated in FIGS. 15A and 15B, the swab 1520 is cylindrical shaped made of nonwoven material. The swab 1520 has a height dimension H extending between a top portion 1520A and a bottom portion 1520B, and a width dimension W orthogonal to the height dimension H.

The invention claimed is:

1. An automated vial preparation module that, when in use, prepares vials for being used in pharmaceutical compounding, said preparation of vials comprising at least cleaning a septum of a vial, said vial preparation module comprising:

a vial mount having a mount top surface for placing thereon a vial to be prepared in an upright orientation;

a manipulator including a swab gripper operable to grip at least a first swab; and control circuitry configured for:

maneuvering at least one of the vial mount and the manipulator with respect to the other to position the swab gripper at least partially vertically above the vial mount; and bringing the first swab gripped by the swab gripper into direct contact with a septum of the vial placed upright on the mount top surface.

2. The automated vial preparation module according to claim 1, further comprising a disinfecting solution reservoir holding unit operable to hold a disinfecting solution reservoir, wherein the control circuitry is operable for controlling applying of disinfecting solution stored in the disinfecting solution reservoir onto the septum of the vial.

3. The automated vial preparation module according to claim 2, further comprising a dropper mechanism operable to selectively drip the disinfecting solution from the disinfecting solution reservoir held at the disinfecting solution reservoir holding unit, and the control circuitry is operable for controlling the applying of disinfecting solution on the septum by maneuvering the dropper mechanism to drip a controlled volume of the disinfecting solution from the disinfecting solution reservoir onto the septum prior to said bringing the first swab into direct contact with the septum.

4. The automated vial preparation module according to claim 2, wherein the control circuitry is operable for controlling the applying of disinfecting solution onto the septum of the vial by maneuvering the manipulator for at least partially soaking the first swab with the disinfecting solution stored in the disinfecting solution reservoir prior to said bringing the first swab into direct contact with the septum.

5. The automated vial preparation module according to claim 2, further comprising an imaging apparatus for imaging a field of view including at least the septum of the vial, wherein the control circuitry is operable to monitor the application of the disinfecting solution on the septum based on said imaging.

6. The automated vial preparation module according to claim 1, wherein the control circuitry is operable for maneuvering at least one of the vial mount and the manipulator with respect to the other to wipe the septum of the vial with the first swab.

7. The automated vial preparation module according to claim 6, wherein the control circuitry is operable for maneuvering the vial mount to rotate the vial with respect to the first swab about a vial longitudinal axis for wiping the septum with the first swab.

8. The automated vial preparation module according to claim 7, wherein the control circuitry is operable for maneuvering the vial mount to rotate the vial in one or more sets of repeated to and fro pivoting movements with respect to corresponding one or more neutral positions by a first predetermined angle, each neutral position corresponding to a set of repeated to and fro pivoting movement.

9. The automated vial preparation module according to claim 1, wherein said control circuitry is operable for maneuvering the swab gripper to grip a second swab, and for maneuvering at least one of the vial mount and the manipulator with respect to the other to position the swab gripper at least partially vertically above the vial mount, and to bring the second swab gripped by the swab gripper into direct contact with the septum of the vial and to wipe the septum with the second swab for pushing off residue from the septum.

10. The automated vial preparation module according to claim 9, wherein said control circuitry is operable for moving said at least one of the vial mount and the second swab linearly with respect to the other in a lateral direction.

11. The automated vial preparation module according to claim 1, further comprising an ultraviolet (UV) radiation source, wherein said control circuitry is operable for maneuvering at least one of the vial mount and the UV radiation source with respect to the other to expose the septum to the UV radiation.

12. The automated vial preparation module according to claim 1, further comprising vial transferring means operable at least for picking up a vial from a vial storage region and placing the vial on the vial mount.

13. The automated vial preparation module according to claim 12, wherein the vial transferring means is operable to one or both of: de-cap the vial; remove a vial adaptor from a blister and mount the vial adaptor on the vial.

14. The automated vial preparation module according to claim 1, wherein the control circuitry is operable for labelling the vial with a time stamp indicative of a beyond use date of the vial.

15. The automated vial preparation module according to claim 1, further comprising a swab cartridge holder for holding a swab cartridge, said control circuitry being operable for maneuvering at least one of the swab cartridge holder and the swab gripper with respect to each other for using the swab gripper to pick up a swab from a swab cartridge held at the swab cartridge holder.

16. The automated vial preparation module according to claim 1, further comprising a housing defining an inner controlled environment, said manipulator and said vial mount being positioned within the housing.

17. The automated vial preparation module according to claim 1, wherein the direct contact between the first swab and the vial septum comprises friction-based contact for microbial reduction.

18. An automated method for preparation of vials for reducing a risk of contamination, the method carried out by an automated vial preparation module comprising a vial mount and a manipulator including a swab gripper, said method comprising steps of:

receiving, at a mount top surface of the vial mount, a vial to be prepared in an upright orientation;

gripping, by the swab gripper of the manipulator, at least a first swab; and maneuvering at least one of the vial mount and the manipulator with respect to the other to position the swab gripper at least partially vertically above the vial mount, and bringing the first swab gripped by the swab gripper into direct contact with a septum of the vial placed upright on the mount top surface for cleaning the vial septum.

19. The automated method according to claim 18, further comprising applying a disinfecting solution onto the septum of the vial.

20. The automated method according to claim 19, wherein applying the disinfecting solution on the septum comprises dripping a controlled volume of the disinfecting solution from a disinfecting solution reservoir onto the septum prior to said bringing the first swab into direct contact with the septum.

21. The automated method according to claim 19, wherein applying the disinfecting solution onto the septum comprises at least partially soaking the first swab with a disinfecting solution stored in a disinfecting solution reservoir prior to said bringing the first swab into direct contact with the septum.

22. The automated method according to claim 18, further comprising maneuvering at least one of the vial mount and the manipulator with respect to the other to wipe the septum with the first swab.

23. The automated method according to claim 18, further comprising, during the step of said wiping the septum with the first swab, imaging a field of view including at least the septum of the vial, and, monitoring the accuracy of wiping based on said imaging.

24. The automated method according to claim 18, further comprising:

gripping, using the swab gripper of the manipulator, at least a second swab; and maneuvering at least one of the vial mount and the manipulator with respect to the other to position the swab gripper at least partially vertically above the vial mount, bringing the second swab gripped by the swab gripper into direct contact with the septum of the vial, and wiping the septum with the second swab for pushing off residue from the septum.

25. The automated method according to claim 24, wherein wiping the septum with the second swab comprises moving said at least one of the vial and the second swab linearly with respect to the other in a lateral direction.

26. The automated method according to claim 18, further comprising exposing the septum to ultraviolet (UV) radiation.

27. The automated method according to claim 18, further comprising mounting a vial adaptor on the vial.

28. The automated method according to claim 18, further comprising labelling the vial with a time stamp indicative of a beyond use date of the vial.

29. The automated method according to claim 18, further comprising de-capping the vial prior to the step of said applying the disinfecting solution onto the septum of the vial.

30. The automated method according to claim 18, wherein the automated vial preparation module comprises a housing defining an inner controlled environment, said manipulator and said vial mount being positioned within the housing, wherein the method further comprises delivering and directing airflow inside the housing onto the septum of the vial.

* * * * *